(12) United States Patent
Wall et al.

(10) Patent No.: US 7,326,788 B2
(45) Date of Patent: Feb. 5, 2008

(54) QUINOLINONE DERIVATIVES AS INHIBITORS OF C-FMS KINASE

(75) Inventors: Mark J. Wall, Harleysville, PA (US); Mark R. Player, Phoenixville, PA (US); Raymond Joseph Patch, Yardley, PA (US); Sanath Meegalla, Boothwyn, PA (US); Jian Liu, Plainsboro, NJ (US); Carl R. Illig, Phoenixville, PA (US); Wing Cheung, Plainsboro, NJ (US); Jinsheng Chen, Exton, PA (US); Davoud Asgari, Newtown, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 343 days.

(21) Appl. No.: 10/894,940

(22) Filed: Jul. 20, 2004

(65) Prior Publication Data

US 2005/0049274 A1    Mar. 3, 2005

Related U.S. Application Data

(60) Provisional application No. 60/488,811, filed on Jul. 22, 2003.

(51) Int. Cl.
*C07D 215/38* (2006.01)
*C07D 215/44* (2006.01)

(52) U.S. Cl. ............................. 546/157; 546/153
(58) Field of Classification Search ............ 546/153, 546/157; 514/312, 313
See application file for complete search history.

(56) References Cited

U.S. PATENT DOCUMENTS

| | | | |
|---|---|---|---|
| 3,542,785 A | 11/1970 | Carney | |
| 6,169,096 B1 | 1/2001 | Venet et al. | |
| 6,258,824 B1 | 7/2001 | Yang | |
| 6,420,382 B2 | 7/2002 | Fraley et al. | |
| 6,740,662 B1 * | 5/2004 | Iwata et al. | 514/300 |
| 6,822,097 B1 | 11/2004 | Norman et al. | |
| 2004/0092535 A1 | 5/2004 | Barsanti et al. | |

FOREIGN PATENT DOCUMENTS

| | | |
|---|---|---|
| EP | 1225 173 A1 | 7/2002 |
| WO | WO 00/34244 A1 | 6/2000 |
| WO | WO 02/22598 A1 | 3/2002 |
| WO | WO 02/092076 A1 | 11/2002 |
| WO | WO 02/098425 A1 | 12/2002 |

OTHER PUBLICATIONS

Croisy-Delcey, Bioorg & Med Chemistry, vol. 8(11), pp. 2629-2641, 2000.*
Croisy-Delcey, Martine et al., "Diphenyl Quinolines and Isoquinolines: Synthesis and Primary Biological Evaluation", Bioorganic & Medicinal Chemistry, vol. 8, No. 11, 2000, pp. 26269-2641.
Nesvadba, Petr et al., "Oxidative Elimination of Phenyl Group from a Position of Quaternary Quinolinium Salts", Collection Czechoslovak Chem. Commun., vol. 48, pp. 2965-2969, 1983.
Iyer, R.N. et al., Studies in Potential Antifertility Agents: Part VI—Synthesis of Dialkylaminoethoxy Derivatives of 3,4-Diphenylcarbostyril, 3,4-Diphenylcinnoline, 2,3-Diphenyl-4-quinazolone & 2,3-Diphenylquinoxaline:, Indian Journal of Chemistry, vol. 11, pp. 234-236, Mar. 1973.
Marsili, A. et al., "Conversion of Indones to Quinoline and Isoquinoline Derivatives—IV. Schmidt REaction with 2(o-Carbomethoxyphenyl)-3-Phenylindone", NIelsevier Science Publishers, Amsterdam, Tetrahedron, vol. 24, No. 14, pp. 4993-4999, 1968.
Marsili A., "Conversion of Indones to Quinoline and Isoquinoline Derivatives—III. Schmidt Reaction with 2,3-Diphenylindone and Similar Compounds", Tetrahedron, vol. 24, pp. 4981-4991, 1968.
PCT International Search Report, dated Feb. 8, 2005, for PCT Int'l. Appln. No. PCT/US2004/023423.
Vostrova, Ukrainskii Khimicheskii Zhurnal, 57(12), 1991, pp. 1325-1328.

* cited by examiner

*Primary Examiner*—D. Margaret Seaman

(57) ABSTRACT

The invention is directed to compounds of Formulae I and II:

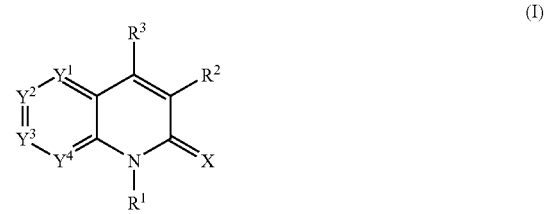

(I)

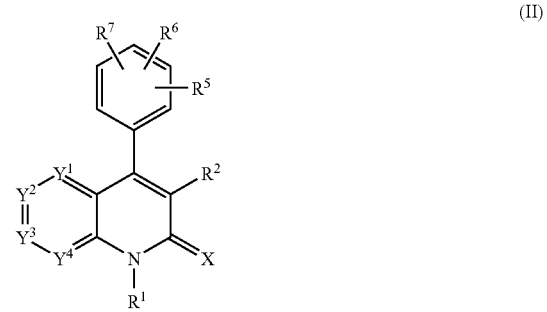

(II)

wherein $R^1$, $R^2$, $R^3$, $R^5$, $R^6$, $Y^1$, $Y^2$, $Y^3$, $Y^4$ and X are set forth in the specification, as well as solvates, hydrates, tautomers or pharmaceutically acceptable salts thereof, that inhibit protein tyrosine kinases, especially c-fms kinase.

6 Claims, No Drawings

QUINOLINONE DERIVATIVES AS INHIBITORS OF C-FMS KINASE

REFERENCE TO RELATED APPLICATIONS

This application is a non-provisional filing of Provisional U.S. Ser. No. 60/488,811, filed Jul. 22, 2003 now abandoned.

FIELD OF THE INVENTION

The invention relates to novel compounds that function as protein tyrosine kinase inhibitors. More particularly, the invention relates to novel quinolinone derivatives that function as inhibitors of c-fms kinase.

BACKGROUND OF THE INVENTION

Protein kinases are enzymes that serve as key components of signal transduction pathways by catalyzing the transfer of the terminal phosphate from ATP to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-IR") are structurally and functionally related but exert distinct biological effects. IGF-IR over-expression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. One embodiment of the invention is directed to the novel compounds of Formula I:

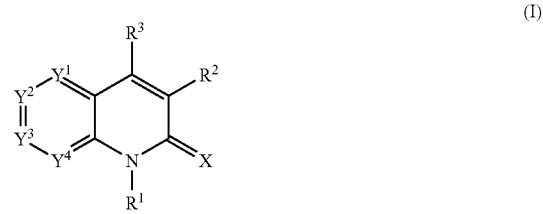

or a solvate, hydrate, tautomer or pharmaceutically acceptable salt thereof, wherein $R^1$ is
—H, —$C_{1-6}$ alkyl, cycloalkyl, aryl, aralkyl, heteroaryl, heteroaralkyl, —$COR_a$, —$COOR_a$, —$CONR_aR_b$ or —$SO_2R_a$, $R^2$ is
phenyl, naphthyl or biaryl, each of which may be optionally substituted with one or more of —$C_{1-6}$ alkyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R$, —$SO_2NR_aR_b$, —N═C($R_a$)—$NR_bR_c$, —$CH_2NR_aR_b$, —$CH_2NR_aR_bNR_cR_d$, —$NR_aSO_2R_b$, —$NR_aCONR_bR_c$, or —$CH_2N(CH_2CH_2)_2NR_a$; or
a 5- to 7-membered mono- or a 8- to 10-membered bicyclic heteroaromatic or heterocyclic ring having from one to four heteroatoms selected from N, O or S, and may be optionally substituted with one or more of —$C_{1-6}$ alkyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —NO$_2$, —SO$_2$R$_a$, —SO$_3$R$_a$, —SO$_2$NR$_a$R$_b$, —N=C(R$_a$)—NR$_b$R$_c$, —CH$_2$NR$_a$R$_b$, —CH$_2$NR$_a$R$_b$NR$_c$R$_d$, —NR$_a$SO$_2$R$_b$,—NR$_a$CONR$_b$R$_c$, —N(R$_a$)CON(R$_b$)-alkyl-R$_c$, or —CH$_2$N(CH$_2$CH$_2$)$_2$NR$_a$;

R$^3$ is
- phenyl, naphthyl, biaryl or cycloalkyl, each of which may be optionally substituted with one or more of —C$_{1-6}$ alkyl, —C$_{2-6}$ alkenyl, amino, aminoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SR$_a$, —SO$_2$R$_a$, —NR$_a$SO$_2$R$_b$, —SO$_3$R$_a$ or —SO$_2$NR$_a$R$_b$; or
- a 5- to 7-membered heterocyclyl ring having from one to four heteroatoms selected from N, O or S, and may be optionally substituted with one or more of —C$_{1-6}$ alkyl, —C$_{2-6}$ alkenyl, amino, aminoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SR$_a$, —SO$_2$R$_a$, —NR$_a$SO$_2$R$_b$, —SO$_3$R$_a$ or —SO$_2$NR$_a$R$_b$; or
- a 5- to 7-membered mono- or a 8- to 10-membered bicyclic heteroaromatic ring having from one to four heteroatoms selected from N, O or S, and may be optionally substituted with one or more of —C$_{1-6}$ alkyl, —C$_{2-6}$ alkenyl, amino, aminoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SR$_a$, —SO$_2$R$_a$, —NR$_a$SO$_2$R$_b$, —SO$_3$R$_a$ or —SO$_2$NR$_a$R$_b$;

X is
O, S, N(R$_a$)N(R$_a$)(R$_b$), N(R$_a$)N(R$_b$)COR$_c$; and

Y$^1$, Y$^2$, Y$^3$ and Y$^4$ are independently —C(R$^4$)— or —N—, wherein each R$^4$ is independently
- —H, —C$_{1-6}$ alkyl, —C$_{2-6}$ alkenyl, amino, aminoalkyl, halogen, hydroxy, hydroxyalkyl, —CF$_3$, alkoxy, aryl, aralkyl, heteroaryl, heteroaralkyl, aryloxy, heteroaryloxy, arylalkoxy, SR$_a$, NR$_a$R$_b$, PhCF$_3$, —OCF$_3$, —OCO-alkyl, —COR$_a$, —CN, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$, —N(R$_a$)SO$_2$R$_b$, or
- wherein two independent R$_4$ substituents, taken together with Y$^1$=Y$^2$, Y$^2$=Y$^3$ or Y$^3$=Y$^4$, form a 5- to 7-membered cyclic, heterocyclic, aryl or heteroaryl ring containing from 0-3 heteroatoms selected from N, O or S, which may be optionally substituted with —H, —C$_{1-6}$ alkyl, amino, aminoalkyl, halogen, hydroxy, hydroxyalkyl, —CF$_3$, alkoxy, aryl, aralkyl, heteroaryl, heteroaralkyl, aryloxy, heteroaryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SO$_2$R$_a$, —N(R$_a$)SO$_2$R$_b$, —SO$_3$R$_a$ or —SO$_2$NR$_a$R$_b$, wherein R$_a$, R$_b$, R$_c$ and R$_d$ are independently hydrogen, alkoxy, alkyl, alkenyl, cycloalkyl, aryl, aralkyl, heteroaralkyl or heteroaryl, any one of which except hydrogen may be substituted with one or more of the following: —SO$_2$NH$_2$, SO$_2$-alkyl, or —CO$_2$-alkyl.

In another embodiment, the invention is directed to the novel compounds of Formula II:

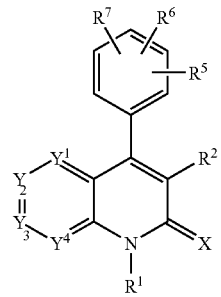

(II)

or a solvate, hydrate, tautomer or pharmaceutically acceptable salt thereof, wherein R$^1$ is
- —H, —C$_{1-6}$ alkyl, cycloalkyl, aryl, aralkyl, heteroaryl, heteroaralkyl, —COR$_a$, —COOR$_a$, —CONR$_a$R$_b$ or —SO$_2$R$_a$, R$^2$ is
- a 5- to 7-membered heterocyclic or heteroaromatic ring having from one to three heteroatoms selected from N, O or S, and may be optionally substituted with one or more of —C$_{1-6}$ alkyl, amino, aminoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SO$_2$R$_a$, —NR$_a$SO$_2$R$_b$, —SO$_3$R$_a$ or —SO$_2$NR$_a$R$_b$;

R$^5$, R$^6$ and R$^7$ are independently
- —C$_{1-6}$ alkyl, —C$_{2-6}$ alkenyl, amino, aminoalkyl, heteroaryl, halogen, meta-hydroxy, para-hydroxy, meta-methoxy, para-methoxy, —C$_{2-5}$ alkoxy, —CF$_3$, aryl, aralkyl, heteroaralkyl, aryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SR$_a$, —SO$_2$R$_a$, —NR$_a$SO$_2$R$_b$, —SO$_3$R$_a$ or —SO$_2$NR$_a$R$_b$;

X is
O, S, N(R$_a$)N(R$_a$)(R$_b$), N(R$_a$)N(R$_b$)COR$_c$; and

Y$^1$, Y$^2$, Y$^3$ and Y$^4$ are independently
—C(R$^4$)— or —N—, wherein each R$^4$ is independently
- —H, —C$_{1-6}$ alkyl, —C$_{2-6}$ alkenyl, amino, aminoalkyl, halogen, hydroxy, hydroxyalkyl, —CF$_3$, alkoxy, aryl, aralkyl, heteroaryl, heteroaralkyl, aryloxy, heteroaryloxy, arylalkoxy, SR$_a$, NR$_a$R$_b$, PhCF$_3$, —OCF$_3$, —OCO-alkyl, —COR$_a$, —CN, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_a$, —N(R$_a$)SO$_2$R$_b$, or
- wherein two independent R$^4$ substituents, taken together with Y$^1$=Y$^2$ Y$^2$=Y$^3$ or Y$^3$=Y$^4$, form a 5- to 7-membered cyclic, heterocyclic, aryl or heteroaryl ring containing from 0-3 heteroatoms selected from N, O or S, which may be optionally substituted with —H, —C$_{1-6}$ alkyl, amino, aminoalkyl, halogen, hydroxy, hydroxyalkyl, —CF$_3$, alkoxy, aryl, aralkyl, heteroaryl, heteroaralkyl, aryloxy, heteroaryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SO$_2$R$_a$, —NR$_a$SO$_2$R$_b$, —SO$_3$R$_a$ or —SO$_2$NR$_a$R$_b$;

wherein R$_a$, R$_b$, R$_c$ and R$_d$ are independently hydrogen, alkoxy, alkyl, alkenyl, cycloalkyl, aryl, aralkyl, heteroaralkyl or heteroaryl, any one of which except hydrogen may be substituted with one or more of the following: —SO$_2$NH$_2$, SO$_2$-alkyl, or —CO$_2$-alkyl, with the proviso that R$^2$ is neither isoxazoline, pyrazoline, nor a benzimidazole ring and with the proviso that if Y$^2$ is —C(R$^4$), then R$^4$ is not a —C$_1$-heteroaromatic.

The compounds of Formulae I and II are especially potent inhibitors of the c-fms protein tyrosine kinase.

The invention also relates to methods of inhibiting protein tyrosine kinase activity in a mammal by administration of a therapeutically effective amount of at least one compound of Formula I or II.

DETAILED DESCRIPTION OF THE INVENTION

The invention is directed to the novel compounds of Formula I:

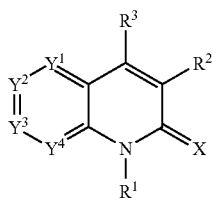

(I)

or a solvate, hydrate, tautomer or pharmaceutically acceptable salt thereof, wherein R$^1$ is
- —H, —C$_{1-6}$ alkyl, cycloalkyl, aryl, aralkyl, heteroaryl, heteroaralkyl, —COR$_a$, —COOR$_a$, —CONR$_a$R$_b$ or —SO$_2$R$_a$, R$^2$ is
- phenyl, naphthyl or biaryl, each of which may be optionally substituted with one or more of —C$_{1-6}$ alkyl, amino, aminoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SO$_2$R$_a$, —SO$_3$R, —SO$_2$NR$_a$R$_b$, —N═C(R$_a$)—NR$_b$R$_c$, —CH$_2$NR$_a$R$_b$, —CH$_2$NR$_a$NR$_b$NR$_d$, —NR$_a$SO$_2$R$_b$, —NR$_a$CON R$_b$R$_c$, or —CH$_2$N(CH$_2$CH$_2$)$_2$NR$_a$; or
- a 5- to 7-membered mono- or a 8- to 10-membered bicyclic heteroaromatic or heterocyclic ring having from one to four heteroatoms selected from N, O or S, and may be optionally substituted with one or more of —C$_{1-6}$ alkyl, amino, aminoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SO$_2$R$_a$, —SO$_3$R$_a$, —SO$_2$NR$_a$R$_b$, —N═C(R$_a$)—NR$_b$R$_c$, —CH$_2$NR$_a$R$_b$, —CH$_2$NR$_a$R$_b$NR$_c$R$_d$, —NR$_a$SO$_2$R$_b$,—NR$_a$CONR$_b$R$_c$, —N(R$_a$)CON(R$_b$)-alkyl-R$_c$, or —CH$_2$N(CH$_2$CH$_2$)$_2$NR$_a$;

R$^3$ is
- phenyl, naphthyl, biaryl or cycloalkyl, each of which may be optionally substituted with one or more of —C$_{1-6}$ alkyl, —C$_{2-6}$ alkenyl, amino, aminoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SR$_a$, —SO$_2$R$_a$, —NR$_a$SO$_2$R$_b$, —SO$_3$R$_a$ or —SO$_2$NR$_a$R$_b$; or
- a 5- to 7-membered heterocyclyl ring having from one to four heteroatoms selected from N, O or S, and may be optionally substituted with one or more of —C$_{1-6}$ alkyl, —C$_{2-6}$ alkenyl, amino, aminoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$,—CN, —COOR$_a$, —CONR$_a$R$_b$, N(R$_a$)COR$_b$, —NO$_2$, —SR$_a$, —SO$_2$R$_a$, —NR$_a$SO$_2$R$_b$, —SO$_3$R$_a$ or —SO$_2$NR$_a$R$_b$; or
- a 5- to 7-membered mono- or a 8- to 10-membered bicyclic heteroaromatic ring having from one to four heteroatoms selected from N, O or S, and may be optionally substituted with one or more of —C$_{1-6}$ alkyl, —C$_{2-6}$ alkenyl, amino, aminoalkyl, heteroaryl, halogen, hydroxy, —CF$_3$, alkoxy, aryl, aralkyl, heteroaralkyl, aryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SR$_a$, —SO$_2$R$_a$, —NR$_a$SO$_2$R$_b$, —SO$_3$R$_a$ or —SO$_2$NR$_a$R$_b$;

X is
- O, S, N(R$_a$)N(R$_a$)(R$_b$), N(R$_a$)N(R$_b$)COR$_c$; and

Y$^1$, Y$^2$, Y$^3$ and Y4 are independently
- —C(R$^4$)— or —N—, wherein each R$^4$ is independently
- —H, —C$_{1-6}$ alkyl, —C$_{2-6}$ alkenyl, amino, aminoalkyl, halogen, hydroxy, hydroxyalkyl, —CF$_3$, alkoxy, aryl, aralkyl, heteroaryl, heteroaralkyl, aryloxy, heteroaryloxy, arylalkoxy, SR$_a$, NR$_a$R$_b$, PhCF$_3$, —OCF$_3$, —OCO-alkyl, —COR$_a$, —CN, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$, —N(R$_a$)SO$_2$R$_b$, or wherein two independent R$^4$ substituents, taken together with Y$^1$═Y$^2$, Y$^2$═Y$^3$ or Y$^3$═Y$^4$, form a 5- to 7-membered cyclic, heterocyclic, aryl or heteroaryl ring containing from 0-3 heteroatoms selected from N, O or S, which may be optionally substituted with —H, —C$_{1-6}$ alkyl, amino, aminoalkyl, halogen, hydroxy, hydroxyalkyl, —CF$_3$, alkoxy, aryl, aralkyl, heteroaryl, heteroaralkyl, aryloxy, heteroaryloxy, arylalkoxy, —OCF$_3$, —OCO-alkyl, —COR$_a$, —CN, —COOR$_a$, —CONR$_a$R$_b$, —N(R$_a$)COR$_b$, —NO$_2$, —SO$_2$R$_a$, —N(R$_a$)SO$_2$R$_b$, —SO$_3$R$_a$ or —SO$_2$NR$_a$R$_b$, wherein R$_a$, R$_b$, R$_a$ and R$_d$ are independently hydrogen, alkoxy, alkyl, alkenyl, cycloalkyl, aryl, aralkyl, heteroaralkyl or heteroaryl, any one of which except hydrogen may be substituted with one or more of the following: —SO$_2$NH$_2$, SO$_2$-alkyl, or —CO$_2$-alkyl.

In another embodiment, the invention is directed to the novel compounds of Formula II:

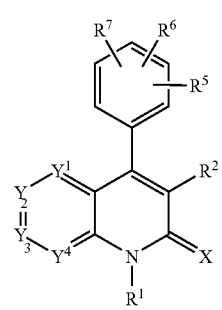

(II)

or a solvate, hydrate, tautomer or pharmaceutically acceptable salt thereof, wherein $R^1$ is
- —H, —$C_{1-6}$ alkyl, cycloalkyl, aryl, aralkyl, heteroaryl, heteroaralkyl, —$COR_a$, —$COOR_a$, —$CONR_aR_b$ or —$SO_2R_a$, $R^2$ is
- a 5- to 7-membered heterocyclic or heteroaromatic ring having from one to three heteroatoms selected from N, O or S, and may be optionally substituted with one or more of —$C_{1-6}$ alkyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$NR_aSO_2R_b$, —$SO_3R_a$ or —$SO_2NR_aR_b$;

$R^5$, $R^6$ and $R^7$ are independently
- —$C_{1-6}$ alkyl, —$C_{2-6}$ alkenyl, amino, aminoalkyl, heteroaryl, halogen, meta-hydroxy, para-hydroxy, meta-methoxy, para-methoxy, —$C_{2-5}$ alkoxy, —$CF_3$, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SR_a$, —$SO_2R_a$, —$NR_aSO_2R_b$, —$SO_3R_a$ or —$SO_2NR_aR_b$;

X is
- O, S, $N(R_a)N(R_a)(R_b)$, $N(R_a)N(R_b)COR_c$; and $Y^1$, $Y^2$, $Y^3$ and $Y^4$ are independently
- —$C(R^4)$— or —N—, wherein each $R^4$ is independently
- —H, —$C_{1-6}$ alkyl, —$C_{2-6}$ alkenyl, amino, aminoalkyl, halogen, hydroxy, hydroxyalkyl, —$CF_3$, alkoxy, aryl, aralkyl, heteroaryl, heteroaralkyl, aryloxy, heteroaryloxy, arylalkoxy, $SR_a$, $NR_aR_b$, $PhCF_3$, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, —$N(R_a)SO_2R_b$, or wherein two independent $R^4$ substituents, taken together with $Y^1=Y^2$, $Y^2=Y^3$ or $Y^3=Y^4$, form a 5- to 7-membered cyclic, heterocyclic, aryl or heteroaryl ring containing from 0-3 heteroatoms selected from N, O or S, which may be optionally substituted with —H, —$C_{1-6}$ alkyl, amino, aminoalkyl, halogen, hydroxy, hydroxyalkyl, —$CF_3$, alkoxy, aryl, aralkyl, heteroaryl, heteroaralkyl, aryloxy, heteroaryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$N(R_a)SO_2R_b$, —$SO_3R_a$ or —$SO_2NR_aR_b$, wherein $R_a$, $R_b$, $R_c$ and $R_d$ are independently hydrogen, alkoxy, alkyl, alkenyl, cycloalkyl, aryl, aralkyl, heteroaralkyl or heteroaryl, any one of which except hydrogen may be substituted with one or more of the following: —$SO_2NH_2$, $SO_2$-alkyl, or —$CO_2$-alkyl, with the proviso that $R^2$ is neither isoxazoline, pyrazoline, nor a benzimidazole ring and with the proviso that if $Y^2$ is —$C(R^3)$, then $R^3$ is not a —$C_1$-heteroaromatic.

Preferred compounds of Formula I are those wherein
$R^1$ is —H;
$R^2$ is
- a 5- to 7-membered heterocyclic or heteroaromatic ring having from one to three heteroatoms selected from N, O or S, and may be optionally substituted with one or more of —$C_{1-6}$ alkyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3F$, or —$SO_2NR_aR_b$;

$R^3$ is
- a 5- to 7-membered heterocyclyl ring having from one to four heteroatoms selected from N, O or S, and may be optionally substituted with one or more of —$C_{1-6}$ alkyl, —$C_{2-6}$ alkenyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SR_a$, —$SO_2R_a$, —$SO_3R_a$ or —$SO_2NR_aR_b$; or
- phenyl, or cycloalkyl, each of which may be optionally substituted with one or more of —$C_{1-6}$ alkyl, —$C_{2-6}$ alkenyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, $COR_a$, —CN, —$COOR_a$, —$CONR_aR_b$, —$N(R_a)COR_b$, —$NO_2$, —$SR_a$, —$SO_2R_a$, —$SO_3R_a$ or —$SO_2NR_aR_b$;

X is O; and
$Y^1$, $Y^2$, $Y^3$ and $Y^4$ are $C(R^4)$—, wherein each $R^4$ is independently
- —H, —$C_{1-6}$ alkyl, —$C_{2-6}$ alkenyl, amino, aminoalkyl, halogen, hydroxy, hydroxyalkyl, —$CF_3$, alkoxy, aryl, aralkyl, heteroaryl, heteroaralkyl, aryloxy, heteroaryloxy, arylalkoxy, $SR_a$, $NR_aR_b$, $PhCF_3$, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, —$N(R_a)SO_2R_b$, or wherein $R_a$, $R_b$, $R_c$ and $R_d$ are independently hydrogen, alkoxy, alkyl, alkenyl, cycloalkyl, aryl, aralkyl, heteroaralkyl or heteroaryl, any one of which except hydrogen may be substituted with one or more of the following: —$SO_2NH_2$, $SO_2$-alkyl, or —$CO_2$-alkyl.

Preferred compounds of Formula II are those wherein
$R^1$ is —H;
$R^2$ is
- a 5- to 7-membered heterocyclic or heteroaromatic ring having from one to three heteroatoms selected from N, O or S, and may be optionally substituted with one or more of —$C_{1-6}$ alkyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$;

X is O; and
$Y^1$, $Y^2$, $Y^3$ and $Y^4$ are —$C(R^4)$—, wherein each $R^4$ is independently
- -H, —$C_{1-6}$ alkyl, —$C_{2-6}$ alkenyl, amino, aminoalkyl, halogen, hydroxy, hydroxyalkyl, —$CF_3$, alkoxy, aryl, aralkyl, heteroaryl, heteroaralkyl, aryloxy, heteroaryloxy, arylalkoxy, $SR_a$, $NR_aR_b$, $PhCF_3$, —$OCF_3$, —OCO-alkyl, —$COR_a$, —CN, —$COOR_b$, —$CONR_aR_b$, —$N(R_a)COR_b$, —$NO_2$, —$SO_2R_a$, —$SO_3R_a$ or —$SO_2NR_aR_b$, —$N(R_a)SO_2R_b$, wherein $R_a$, $R_b$ and $R_c$ are independently hydrogen, alkyl, alkoxy, cycloalkyl, aryl, aralkyl, heteroaralkyl or heteroaryl, with the proviso that $R^2$ is neither isoxazoline, pyrazoline nor a benzimidazole ring and with the proviso that if $Y^2$ is —$C(R^4)$, then $R^4$ is not a —$C_1$-heteroaromatic.

The most preferred compounds of Formula I include, but are not limited to, 6-chloro-3-(3-methyl-isoxazol-5-yl)-4-(pyridin-4-yl)-1H-quinolin-2-one; 6-chloro-3-(3-methyl-isoxazol-5-yl)-4-(pyridin-3-yl)-1H-quinolin-2-one; 6-chloro-3-(3-methyl-isoxazol-5-yl)-4-(pyridin-2-yl)-1H- quinolin-2-one; 6-Chloro-3-(3-methyl-isoxazol-5-yl)-4-piperidin-1-yl-1H-quinolin-2-one; 6-Chloro-4-cycloheptyl-3-(3-methyl-isoxazol-5-yl)-1H-quinolin-2-one; 6-Chloro-4-cyclohex-1-enyl-3-(3-methyl-isoxazol-5-yl)-1H-quinolin-2-one; 6-Chloro-4-cyclohept-1-enyl-3-(3-methyl-isoxazol-5-yl)-1H-quinolin-2-one and pharmaceutically acceptable salts thereof.

The most preferred compounds of Formula II include, but are not limited to, 6-chloro-3-(3-methyl-isoxazol-5-yl)-4-phenyl-1H-quinolin-2-one; 6-bromo-3-(3-methyl-isoxazol-5-yl)-4-phenyl-1H-quinolin-2-one; 6-bromo-3-(3-methyl-isoxazol-5-yl)-4-(2-fluorophenyl)-1H-quinolin-2-one; 6-chloro-3-(3-methyl-isoxazol-5-yl)-4-(2-fluorophenyl)-1H-quinolin-2-one; 6-chloro-3-(3-methyl-isoxazol-5-yl)-4-(3-hydroxyphenyl)-1H-quinolin-2-one; 6-chloro-3-(3-ethyl-isoxazol-5-yl)-4-phenyl-1H-quinolin-2-one; 6-chloro-3-(3-(2-phenyl)ethyl-isoxazol-5-yl)-4-phenyl-1H-quinolin-2-one; 6-chloro-3-(3-isopropyl-isoxazol-5-yl)-4-phenyl-1H-quinolin-2-one; 3-(3-tert-butyl-isoxazol-5-yl)-6-chloro-4-phenyl-1H-quinolin-2-one; 6-chloro-3-(4-methyl-4,5-dihydro-oxazol-2-yl)-4-phenyl-1H-quinolin-2-one; 6-chloro-3-(4-isopropyl-4,5-dihydro-oxazol-2-yl)-4-phenyl-1H-quinolin-2-one; 6-chloro-3-(4-isobutyl-4,5-dihydro-oxazol-2-yl)-4-phenyl-1H-quinolin-2-one; 3-(4-tert-butyl-4,5-dihydro-oxazol-2-yl)-6-chloro-4-phenyl-1H-quinolin-2-one; 6-chloro-3-(4-methyl-oxazol-2-yl)-4-phenyl-1H-quinolin-2-one; 6-chloro-3-(4-ethyl-oxazol-2-yl)-4-phenyl-1H-quinolin-2-one; 6-chloro-3-(4-isopropyl-oxazol-2-yl)-4-phenyl-1H-quinolin-2-one; 6-chloro-3-(4-isobutyl-oxazol-2-yl)-4-phenyl-1H-quinolin-2-one; 3-(4-tert-butyl-oxazol-2-yl)-6-chloro-4-phenyl-1H-quinolin-2-one; 6-chloro-3-(2-methyl-2H-tetrazol-5-yl)-4-phenyl-1H-quinolin-2-one; 6-chloro-3-(2-ethyl-2H-tetrazol-5-yl)-4-phenyl-1H-quinolin-2-one; 6-chloro-3-(2-isopropyl-2H-tetrazol-5-yl)-4-phenyl-1H-quinolin-2-one; 6-chloro-3-(1H-imidazol-4-yl)-4-phenyl-1H-quinolin-2-one; 6-chloro-3-(1-methyl-1H-imidazol-4-yl)-4-phenyl-1H-quinolin-2-one; 6-chloro-3-(1-ethyl-1H-imidazol-4-yl)-4-phenyl-1H-quinolin-2-one; 6-chloro-3-(1-isopropyl-1H-imidazol-4-yl)-4-phenyl-1H-quinolin-2-one; 3-(5-bromo-pyridin-3-yl)-6-chloro-4-phenyl-1H-quinolin-2-one; 6-chloro-4-phenyl-3-pyridin-3-yl-1H-quinolin-2-one; 6-nitro-3-(3-methyl-isoxazol-5-yl)-4-phenyl-1H-quinolin-2-one; 3-(1-benzyl-1H-[1,2,3]triazol-4-yl)-6-chloro-4-phenyl-1H-quinolin-2-one; 3-(3-methyl-isoxazol-5-yl)-2-oxo-4-phenyl-1,2-dihydro-quinoline-6-carboxylic acid; 6-chloro-4-phenyl-3-pyridin-4-yl-1H-quinolin-2-one; 3-(3-Methyl-isoxazol-5-yl)-2-oxo-4-(4-vinyl-phenyl)-1,2-dihydro-quinoline-6-carbonitrile; 4-(4-Ethyl-phenyl)-3-(3-methyl-isoxazol-5-yl)-2-oxo-1,2-dihydro-quinoline-6-carbonitrile; 6-Chloro-4-(4-ethyl-phenyl)-3-(3H-imidazol-4-yl)-1H-quinolin-2-one; 3-(3-Methyl-isoxazol-5-yl)-2-oxo-4-phenyl-1,2-dihydro-quinoline-6-carbonitrile; 3-(3H-Imidazol-4-yl)-2-oxo-4-phenyl-1,2-dihydro-quinoline-6-carbonitrile; 6-Chloro-4-phenyl-3-{3-[(2-pyrrolidin-1-yl-ethylamino)-methyl]-isoxazol-5-yl}-1H-quinolin-2-one and pharmaceutically acceptable salts thereof.

The invention also relates to methods of inhibiting protein tyrosine kinase activity in a mammal by administration of a therapeutically effective amount of at least one compound of Formula I or II. A preferred tyrosine kinase is c-fms.

The invention is considered to include the enantionieric, diastereomeric and tautomeric forms of all compounds of Formulae I and II as well as their racemic mixtures. In addition, some of the compounds represented by Formulae I and II may be prodrugs, i.e., derivatives of an acting drug that possess superior delivery capabilities and therapeutic value as compared to the acting drug. Prodrugs are transformed into active drugs by in vivo enzymatic or chemical processes.

I. Definitions

The term "alkyl" refers to both linear and branched chain radicals of up to 12 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "alkenyl" refers to an alkyl group of up to 12 carbon atoms that contains at least one unsaturation; examples include, but are not limited to vinyl and allyl.

The term "cycloalkyl" refers to a saturated or partially unsaturated ring composed of from 3 to 8 carbon atoms. Alkyl substituents may optionally be present on the ring. Examples include cyclopropyl, 1,1-dimethyl cyclobutyl, 1,2,3-trimethylcyclopentyl, cyclohexyl and cyclohexenyl.

The term "heterocyclyl" refers to a nonaromatic (i.e. saturated or partially unsaturated) ring composed of from 3 to 7 carbon atoms and at least one heteroatom selected from N, O or S. Alkyl substituents may optionally be present on the ring. Examples include tetrahydrofuryl, dihydropyranyl, piperidyl, 2,5-dimethypiperidyl, morpholinyl, piperazinyl, thiomorpholinyl, pyrrolidinyl, pyrrolinyl, pyrazolidinyl, pyrazolinyl, imidazolidinyl and imidazolinyl.

The term "heterocyclylalkyl" refers to a $C_{1-6}$ alkyl group containing a heterocyclyl substituent. Examples include dihydropyranylethyl and 2-morpholinylpropyl.

The term "hydroxyalkyl" refers to at least one hydroxyl group bonded to any carbon atom along an alkyl chain.

The term "aminoalkyl" refers to at least one primary or secondary amino group bonded to any carbon atom along an alkyl chain.

The term "alkoxyalkyl" refers to at least one alkoxy group bonded to any carbon atom along an alkyl chain.

The term "polyalkoxyalkyl" refers to long-chain alkoxy compounds and includes polyethylene glycols of discreet or monodispersed sizes.

The term "thioalkyl" refers to at least one sulfur group bonded to any carbon atom along an alkyl chain. The sulfur group may be at any oxidation state and includes sulfoxides, sulfones and sulfates.

The term "carboxyalkyl" refers to at least one carboxylate group bonded to any carbon atom along an alkyl chain. The term "carboxylate group" includes carboxylic acids and alkyl, cycloalkyl, aryl or aralkyl carboxylate esters.

The term "heteroaromatic" or "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroaralkyl" refers to a $C_{1-6}$ alkyl group having a heteroaryl substituent. Examples include furylethyl and 2-quinolinylpropyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and napththalene.

The term "aralkyl" refers to a $C_{1-6}$ alkyl group containing an aryl substituent. Examples include benzyl, phenylethyl or 2-naphthylmethyl.

The term "heteroaralkyl" refers to a $C_{1-6}$ alkyl group containing a heteroaryl substituent. Examples include furylmethyl and pyridylpropyl.

The term "aryloxy" refers to an oxygen atom bound to an aryl substituent. Examples include phenoxy and benzyloxy.

The term "arylalkoxy" refers to an alkoxy group bound to an aryl substituent. Examples include phenylmethyl ether.

The term "acyl" refers to the group —C(O)$R_a$, where $R_a$ is alkyl, aryl, aralkyl, heteroaryl and heteroaralkyl. An "acylating agent" adds the —C(O)$R_a$ group to a molecule.

The term "sulfonyl" refers to the group —S(O)$_2R_a$, where $R_a$ is hydrogen, alkyl, cycloalkyl, haloalkyl, aryl, aralkyl, heteroaryl and heteroaralkyl. A "sulfonylating agent" adds the —S(O)$_2R_a$ group to a molecule.

II. Therapeutic Uses

The compounds of Formulae I and II represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I or II. A preferred tyrosine kinase is c-fms. In one embodiment of inhibiting a protein tyrosine kinase, at least one of the compounds of Formula I or II is combined with a known tyrosine kinase inhibitor.

In various embodiments of the invention, the protein tyrosine kinases inhibited by the compounds of Formulae I and II are located in cells, in a mammal or in vitro. In the case of mammals, which includes humans, a therapeutically effective amount of a pharmaceutically acceptable form of at least one of the compounds of Formula I or II is administered.

The invention further provides methods of treating cancer in mammals, including humans, by administration of a therapeutically effective amount of a pharmaceutically acceptable composition of least one compound of Formula I or II. Exemplary cancers include, but are not limited to, breast cancer, colon cancer, stomach cancer, hairy cell leukemia and non-small lung carcinoma. In one embodiment of the invention, an effective amount of at least one compound of Formula I or II is administered in combination with an effective amount of a chemotherapeutic agent.

The invention also provides methods of treating cardiovascular and inflammatory diseases in mammals, including humans, by administration of a therapeutically effective amount of a pharmaceutically acceptable form of at least one of the compounds of Formula I or II. Example of diseases that may be effectively treated include glomerulonephritis, rheumatoid arthritis, psoriasis, diabetes, tumor related angiogenesis, restenosis, schizophrenia and Alzheimer's dementia.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

The compounds of Formulae I and II may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formulae I and II include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamine salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

III. Methods of Preparation

Exemplary synthetic routes for generating the quinolinones of the invention are described below.

Scheme 1

Scheme 1 illustrates methods of preparation of compounds of formulae I and II. Appropriate functionality of amino-ketones of compounds of formula 1-1 may be introduced to amino-ketones of formula 1-2 prior to formation of the quinolone. In cases where Z is a halogen such as bromine, iodine, or chlorine it may be converted to a cyano group using palladium catalysis cyanation methods or more preferably copper cyanide in DMF at temperatures ranging from 120-180° C. Halogens may also be converted to acetylenes using standard palladium catalyzed coupling methods.

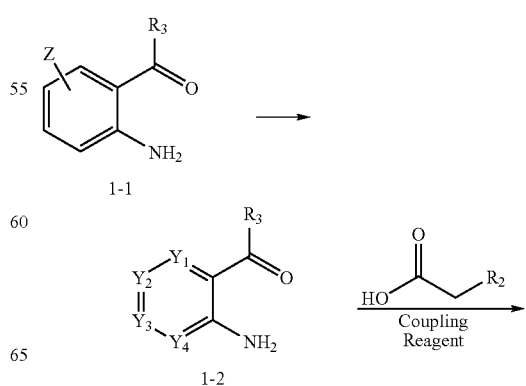

-continued

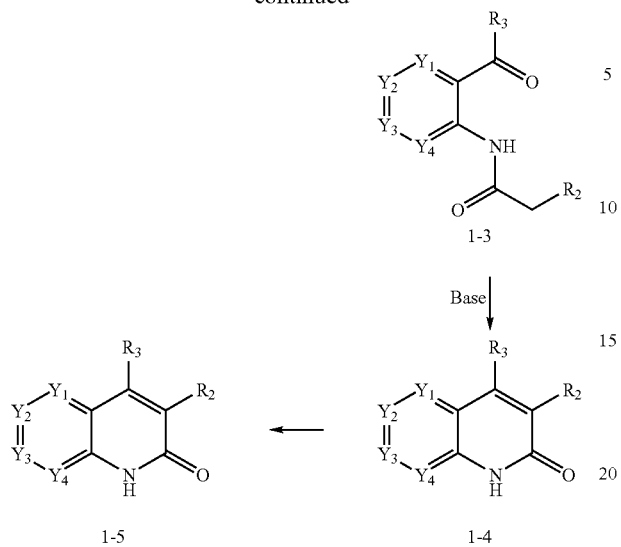

Treatment of an amino-ketone of formula 1-2 with a carboxylic acid in a suitable reaction medium containing a coupling reagent generates an amide of formula 1-3. Suitable coupling reagents include PyBrOP, oxalyl chloride, phosphorus oxychloride, and EDCI with or without an additive such as HOBt or DMAP. The preferable coupling agent is EDCI in DCM or PyBrOP.

Compounds of formula 1-4 are then obtained via base promoted cyclization of compounds of formulla 1-3. Suitable bases are piperidine, DMAP, or NEt₃ in reaction media such as DCM, DMF, or toluene. Preferably the cyclization is conducted in toluene containing piperidine at temperatures ranging from 25° C. to 110° C.

Additionally it is recognized that quinolones of formula 1-4 may be further modified to provide compounds of formula 1-5. Examples include, but are not limited to: when $R_4$ of formula 1-4 is a nitro group it may be reduced to an amino group using standard techniques such as $H_2$ with Pd on carbon, and then the amine reacted with reagents such as carboxylic anhydride or acid chlorides to give compounds of formula 1-5 where $R_4$ is N-acyl; a sulfonyl chloride to give compounds of formula 1-5 where $R_4$ is N-sulfonamide; and aldehydes and ketones in the presence of a reducing agent such as sodium triacetoxyborohydride to give compounds of formula 1-5 where $R_4$ is N-alkyl. When $R_4$ of formula 1-4 is a halide such as a bromo, iodo, or chloro, reactions include Suzuki couplings with boronic acids to give compounds of formula 1-5 where $R_4$ is alkyl, aryl or heteroaryl; palladium-catalyzed cyanation reactions to give compounds of formula 1-5 where $R_4$ is cyano; and when $R_4$ of formula 1-4 is a bromo or iodo, halogen-metal exchange reactions where the quinolone N-H is first deprotonated with an aprotic base such as i-PrMgCl followed by lithium-bromine exchange using n-butyl lithium and quenching with various electrophiles such as dimethyl disulfide to give compounds of formula 1-5 where $R_4$ is S-Me when the electrophile is dimethyl disulfide. When $R_4$ of formula 1-4 is a vinyl alkene, the alkene may be oxidized to the diol (J. Org. Chem. 1992, 57, 2768) and further manipulated by oxidation with sodium periodate to give an aldehyde. The aldehyde may be reacted with amines under reducing conditions to give alkyl amines, or oxidized to the carboxylic acid with sodium chlorite, or reduced to an alcohol with sodium borohydride.

In cases where $R_2$ of formula 1-4 is an amino-heterocycle, such as a 3-amino-isoxazol-5-yl, the amino group may be subjected to the reactions described above for compounds of formula 1-4 when $R_4$ is an amino group to give compounds of formula 1-5 where $R_4$ is a 3-amino-substituted isoxazol-5-yl; and in addition may be reacted with formamides such as N,N-dimethylformamide or amides such as N,N-dimethylacetamide in the presence of methanesulfonyl chloride to give compounds of formula 1-5 where $R_4$ is 3-N-amidino substituted isoxazol-5-yl.

In cases where $R_2$ of compounds of formula 1-4 is a carboxylic acid ester, the ester can be hydrolyzed with HCl in dioxane to give the carboxylic acid derivative which can then be reacted with ethanolamines according to standard procedures to give compounds of formula 1-5 where $R_2$ is a 4- or 5-substituted oxazol-2-yl derivative.

Scheme 2

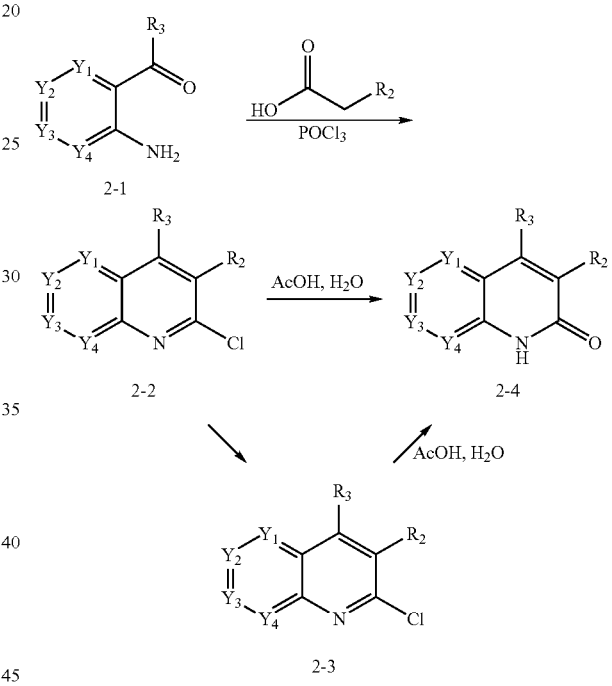

Scheme 2 illustrates alternative methods of preparation of compounds of formulae I and II.

Treatment of an aniline of formula 2-1 with a carboxylic acid in the presence of $POCl_3$ in a suitable reaction medium generates a 2-chloroquinoline of formula 2-2. Suitable reaction media are toluene or DCM or the reaction can be performed in POCl3 without additional solvent. Preferably the reaction is performed in $POCl_3$ at temperatures ranging from 25° C. to 110° C.

Hydrolysis of compounds of formula 2-2 provides compounds of formula 2-4. Suitable reagents include aqueous hydrochloric acid, or acetic acid and water. The preferable reaction condition is acetic acid containing 20% water at 120° C.

Compounds of formula 2-2 may also be modified to provide compounds of formula 2-3. For example, when $R_4$ of formula 2-2 is a nitro group it may be reduced to an amino group using iron and ammonium chloride. The amino group can subsequently be reacted with aryl- or heteroaryl-iodides or bromides using palladium catalyzed coupling procedures to give compounds of formula 2-3 where R$_4$ is N-heteroaryl or N-aryl. Compounds 2-3 may then be hydrolyzed to compounds 2-4 using the methods described for compounds of formula 2-2.

Scheme 3

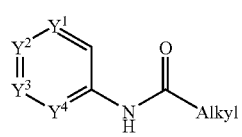

3-1

1. RLi/-78° C.
2. R$^3$L/-78° C. to RT
3. 3N HCl/100° C./16 hr

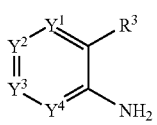

3-2

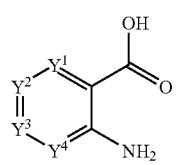

3-3

Alkyl—C(=O)—Cl
base

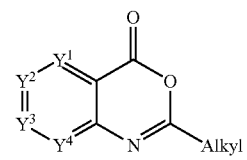

3-4

1. R$^3$—MgCl
2. NaOH

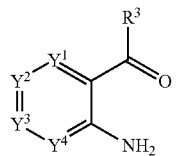

3-5

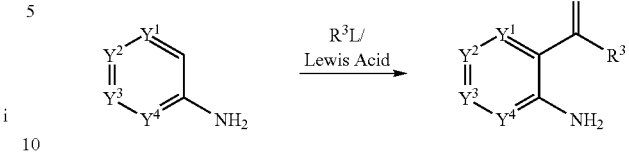

Scheme 3 illustrates different methods for the preparation of ortho amino ketones, which are starting materials for compounds of formulae I and II. Some of these compounds are either commercially available or accessible by known literature methods or can be prepared using the following methods.

In formula i, amine 3-1 is shown with an ortho directing protecting group, such as trimethyl acetyl. Deprotonation with a strong base such as n-BuLi, sec-BuLi or tert-BuLi or metal halogen exchange of a suitably protected substituted or unsubstituted halo aryl amine with suitable organometallic reagent such as BuLi and interception of the resulting organometallic species with R$^3$L such as an acylhalide, acylamide or anhydride introduces an acyl moiety. Where L is understood to be a leaving group such as chloro, or —NMe(OMe). Subsequent deprotection generates ortho amino ketones 3-2; preferred examples of 3-2 have one Y$^{(1-4)}$ as nitrogen.

In formula ii, compounds 3-3 are reacted with acid chlorides such as acetyl chloride or benzoyl chloride in the presence of a base such as pyridine to give 4-oxazinones. Subsequent reaction with Grignard reagents, followed by hydrolysis of the resulting amide with sodium hydroxide gives amino-ketones 3-5.

Formnula iii illustrates synthesis of ortho amino ketones by Friedel-Crafts acylation of aryl or substituted or unsubstituted heteroaryl amines with suitable acylating agents, R$^3$L such as heteroaryl or aryl cyanides, anhydrides and acyl halides in the presence of suitable catalyst such as Lewis acids.

Scheme 4

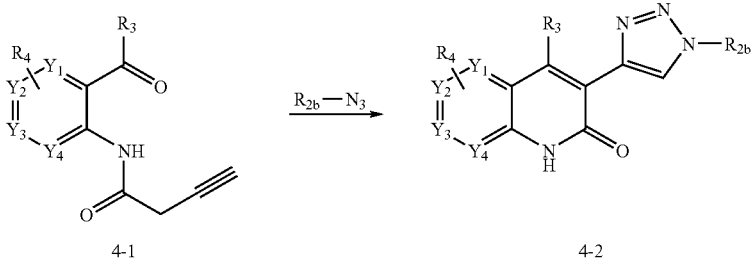

4-1 → 4-2

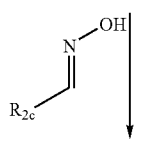

-continued

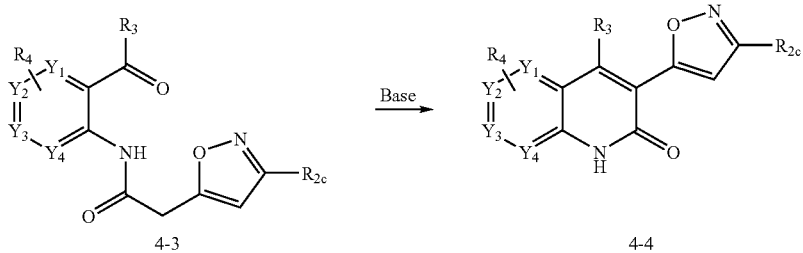

Scheme 4 illustrates the preparation of compounds of formula I and II where $R_2$ is a 1-substituted-triazol-4-yl derivative (4-2) or a 3-substituted-isoxazol-5-yl derivative (4-4).

Treatment of compounds of formula 4-1 with an azide in the presence of sodium ascorbate and copper sulfate in a suitable reaction medium provide compounds of formula 4-2. Suitable reaction media are 50% aqueous t-butanol at temperatures from 50-100° C.

Treatment of compounds of formula 4-1 with oximes in the presence of sodium hypochlorite at 0-25° C. in suitable reaction media such as DCM provide compounds of formula 4-3 that may be cyclized as described in Scheme 1 to provide compounds of formula 4-4.

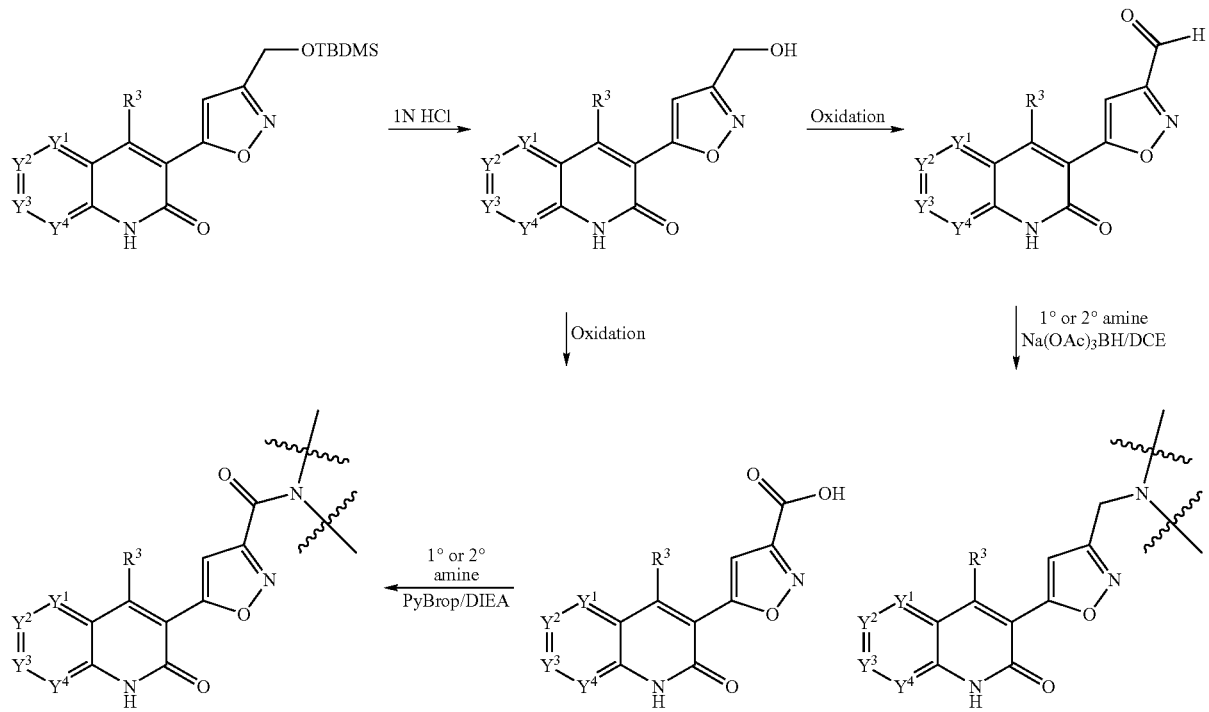

Scheme 5 illustrates the functionalization of heterocyclic moiety at C-3 position. The unmasked hydroxyl functional group can be oxidized with suitable oxidizing agents such as Dess-Martin periodinane, $MnO_2$, PDC, PCC, Swern reagent, or $CrO_3$ to give either an aldehyde or carboxylic acid depending on the reagent of choice. The acids can be reacted, after activation with reagents known to those skilled in the art, with compounds containing primary or secondary amines to obtain the corresponding amides. Aldehydes can be subjected to reductive amination with suitable primary or secondary amines in the presence of a reducing agent, such as sodium triacetoxy borohydride, to introduce substituted amino functionalities.

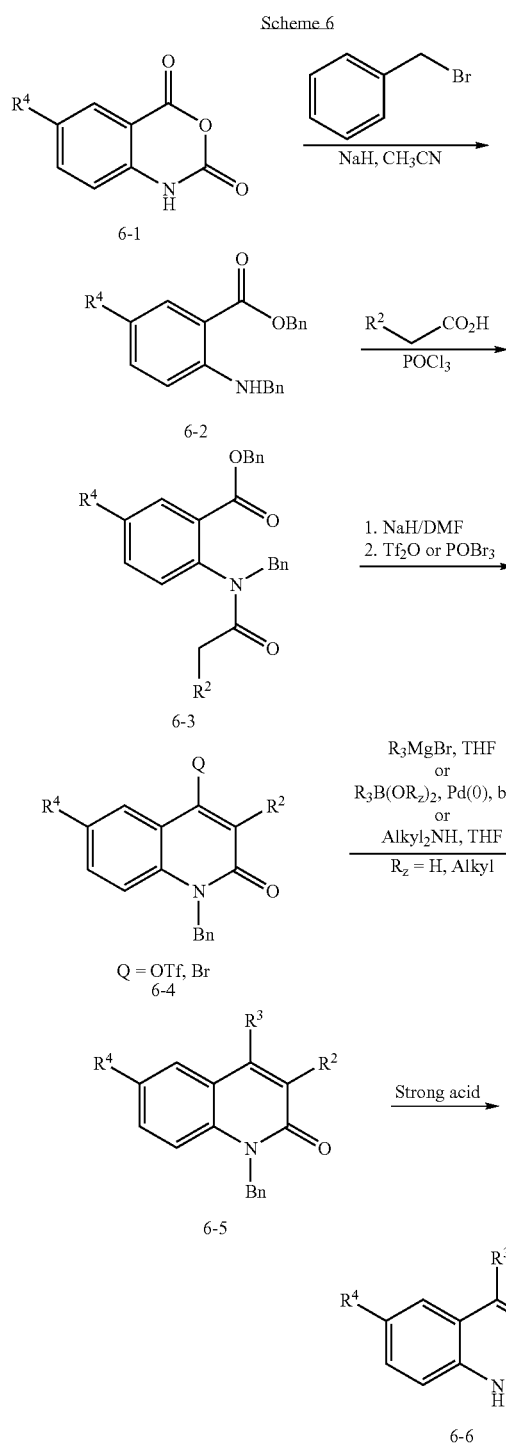

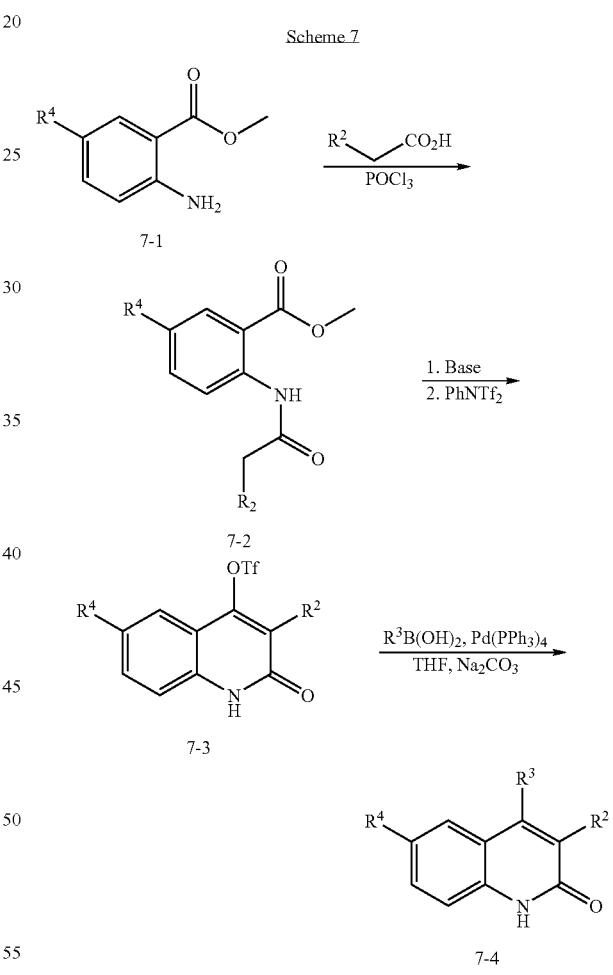

solvent, such as DMF, followed by conversion of the 4-hydroxy group to a triflate or bromide, using appropriate reagents, such as either triflic anhydride or POBr$_3$ to afford compound 6-4. Suzuki reaction with a boronic acid or boronic ester, such as phenylboronic acid or 4-(4,4,5,5-tetramethyl-1,3,2-dioxaborolan-2-yl)benzonitrile, in the presence of a palladium catalyst such as Pd(PPh$_3$)$_4$ and appropriate base, such as Na$_2$CO$_3$ gives the compound 6-5. Alternatively, the triflate group or bromide group in compound 6-4 can be replaced by an nucleophilic agent, for example dicyclohexylcuprate magnesium chloride, to form compound 6-5. Compound 6-4 can also react with an amine such as piperidine in an organic solvent, such as tetrahydrofuran, to form compound 6-5. The protecting group in compound 6-5, such as benzyl group, is removed under strong acid conditions, for example using methanesulfonic acid to give compound 6-6.

Scheme 6 illustrates a general procedure for the synthesis of quinolones with diversity at position 4. Compound 6-1 is reacted with two equivalents of alkylhalide, for example benzyl bromide, in an organic solvent, such as acetonitrile, in the presence of a base, such as NaH to afford compound 6-2. The amino group in compound 6-2 is coupled with an acylating agent, such as (3-methyl-isoxazol-5-yl)-acetic acid, in the presence of POCl$_3$ to form the product 6-3. Cyclization is effected with a base such as NaH in an aprotic Scheme 7 illustrates how a Suzuki reaction can introduce position 4 substituents onto less heavily protected quinolones. Compound 7-1 is treated with an acylating agent, such as (3-methyl-isoxazol-5-yl)-acetic acid, in the presence of a coupling reagent, such as POCl$_3$ to form product 7-2. Cyclization with a base such as t-BuOK in an aprotic solvent, such as DMSO is followed by reaction with a triflating agent such as N-phenyltrifluoromethanesulfonimide to afford a compound 7-3. Suzuki reaction with a boronic acid, such as phenylboronic acid, in the presence of a palladium catalyst such as Pd(PPh$_3$)$_4$ and an appropriate base, such as Na$_2$CO$_3$, gives compound 7-4.

EXAMPLE 1

General Procedure for Quinolone and Napthyridinone Synthesis by Cyclo Condensation To a mixture of substituted acetic acid (1 mmol) and aminoketone (1 mmol), POCl$_3$ (3 mL) was added. The resulting mixture was heated at 70° C. under N$_2$ for 12 hr. POCl$_3$ was removed and the residue was dried in vacuo for 1 hr. The. residue was then dissolved in HOAc (98% acid, 2% water)(2 mL) and NH$_4$Ac (77 mg, 1 mmol) was added and heated at 90° C. for 3 hr. The reaction mixture was cooled to RT and HOAc was removed. The resulting residue was purified on silica with appropriate solvent system.

EXAMPLE 2

General Procedure for Quinolone and Napthyridinone Synthesis by Cyclo Condensation To a mixture of 2-substituted acetic acid (1.5 mmol) and aminoketone (1 mmol), DIEA (0.7 mL, 4 mmol) in THF (10 mL), PyBrop (730 mg, 1.5 mmol) was added. The resulting mixture was stirred at RT overnight. If the LC/MS and/or TLC of the reaction mixture indicated the complete formation of expected fully cyclized product, solvents were removed and the product was isolated by chromatography on silica with appropriate solvent system. If incomplete cyclization was detected, toluene (10 mL) and piperidine (1 mL) was added to the reaction mixture and the resulting mixture was heated at 70° C. until the complete formation of expected quinolone was observed by LC/MS. Solvents were then removed and the product was isolated in usual manner.

EXAMPLE 3

3-(3-Methyl-isoxazol-5-yl)-4-phenyl-1H-[1,5]naphthyridin-2-one

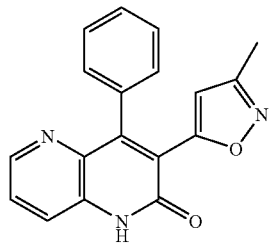

EXAMPLE 3a (3-Amino-pyridin-2-yl)-phenyl-methanone

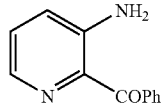

To a solution of 3-amino-2-bromopyridine (860 mg, 5 mmol) in CH$_2$Cl$_2$ (10 mL) and Et$_3$N (0.86 mL, 6.2 mmol), trimethyl acetyl chloride (0.67 mL, 5.5 mmol) was added dropwise under N$_2$ at 0° C. The reaction mixture was allowed to warm to room temperature and stirred for 12 hr and poured in to water (10 mL). The organic layer was separated, dried over Na$_2$SO$_4$ and concentrated. The residue was purified on silica (20% EtOAc/hexanes). Yield 88%; $^1$H-NMR (CDCl$_3$; 400 MHz) δ 8.72 (dd, J$_1$=8.16, J$_2$=1.8 Hz, 1H), 8.1 (brs, 2H), 7.22 (dd, J$_1$=8.16, J$_2$=4.6 Hz, 1H), 1.38 (s, 9H).

To a solution of above compound (2.5 g, 10 mmol) in THF (40 mL) at −78° C., BuLi (10 mL, 25 mmol, 2.5M solution) was added. The resulting mixture was stirred at −78° C. for 1 hr and a solution of N-methoxy-N-methyl-benzamide (2.47 g, 15 mmol) in THF (10 mL) was added dropwise. The reaction mixture was allowed to warm to room temperature and stirred overnight and poured in to ice water (50 mL) and extracted with CH$_2$Cl$_2$ (3×20 mL). The combined organic layers were dried over Na$_2$SO$_4$ and concentrated in vacuo. The residue obtained was dissolved in 3N aq. HCl (20 mL) and MeOH (10 mL). The resulting mixture was heated at 100° C. for 16 hr and allowed to cool to room temperature and neutralized with std. aq. NaHCO$_3$. The product precipitated was collected by suction filtration and purified on silica (20% EtOAc:bexanes).Yield 39%. $^1$H-NMR (CDCl$_3$; 400 MHz) δ 8.04 (dd, J$_1$=4.16, J$_2$=1.44 Hz, 1H),7.93 (m, 2H), 7.3-7.6 (m, 3H), 7.23 (m, 1H), 7.17 (d, J=4.1 Hz, 1H), 6.1 (brs, 2H).

The title compound was prepared from (3-methyl-isoxazol-5-yl)-acetic acid and (3-amino-pyridin-2-yl)-phenyl-methanone (Example 3a) according to general procedure 1; Yield 48%.

EXAMPLE 4

3-(3-Methyl-isoxazol-5-yl)-4-phenyl-1H-[1,6]naphthyridin-2-one

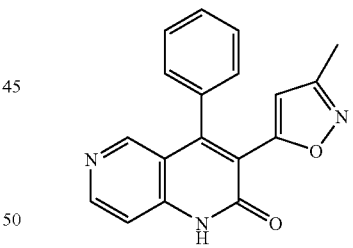

EXAMPLE 4a (4-Amino-pyridin-3-yl)-phenyl-methanone

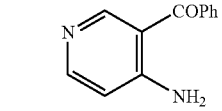

Prepared from 2,2-dimethyl-N-(4-pyridinyl)propanamide and N-methoxy-N-methyl-benzamide according to procedure 6a. $^1$H-NMR (CDCl$_3$; 400 MHz) δ 8.59 (s, 1H), 8.23 (d, J=5.84 Hz, 1H), 7.70-7.26 (m, 5H), 6.4-6.5 (brs, 2H), 6.61 (d, J=5.84 Hz, 1H).

The title compound was prepared from (3-methyl-isoxazol-5-yl)-acetic acid and (4-amino-pyridin-3-yl)-phenyl-methanone (example 4a) according to procedure 1; Yield 59%.

EXAMPLE 5

6-Chloro-3-(3-methyl-isoxazol-5-yl)-4-phenyl-1H-[1,8]naphthyridin-2-one

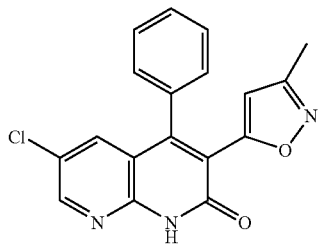

EXAMPLE 5a (2-Amino-5-chloro-pyridin-3-yl)-phenyl-methanone

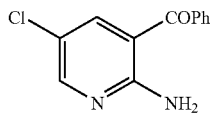

Prepared by reacting lithiated 2,2-dimethyl-N-(5-chloro-pyridin-2-yl)propanamide (as described in the literature; J. Org. Chem., 48(20), 3401-8, 1983) with N-methoxy-N-methyl-benzamide followed by the acid catalyzed deprotection as described in the previous example. Yield 54%. δ 8.20 (d, J=2.44 Hz, 1H), 7.86 (d, J=2.44 Hz, 1H), 7.4-7.6 (m, 5H), 6.80 (brs, 2H).

The title compound was prepared from (3-methyl-isoxazol-5-yl)-acetic acid and (2-amino-5-chloro-pyridin-3-yl)-phenyl-methanone (example 5a) according to procedure 1; Yield 56%.

EXAMPLE 6

3-(3-Methyl-isoxazol-5-yl)-4-phenyl-1H-[1,8naphthyridin]-2-one

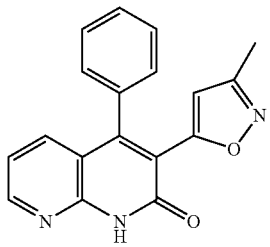

EXAMPLE 6a (2-Amino-pyridin-3-yl)-phenyl-methanone

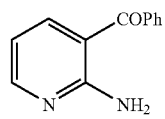

To a solution of 2,2-dimethyl-N-(2-pyridinyl)propanamide (1.78 g, 10.00 mmol) at −78° C. under N$_2$ was added BuLi (10.0 mL, 25 mmol, 2.5M in hexane). The resulting mixture was allowed to warm to 0° C. and stirred for 4 h. A solution of N-methoxy-N-methyl-benzamide (2.47 g, 15 mmol) in THF (10 mL) was then added drop wise. The reaction mixture was allowed to warm to RT and stirred overnight and poured in to ice water (50 mL) and extracted with CH$_2$Cl$_2$ (3×20 mL). The combined organic layers were dried over Na$_2$SO$_4$ and concentrated in vacuo. The residue obtained was dissolved in 3N aq. HCl (20 mL) and MeOH (10 mL) and heated at 100° C. for 16 hr. The reaction mixture was allowed to cool to room temperature and neutralized with std. aq. NaHCO$_3$. The product precipitated was collected by suction filtration and purified on silica (20% EtOAc:hexane). Yield 53%. $^1$H-NMR (CDCl$_3$; 400 MHz) δ 8.26(dd, J$_1$=4.76, J$_2$=1.88 Hz, 1H), 7.79(dd, J$_1$=7.80, J$_2$=1.88 Hz, 1H), 7.78-7.28 (m, 5H), 6.86 (brs, 2H), 6.62 (dd, J$_1$=8.24, J$_2$=4.76 Hz, 1H).

The title compound was made from (3-methyl-isoxazol-5-yl)-acetic acid and (2-amino-pyridin-3-yl)-phenyl-methanone (example 6a) according to procedure 1; Yield 67%.

EXAMPLE 7

3-(3-Methyl-isoxazol-5-yl)-4-phenyl-1H-[1,7]naphthyridin-2-one

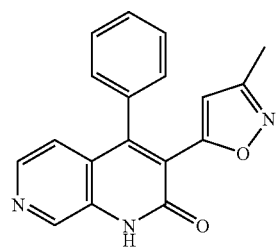

EXAMPLE 7a (3-Amino-pyridin-4-yl)-phenyl-methanone

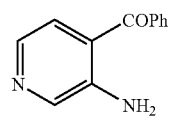

As described in previous example the title compound was prepared from 2,2-dimethyl-N-(3-pyridinyl)propanamide and N-methoxy-N-methyl-benzamide. $^1$H-NMR (CDCl$_3$; 400 MHz) 8 8.29 (s,1H), 7.93 (d, J=5.18 Hz,1H), 7.40-7.62 (m, 5H), 7.23 (d, J=5.18 Hz, 1H), 5.83(brs, 2H).

The title compound was prepared from (3-methyl-isoxazol-5-yl)-acetic acid and (3-amino-pyridin-4-yl)-phenyl-methanone (example 7a) according to procedure 1; Yield 66%.

EXAMPLE 8

6-Bromo-3-(3-Methyl-isoxazol-5-yl)-4-phenyl-1H-[1,8]naphthyridin-2-one

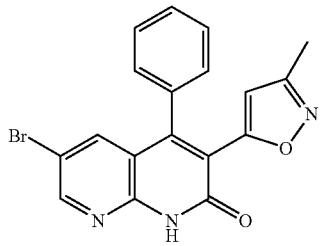

EXAMPLE 8a (2-Amino-5-bromo-pyridin-3-yl)-phenyl-methanone

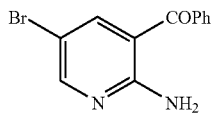

To a solution of (2-amino-pyridin-3-yl)-phenyl-methanone (example 6a)(198.2 mg,1 mmol) in $CH_3CN$ (2 mL) under $N_2$ was added NBS (195 mg, 1.1 mmol). The resulting solution was stirred at room temperature for 12 hr and concentrated. The residue was dissolved in $CH_2Cl_2$ and washed with water (10 mL), aq. $NaHCO_3$ and aq. 10% $Na_2S_2O_3$ (10 mL). The organic layer was separated, dried ($Na_2SO_4$) and concentrated. The residue was then purified on silica (20% EtOAc: hexanes). Yield 43%: $^1$H-NMR ($CDCl_3$; 400 MHz) δ 8.27 (d, J=2.44 Hz, 1H), 7.84 (d, J=2.44 Hz, 1H), 7.4-7.6 (m, 5H), 6.87 (brs, 2H).

The title compound was prepared from (3-methyl-isoxazol-5-yl)-acetic acid and (2-amino-5-bromo-pyridin-3-yl)-phenyl-methanone (example 8a) according to procedure 1. Yield 29%.

EXAMPLE 9

6-Chloro-3-(3-methyl-isoxazol-5-yl)-4-phenyl-1H-[1,7]naphthyridin-2-one

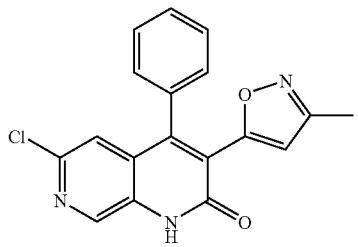

EXAMPLE 9a (5-Amino-2-chloro-pyridin-4-yl)-phenyl-methanone

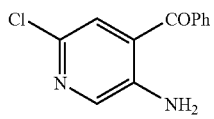

Prepared (as described in previous example) by reacting lithiated 2,2-dimethyl—N-(6-chloropyridin-3-yl)propana- mide (as described in J. Org. Chem., 55(15), 4744, 1990) with N-methoxy-N-methyl-benzamide followed by the acid catalyzed deprotection. Yield 44%. $^1$H-NMR ($CDCl_3$; 400 MHz) δ 8.08 (s, 1H), 7.70-7.26 (m, 5H), 7.29 (s, 1H), 5.9 (brs, 2H).

The title compound was prepared from (3-methyl-isoxazol-5-yl)-acetic acid and (5-amino-2-chloro-pyridin-4-yl)-phenyl-methanone (example 9a), according to the procedure for example 2, yield 71%.

EXAMPLE 10

6-Chloro-3-(3-methyl-benzo[b]thiophen-2-yl)-4-phenyl-1H-quinolin-2-one

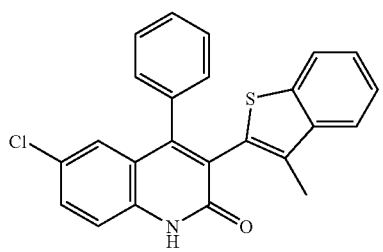

from benzo[b]thiophen-2-yl acetic acid and (2-amino-5-chloro-phenyl)-phenyl-methanone according to general procedure 2. Yield 38%.

EXAMPLE 11

6-Chloro-4-phenyl-3-thiophen-2-yl-1H-quinolin-2-one

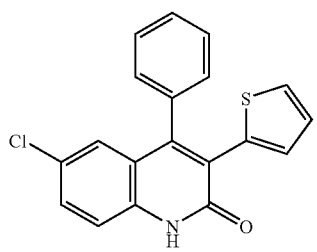

from thiophen-2-yl acetic acid and (2-amino-5-chloro-phenyl)-phenyl-methanone according to general procedure 2. Yield 55%.

EXAMPLE 12

6-Chloro-4-phenyl-3-(1H-pyrrol)-2-yl-1H-quinolin-2-one

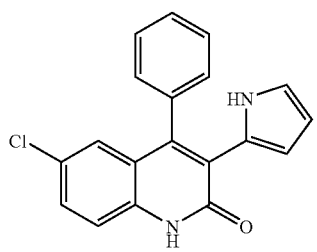

from pyrrol-2-yl, acetic acid (Synthetic Communications, 19,(13-14), 2585, 1989) and (2-amino-5-chloro-phenyl)-phenyl-methanone according to general procedure 2. Yield 12%.

EXAMPLE 13

6-Chloro-4-phenyl-3-pyrazol-1-yl-1H-quinolin-2-one

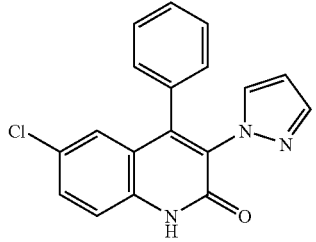

from 2-(1H-pyrazol-1-yl) acetic acid and (2-amino-5-chloro-phenyl)-phenyl-methanone according to general procedure 2. Yield 49%.

EXAMPLE 14

6-Chloro-3,4-diphenyl-1H-quinolin-2-one

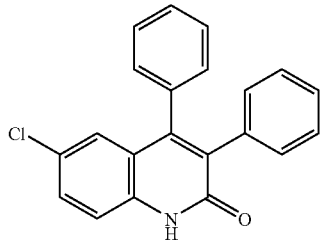

from phenylacetic acid and (2-amino-5-chloro-phenyl)-phenyl-methanone according to general procedure 2. Yield 53%.

EXAMPLE 15

6-Chloro-3-[(5-morpholine-4-carbonyl)1H-pyrrol-2-yl]-4-phenyl-1H-quinolin-2-one

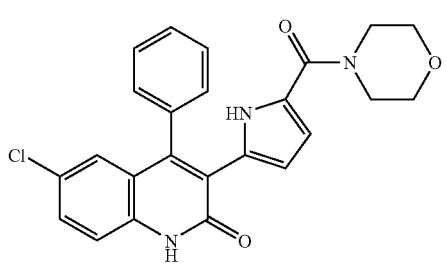

EXAMPLE 15a

[5-(Morpholine-4-carbonyl)-1H-pyrrol-2-yl]-acetic acid

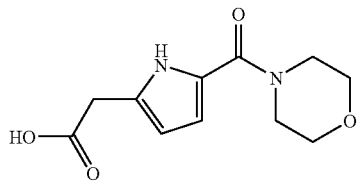

Triphosgene (1.64 g, 5.5 mmol) was added to (1H-pyrrol-2-yl)-acetic acid ethylester (prepared following the general procedure described in; J. Org. Chem., 59(18),5230-5234, 1994) (841.0 mg, 5.5 mmol) in toluene (50 mL). The reslting mixture was heated at 100° C. for 1 hr. The reaction mixture was allowed to cool to RT and morpholine (1 mL) and Et$_3$N (1 mL) was added. The resulting mixture was stirred at RT overnigbht and concentrated. The residue obtained was chromatographed on silica (50-100% EtOAc:Hexane) to obtain [5-(Morpholine-4-carbonyl)-1H-pyrrol-2-yl-acetic acid ethyl ester. Yield 43%. $^1$H-NMR (CDCl$_3$; 400 MHz) δ 10.46 (brs, 1H), 6.43 and 6.08 (dd, J$_1$=3.6, J$_2$=2.68, 1H each), 4.1 (q, J=7.16, 2H), 3.85 and 3.73 (m, 4H each), 3.67 (s, 2H), 1.25 (t, J=7.16, 3H).

The above compound (266 mg, 1 mmol) was dissolved in MeOH (5 mL). To this solution IN NaOH (3 mL) was added. The resulting mixture was stirred at RT overnight and MeOH was removed in vacuo. Water (10 mL) was then added and the reaction mixture was acidified with HOAc. The product was extracted with 5% MeOH: CH$_2$Cl$_2$ (5×10 mL). The organic layers were combined and dried (Na$_2$SO$_4$) and concentrated to obtain [5-(morpholine-4-carbonyl)-1H-pyrrol-2-yl]-acetic acid. Yield 73%. δ 11.28 (brs, 1H), 6.42 and 5.95 (dd, J$_1$=3.3, J$_2$=2.48, 1H each), 3.69 and 3.61 (m, 4H each), 3.60 (s, 2H).

The title compound was prepared from [5-(morpholine-4-carbonyl)-1H-pyrrol-2-yl]-acetic acid (example 15a) and (2-amino-5-chloro-phenyl)-phenyl-methanone according to general procedure 2. Yield 41%.

EXAMPLE 16

6-Chloro-3-(5-methyl-2H-pyrazol-3-yl)-4-phenyl-1H-quinolin-2-one

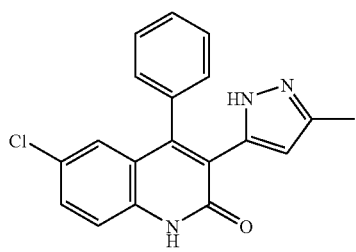

Synthesized from 5-methyl-2H-pyrazol-3-yl-acetic acid and (2-amino-5-chloro-phenyl)-phenyl-methanone according to general procedure 2. Yield 23%.

EXAMPLE 17

3-(1-Benzyl-1H-imidazol-2-yl)-6-Chloro-4-phenyl-1H-quinolin-2-one

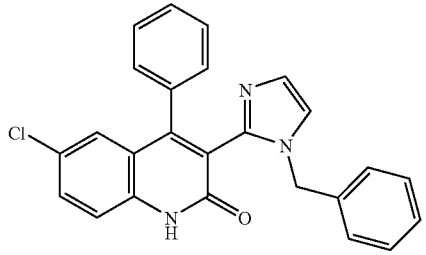

Synthesized from (1-benzyl-1H-imidazol-2-yl)-acetic acid (Tetrahedron Letters, 37 (51), 9259, 1996) and (2-amino-5-chloro-phenyl)-phenyl-methanone according to general procedure 2. Yield 43%.

EXAMPLE 18

6-Chloro-3-(5-methyl-isoxazol-3-yl)-4-phenyl-1H-quinolin-2-one

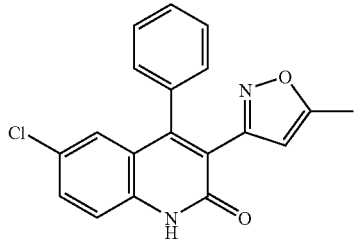

Synthesized from (5-methyl-isoxazol-3-yl)-acetic acid (J. Med. Chem., 34(2), 518, 1991) and (2-amino-5-chlorophenyl)-phenyl-methanone according to general procedure 2. Yield 69%.

EXAMPLE 19

6-Chloro-4-phenyl-3-pyridin-2-yl-1H-quinolin-2-one

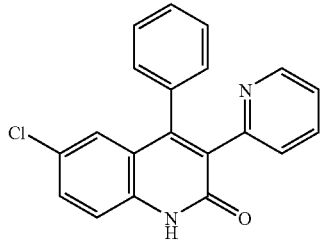

Synthesized from (2-pyridyl)-acetic acid and (2-amino-5-chloro-phenyl)-phenyl-methanone according to general procedure 2 Yield 23%.

EXAMPLE 20

4-(4-Ethyl-phenyl)-3-(2-methyl-thiazol-4-yl)-2-oxo-1,2-dihydro-quinoline-6-carbonitrile

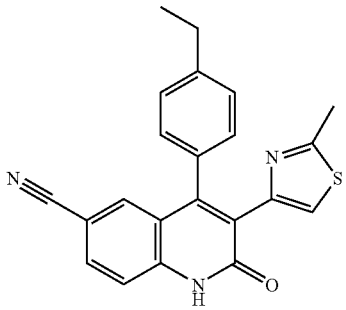

Synthesized from (2-methyl-thiazol-4-yl)-acetic acid and 4-Amino-3-(4-ethyl-benzoyl)-benzonitrile according to general procedure 2. Yield 27%.

EXAMPLE 21

6-Chloro-3-(3-hydroxymethyl-isoxazol-5-yl)-4-phenyl-1H-quinolin-2-one

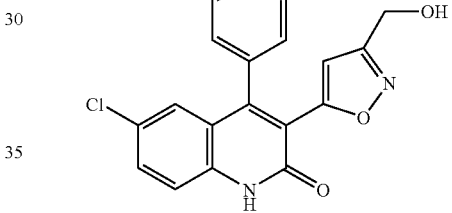

EXAMPLE 21a

Preparation of [3-(tert-Butyl-dimethylsilanyloxymethyl)-isoxazol-5-yl]-acetic acid

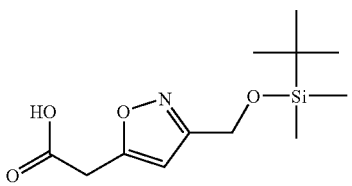

A solution of 3-(tert-butyl-dimethylsilanyloxymethyl)-5-methyl-isoxzole (US 5464848) (13 g, 57 mmol) and TMEDA (1.2 mL, 7.9 mmol) in THF (150 mL) was cooled to −78° C. and BuLi (25 mL, 62.6 mmol, 2.5M solution) was added in 5 min. The resulting mixture was stirred at −78° C. for 45 min. and $CO_2$ (g) was bubbled in to the reaction mixture until orange color disappeared. The reaction mixture was stirred at −78° C. for another 30 min. and std. $NH_4Cl$ (10 mL) followed by water (25 mL) were added. The reaction mixture was allowed to warm to RT and extracted with $CH_2Cl_2$ (5×20 mL). The combined organiclayers were dried over $Na_2SO_4$ and concentrated. The residue obtained was dried in vacuo to obtain [3-(tert-butyl-dimethylsilanyloxymethyl)-isoxazol-5-yl]-acetic acid and directly used in next step without purification. Yield 68%. 8 4.77 (s, 2H), 3.89 (s, 2H), 0.92 (s, 9H).

EXAMPLE 21b

3-[3-(tert-Butyl-dimethyl-silanyloxymethyl)-isoxazol-5-yl]-6-chloro-4-phenyl-1H-quinolin-2-one

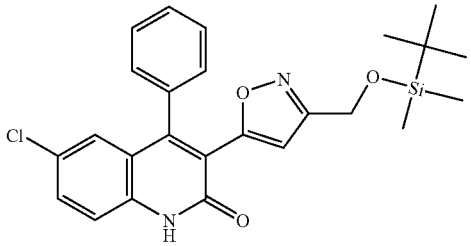

Prepared from [3-(tert-butyl-dimethylsilanyloxymethyl)-isoxazol-5-yl]-acetic acid (example 21a) and (2-amino-5-chloro-phenyl)-phenyl-methanone as described above) in THF (80 mL).

Treatment of the resulting mixture with 1 N HCl (10 mL) was followed by stirring at RT (12 hr) and concentration. The residue obtained was triturated with ether (3×50 mL) and dried in vacuo to obtain the title compound according to general procedure 2. Yield 43%.

EXAMPLE 22

5-(6-Chloro-2-oxo-4-phenyl-1,2-dihydro-quinolin-3-yl)-isoxazole-3-carboxylic acid

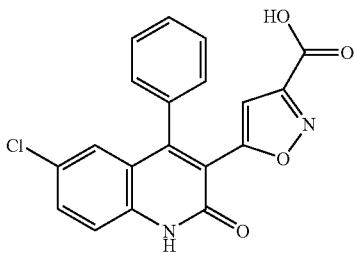

To a solution of 6-chloro-3-(3-hydroxymethyl-isoxazol-5-yl)-4-phenyl-1H-quinolin-2-one (example 21) (353 mg, 1 mmol) in HOAc (1 mL), CrO$_3$ (100 mg, 1 mmol) was added. The resulting mixture was stirred at 50° C. for 3 h. The reaction mixture was allowed to cool to RT and HOAc was removed. The residue was subjected to reversed phase HPLC to obtain the title compound. Yield 21%.

EXAMPLE 23

6-Chloro-3-[(3-morpholine-4-carbonyl)isoxazol-5-yl]-4-phenyl-1-quinolin-2-one

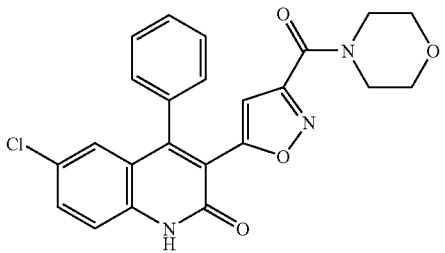

To a solution 5-(6-chloro-2-oxo-4-phenyl-1,2-dihydro-quinolin-3-yl)-isoxazole-3-carboxylic acid (example 22) (36.7 mg, 0.1 mmol), morpholine (13 μL, 0.15 mmol) in DMF (1 mL) was added PyBrop (73 mg, 0.15 mmol) and DIEA (70 μL). The resulting mixture was stirred at RT overnight and concentrated. The residue obtained was purified on silica (0-5% MeOH: EtOAc) to obtain the title compound. Yield 41%.

EXAMPLE 24

General procedure for elaboration of R$^2$

To a solution of 6-chloro-3-(3-hydroxymethyl-isoxazol-5-yl)-4-phenyl-1H-quinolin-2-one (822 mg, 2.33 mmol) in CH$_3$CN (8 mL), Dess-Martin periodinane (1.05 g, 2.47 mmol) was added. The resulting mixture was stirred at RT for 3 hr and concentrated. Water (20 mL) was then added and the product was extracted with (5% MeOH: CH$_2$Cl$_2$ 3×50 mL). The organic layer was dried (Na$_2$SO$_4$) and concentrated. The residue was chromatographed on silica (30-80% EtOAc:Hexane) to obtain partially pure 5-(6-chloro-2-oxo-4-phenyl-1,2-dihydro-quinolin-3-yl)-isoxazole-3-carboxaldehyde. Yield 66%: $^1$H-NMR (CDCl$_3$; 400 MHz) δ 13.15 (s,1H), 10.09 (s, 1H), 7.57-7.47 (m, 8H), 6.97 (s,1H).

To a solution of above aldehyde (35.1 mg, 0.1 mmol) and corresponding amine (0.1 mmol) in dichloroethane (1 mL) was added HOAc (6 μL). The resulting mixture was stirred at RT for 30 min. and Na(OAc)$_3$BH (31.6 mg, 0.15 mmol) was added and stirred at RT for 12 hr and concentrated. The residue obtained was dissolved in MeOH (0.5 mL), filtered and purified by reversed phase HPLC using CH$_3$CN: 0.1% TFA/water to obtain the expected product as its TFA salt.

EXAMPLE 25

6-Chloro-3-[3-(4-methyl-piperazin-1-ylmethyl)-isoxazol-5-yl]-4-phenyl-1H-quinolin-2-one

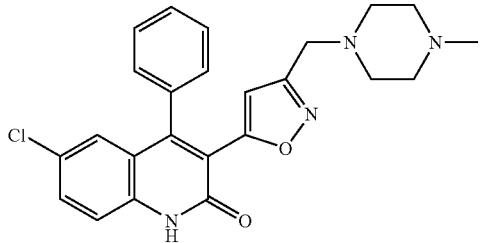

From 5-(6-chloro-2-oxo-4-phenyl-1,2-dihydro-quinolin-3-yl)-isoxazole-3-carboxaldehyde and 1-methyl-piperazine according to procedure 24. Yield 71%.

EXAMPLE 26

6-Chloro-4-phenyl 3-{3-[(2-piperidin-1-yl-ethylamino)-methyl]-isoxazol-5-yl}-1H-quinolin-2-one

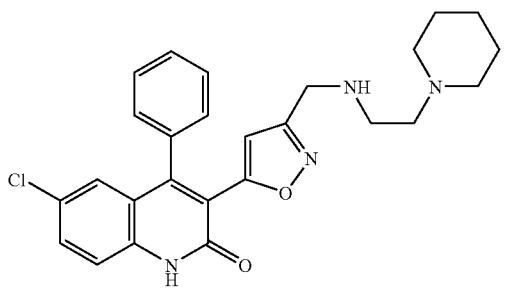

From 5-(6-chloro-2-oxo-4-phenyl-1,2-dibydro-quinolin-3-yl)-isoxazole-3-carboxaldehyde and 2-piperidin-1-yl-ethylamine according to procedure 24. Yield 53%.

EXAMPLE 27

2-{[5-(6-Chloro-2-oxo-4-phenyl-1,2-dihydro-quinolin-3-yl)-isoxazol-3-ylmethyl]-amino}-malonic acid dimethyl ester

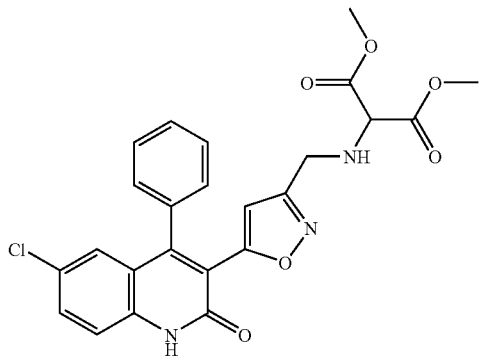

From 5-(6-chloro-2-oxo-4-phenyl-1,2-dibydro-quinolin-3-yl)-isoxazole-3-carboxaldebyde and 3-amino-pentanedioic acid dimethyl ester according to procedure 24. Yield 27%.

EXAMPLE 28

6-Chloro-4-phenyl-3-{3-[(2-pyrrolidin-1-yl-ethylamino)-methyl]-isoxazol-5-yl}-1H-quinolin-2-one

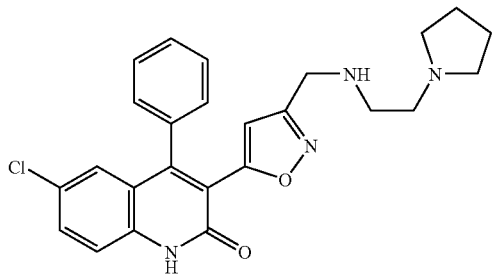

From 5-(6-chloro-2-oxo-4-phenyl-1,2-dihydro-quinolin-3-yl)-isoxazole-3-carboxaldehyde and 2-pyrrolidin-1-yl-ethylamine according to procedure 24. Yield 53%.

EXAMPLE 29

6-Chloro-3-{3-[(2-morpholin-4-yl-ethylamino)-methyl]-isoxazol-5-yl}-4-phenyl-1H-quinolin-2-one

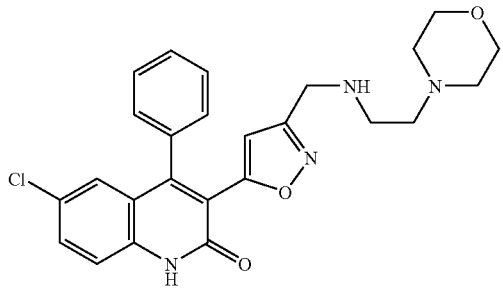

From 5-(6-chloro-2-oxo-4-phenyl-1,2-dihydro-quinolin-3-yl)-isoxazole-3-carboxaldehyde and 2-morpholin-4-yl-ethylamine according to procedure 24. Yield 37%.

EXAMPLE 30

6-Chloro-4-phenyl-3-[3-(4-pyridin-2-yl-piperazin-1-ylmethyl)-isoxazol-5-yl]-1H-quinolin-2-one

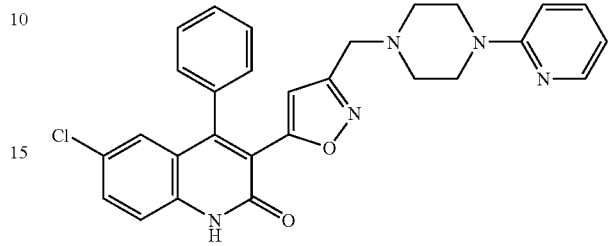

From 5-(6-chloro-2-oxo-4-phenyl-1,2-dihydro-quinolin-3-yl)-isoxazole-3-carboxaldehyde and 1-pyridin-2-yl-piperazine according to procedure 24. Yield 32%.

EXAMPLE 31

4-{[5-(6-Chloro-2-oxo-4-phenyl-1,2-dihydro-quinolin-3-yl)-isoxazol-3-ylmethyl]-amino}-methyl)-benzene sulfonamide

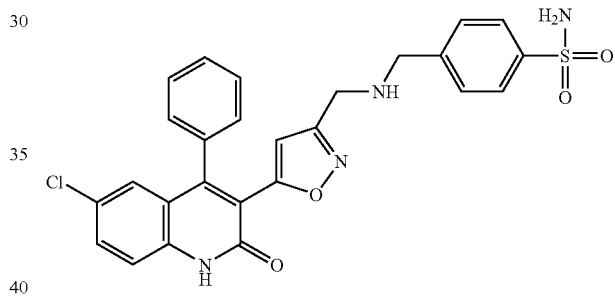

From 5-(6-chloro-2-oxo-4-phenyl-1,2-dihydro-quinolin-3-yl)-isoxazole-3-carboxaldehyde and 4-aminomethylbenzenesulfonamide according to procedure 24. Yield 44%.

EXAMPLE 32

5-(6-Chloro-2-oxo-4-phenyl-1,2-dihydro-quinolin-3-yl)-isoxazole-3-carbonitrile

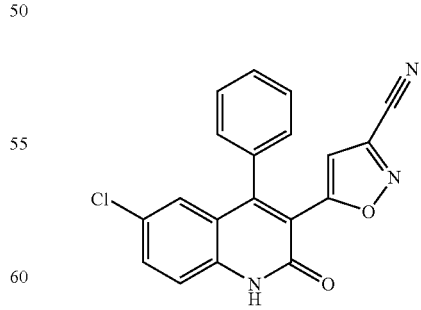

To a solution of 5-(6-chloro-2-oxo-4-phenyl-1,2-dihydro-quinolin-3-yl)-isoxazole-3-carboxaldehyde in MeOH (20 mL), aq. NH$_2$OH (1 mmol) was added. The resulting mixture was stirred at RT for 2 hr. The reaction mixture was concentrated and water (20 mL) was added. The precipitate formed was then collected by suction filtration and dried in vacuo. Above oxime (365 mg, 1 mmol) was dissolved in pyridine (10 mL) and acetic anhydride (0.3 mL, 2 mmol) was added. The resulting mixture was stirred overnight and concentrated. The residue obtained was purified with (30% EtOAc:Hexane) to obtain the title compound. Yield 67%.

EXAMPLE 33

Preparation of 6-Chloro-3-(1H-imidazol-2-yl)4-phenyl-1H-quinolin-2-one

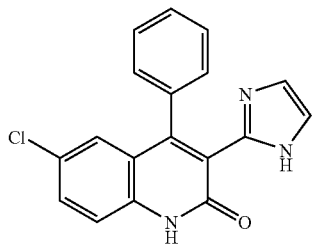

A solution of 3-(1-benzyl-1H-imidazol-2-yl)-6-chloro-4-phenyl-1H-quinolin-2-one (110 mg) in α-chloroethylchloroformate (5 mL) was heated at 100° C. for 2 hr. The reaction was evaporated and the resulting residue was dried in vacuo. The residue was dissolved in HOAc (5 mL) and NH$_4$Ac (100 mg) was added. The reaction mixture was heated at 100° C. for 12 hr. Solvents were removed and the title compound was isolated by reversed phase HPLC. Yield 66%.

EXAMPLE 34

3-(5-bromo-pyridin-3-yl)-6-chloro-4-phenyl-1H-quinolin-2-one

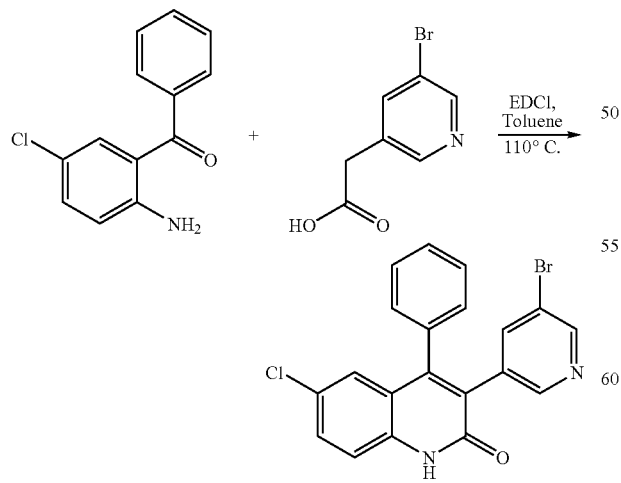

A solution of 2-amino-5-chlorobenzophenone (230 mg, 1.00 mmol), 5-bromo-3-pyridineacetic acid (215 mg, 1.00 mmol) and 1-[3-(dimethylamino)propyl]-3-ethylcarbodiimide hydrochloride (EDCI) (230 mg; 1.20 mmol) in DCM (2.5 mL) was stirred overnight at room temperature. Toluene (2.5 mL) and piperidine (0.2 mL) were then added and the resulting solution was heated to approximately 100° C., allowing the DCM to evaporate from the reaction mixture. After 2 h, the reaction was allowed to cool and stirring was continued at room temperature overnight. The precipitate that formed was filtered and washed with toluene. This crude product was dissolved in chloroform and extracted with water (4×), dried over potassium carbonate (K$_2$CO$_3$) and concentrated to afford the pure quinolinone product (285 mg, 69%). $^1$H NMR (300 MHz, DMSO-d$_6$) δ 12.4 (br.s, 1H), 8.45 (d, 1H, J=3.0 Hz), 8.21 (d, 1H, J=1.3 Hz), 7.86 (t, 1H, J=1.5 Hz), 7.64 (dd, 1H, J=8.9, 2.3 Hz, 1H), 7.46 (d, 1H, J=8.6 Hz), 7.44-7.31 (m, 3H), 7.28-7.21 (m, 2H), 6.94 (d, 1H, J=2.0 Hz). MS: 413.0 (M+H).

EXAMPLE 35

6-Chloro-4-(2-fluorophenyl)-3-(3-methyl-isoxazol-5-yl)-1H-quinolin-2-one

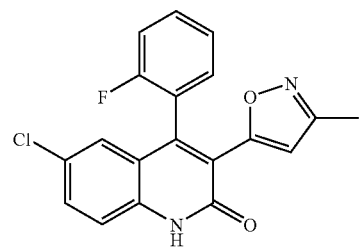

Prepared according to the procedure described for Example 34, in 40% yield. $^1$H NMR (300 MHz, CDCl$_3$) δ 11.35 (s, 1H), 7.60-7.43 (m, 5H), 7.38-7.12 (m, 2H), 6.76 (s, 1H), 2.28 (s, 3H). MS: 355.0 (M+H).

EXAMPLE 36

6-Chloro-4-phenyl-3-(3-methyl-isoxazol-5-yl)-1H-quinolin-2-one

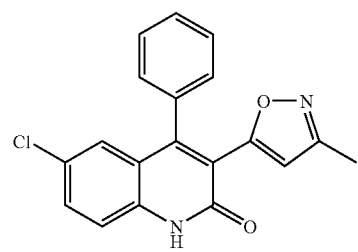

Prepared according to the procedure described for Example 34, in 53% yield. $^1$H NMR (300 MHz, DMSO-d$_6$) δ 12.5 (br.s, 1H), 7.66 (dd, 1H, J=8.9, 2.6Hz), 7.51-7.42 (m, 4H), 7.31-7.24 (m, 2H), 6.91 (d, 1H, J=2.6Hz), 6.49 (s, 1H), 2.13 (s, 3H). MS: 337.2 (M+H).

EXAMPLE 37

6-Chloro-3-(3-methyl-isoxazol-5-yl)-4-pyridin-2-yl-1H-quinolin-2-one

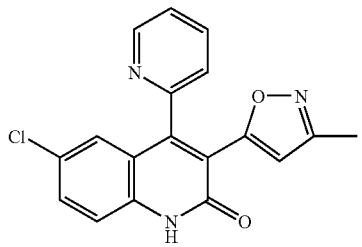

EXAMPLE 37a (2-Amino-5-chlorophenyl)-pyridin-2-yl-methanone

EXAMPLE 38

6-Chloro-3-(3-methyl-isoxazol-5-yl)-4-pyridin-3-yl-1H-quinolin-2-one

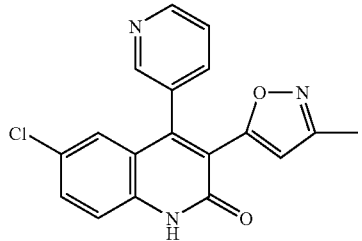

EXAMPLE 38a (2-amino-5-chlorophenyl)-pyrid-4-yl-methanone

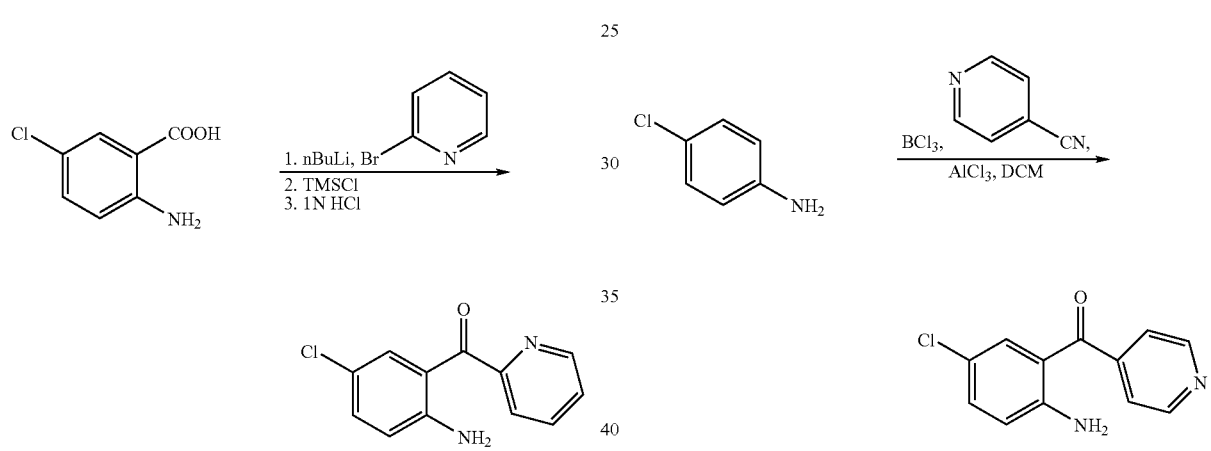

To a cooled solution (−40° C.) of 2-bromopyridine (1.68 mL, 17.6 mmol) in tetrahydrofuran (THF) (30 mL) was added n-butyllithium (nBuLi) (9.7 mL, 19 mmol, 2M in pentane) in a dropwise fashion and the resulting mixture was stirred for 30 min. 2-amino-5-chlorobenzoic acid (0.7 g, 4 mmol) was added and stirring was continued at 0° C. After 2 h, the mixture was quenched with trimethylchlorosilane (TMSCl) (10 mL), and hydrolyzed with 1N HCl (30 mL). The aqueous layer was separated from the organic phase, neutralized with 3N aq. sodium hydroxide, and extracted with ether (3×100 mL). The combined ether extracts were dried (Na$_2$SO$_4$), filtered, concentrated and purified by flash chromatography on silica gel [hexanes:ethyl acetate (7:3)] to give (2-amino-5-chlorophenyl)-pyridin-2-yl-methanone (0.71 g, 76%).

The title compound was prepared according to the procedure described for example 34, in 40% yield. $^1$H NMR (300 MHz, CDCl$_3$) δ 11.87 (s, 1H), 8.76 (d, J=4.8 Hz, 1H), 7.92-7.79 (m, 1H), 7.58-7.48 (m, 1H), 7.48-7.40 (m, 1H), 7.36 (d, J=9.6 Hz, 1H), 7.36 (d,J=9.6 Hz, 1H), 7.13 (d, J=2.4 Hz, 1H), 6.80 (s, 1H), 2.28 (s, 3H). MS: 338.0 (M+H).

A solution of 4-chloroaniline (1.3 g, 10 mmol) in dichloromethane (DCM) (15 mL) was added in a dropwise fashion to a stirred solution of boron trichloride (BCl$_3$) in heptane (1.0 M, 15 mmol) at 0° C., followed by the sequential addition of 4-cyanopyridine (1.2 g, 12 mmol) and aluminum trichloride (AlCl$_3$) (2.0 g, 15 mmol). The mixture was stirred at room temperature for 30 min, and then heated to reflux overnight. After cooling to room temperature, the reaction was carefully quenched with cold 2N HCl (60 mL), then warmed to 80° C. for 30 min. The mixture was extracted with DCM (2×50 mL). The separated aqueous layer was neutralized with 3N NaOH and extracted with DCM (3×50 mL). The organic layers were combined, dried (MgSO$_4$), filtered, concentrated, and purified by flash chromatography on silica gel [hexanes:ethyl acetate (7:3)] to give (2-amino-5-chlorophenyl)-pyrid-4-yl-methanone as a yellow solid (1.4 g, 60%).

The title compound was prepared according to the procedure described for example 34, in 40% yield. $^1$H NMR (300 MHz, DMSO-d$_6$) δ 8.67 (dd, J=2.5, 5.5 Hz, 1H), 8.48-8.45 (m, 1H), 7.82-7.76 (m, 1H), 7.65 (dd, J=3.8, 8.7 Hz, 1H), 7.56-7.50 (m, 1H), 7.45 (d, J=8.0 Hz, 1H), 6.88 (d, J=3.0 Hz, 1H), 6.66 (s, 1H), 2.15 (s, 3H). MS: 338.1 (M+H).

EXAMPLE 39

6-Bromo-3-(3-methyl-isoxazol-5-yl)-4-phenyl-1H-quinolin-2-one

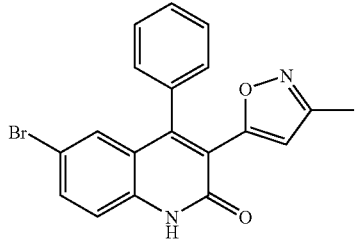

Prepared according to the procedure described for Example 34, in 55% yield. $^1$H NMR (300 MHz, DMSO-$d_6$) δ 12.54 (s, 1H), 7.76 (dd, J=3.6, 9.6 Hz, 1H), 7.51-7.44 (m, 3H), 7.38 (d, J=9.3 Hz, 1H), 7.30-7.23 (m, 2H), 7.05 (d, J=2.1 Hz, 1H), 6.48 (s, 1H), 2.13 (s, 3H). MS: 381.0 (M+H).

EXAMPLE 40

6-Chloro-4-(3-hydroxyphenyl)-3-(3-methyl-isoxazol-5-yl)-1H-quinolin-2-one

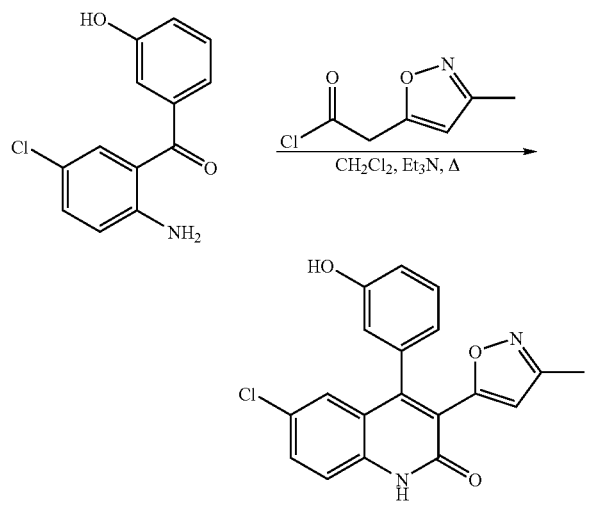

A mixture of 2-amino-5-chloro-3'-hydroxybenzophenone (0.1 g, 0.4 mmol), (3-methyl-isoxazol-5-yl)-acetyl chloride (1.18 mmol) [synthesized from the reaction between (3-methyl-isoxazol-5-yl)-acetic acid hydrochloride and oxalyl chloride catalyzed by N,N-dimethylformamide in DCM], triethylamine (Et$_3$N) (0.20 mL) and DCM (10 mL) was heated to reflux overnight. The mixture was then cooled to room temperature and concentrated, and the residue was purified by flash chromatography on silica gel (5% methanol in DCM) to give 6-chloro-4-(3-hydroxyphenyl)-3-(3-methyl-isoxazol-5-yl)-1H-quinolin-2-one (99 mg, 70%). $^1$H NMR (300 MHz, DMSO-d6) δ 9.68 (s, 1H), 7.68-7.60 (m, 2H), 7.43 (d, J=10.0 Hz, 1H), 7.25 (t, J=10.0 Hz, 1H), 7.01-6.97 (m, 1H), 6.88-6.80 (m, 1H), 6.68-6.59 (m, 1H), 6.47 (s, 1H), 2.15 (s, 3H). MS: 353.2 (M+H).

EXAMPLE 41

6-Chloro-3-(3-methyl-isoxazol-5-yl)-4-pyridin-4-yl-1H-quinolin-2-one

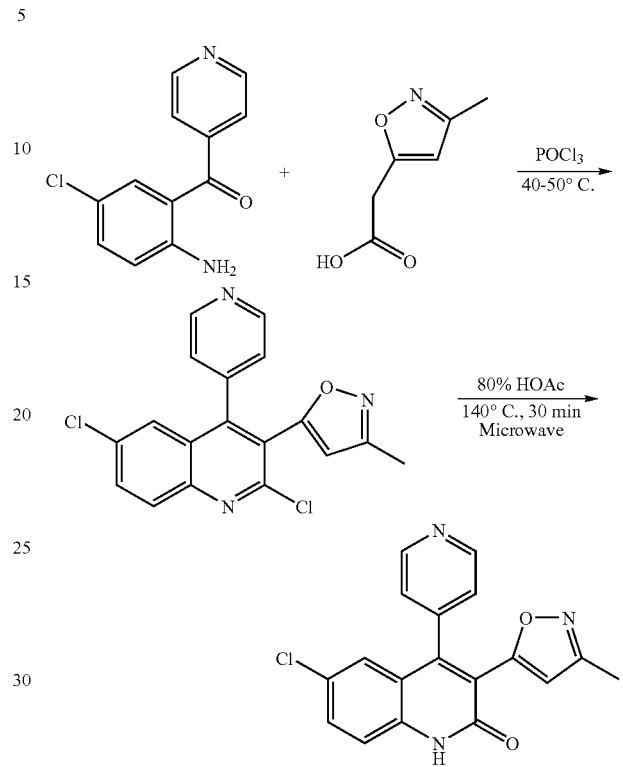

A solution of (2-amino-5-chlorophenyl)-pyridin-4-yl-methanone (50 mg, 0.22 mmol) and (3-methyl-5-isoxazol-5-yl)-acetic acid (30 mg, 0.22 mmol) were dissolved in POCl$_3$ (1 mL). The resulting solution was stirred at approximately 45° C. for 5 h. After cooling to room temperature, ethyl acetate (EtOAc) (10 mL) was added and excess POCl$_3$ was carefully quenched with saturated aqueous NaHCO$_3$ (until basic). After separating the two phases, the aqueous phase was extracted with EtOAc (3×10 mL) and the combined organic layers were dried over Na$_2$SO$_4$ and concentrated. The resulting chloroquinoline was dissolved in 80% aqueous acetic acid (HOAc) (2 mL) and heated in a microwave reactor (Smith Synthesizer) in a sealed tube at 140° C. for 30 min. Concentration under reduced pressure afforded the quinolinone product as the hydroacetate salt. $^1$H NMR (300 MHz, DMSO-$d_6$) δ 8.73-8.68 (m, 2H), 7.71-7.66 (m, 2H), 7.47 (d, J=9.5 Hz, 1H), 7.39-7.34 (m, 2H), 6.86 (d, J=4.3 Hz, 1H), 6.69 (s, 1H), 2.16 (s, 3H). MS: 338.0 (M+H).

EXAMPLE 42

6-(1.2-Dihydroxy-ethyl)-3-(3-methyl-isoxazol-5-yl)-4-phenyl-1H-quinolin-2-one (e)

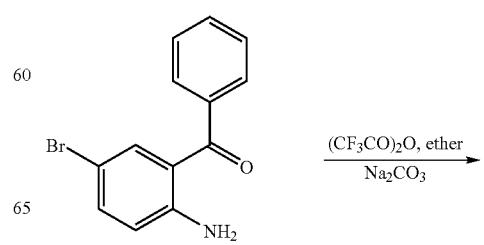

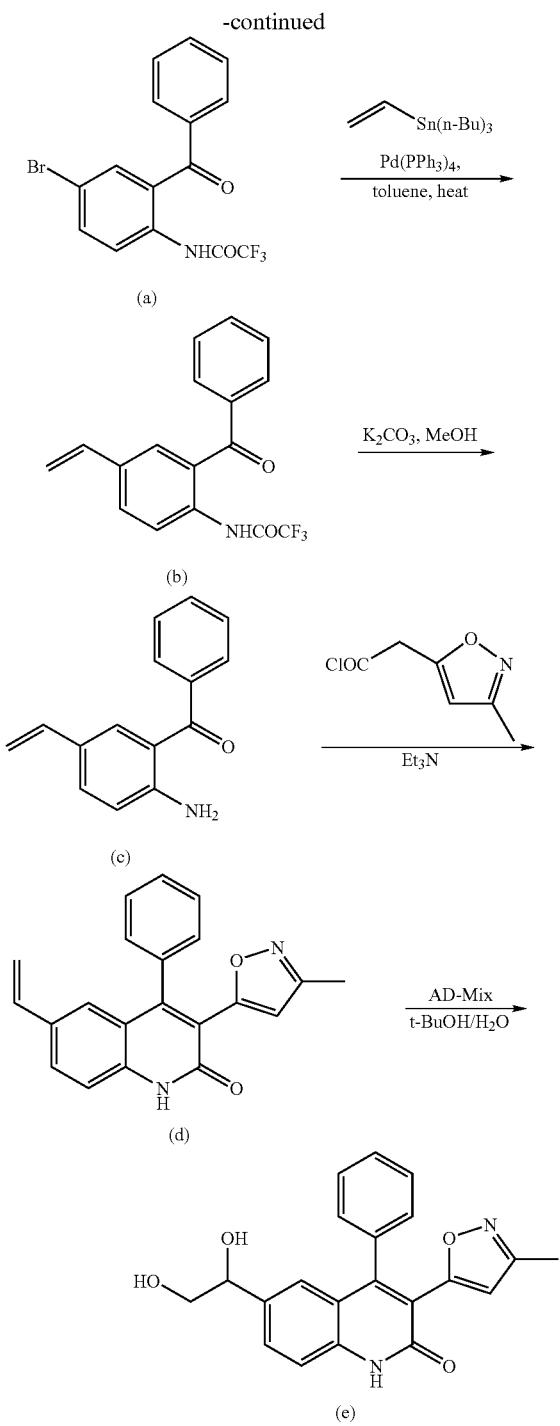

(a)

(b)

(c)

(d)

(e)

To a solution of 2-amino-5-bromobenzophenone (0.69 g, 2.5 mmol) in dry ether (25 mL) was added anhydrous sodium carbonate (1.7 g, 16 mmol). The mixture was cooled to 0° C. followed by the portionwise addition of trifluoroacetic anhydride [(CF$_3$CO)$_2$O] (1.74 mL, 12.3 mmol). When the addition was complete, the mixture was warmed to room temperature and stirred for 1.5 h. The mixture was then partitioned between DCM (40 mL) and water (40 mL). The organic layer was dried (MgSO$_4$), filtered, and concentrated to give N-(2-benzoyl-4-bromophenyl)-2,2,2-trifluoroacetamide (a) as a white solid (0.93 g, 100%).

(b)

To a solution of N-(2-benzoyl-4-bromophenyl)-2,2,2-trifluoroacetamide (a) (0.37 g, 1.0 mmol) in degassed dry toluene (10 mL) was added a solution of tetrakis(triphenylphosphine) palladium [Pd(PPh$_3$)$_4$] in toluene (5 mL) under argon. The mixture was heated to reflux and tributyl(vinyl) tin (0.29 mL, 1mmol) was added in a dropwise fashion. After refluxing overnight, the mixture was cooled to room temperature and filtered. The filtrate was concentrated and the residue was purified by flash chromatography on silica gel [hexanes: ethyl acetate (9:1)] to give N-(2-benzoyl-4-vinylphenyl)-2,2,2-trifluoro-acetamide (b) (0.22 g, 70%). $^1$H NMR (300 MHz, CDCl$_3$) δ 12.0 (s, 1H), 8.62 (d, J=10.9 Hz, 1H), 7.80-7.60 (m, 5H), 7.60-7.43 (m, 2H), 6.65 (dd, J=11, 19.6 Hz, 1H), 5.69 (d, J=19.6 Hz, 1H), 5.29 (d, J=11 Hz,1H). MS: 320.2 (M+H).

(c)

N-(2-Benzoyl-4-vinylphenyl)-2,2,2-trifluoroacetamide (b) (0.32 g, 1.0 mmol) was dissolved in a mixture of methanol (38 mL) and water (2.3 mL) and potassium carbonate (0.7 g, 5 mmol) was added. After stirring overnight at room temperature, the mixture was concentrated. Water (20 mL) was added to the residue and the mixture was extracted with chloroform (3×50 mL). The combined organic layers were dried (MgSO$_4$), filtered, and concentrated. The residue was purified by flash chromatography on silica gel [hexanes:ethyl acetate (9:1)] to produce 2-amino-5-vinylbenzophenone (c) (0.2 g, 90%). $^1$H NMR (300 MHz, CDCl$_3$) δ 7.70-7.60 (m, 2H), 7.60-7.40 (m, 5H), 6.72 (d, J=10 Hz, 1H), 6.65 (dd, J=11, 19.6 Hz, 1H), 6.16 (s, br, 2H), 5.56 (d, J=19.6 Hz, 1H), 5.03 (d, J=11 Hz,1H). MS: 224.2 (M+H).

(d)

A mixture of 2-amino-5-vinylbenzophenone (c) (0.1 g, 0.45 mmol), (3-methyl-isoxazol-5-yl)-acetyl chloride (0.9 mmol) [from example 4], triethylamine (0.20 mL) and DCM (10 mL) was heated to reflux overnight. After the mixture was cooled to room temperature and concentrated, the residue was purified by flash chromatography on silica gel (5% methanol in DCM) to give 3-(3-methyl-isoxazol-5-yl)-4-phenyl-6-vinyl-1H-quinolin-2-one (d) (0.12 g, 81%). $^1$H NMR (300 MHz, CDCl$_3$) δ 12.68 (s, 1H), 7.74-7.65 (m, 1H), 7.52-7.41 (m, 4H), 7.30-7.13 (m, 3H), 6.58 (dd, J=11, 19.6 Hz, 1H), 6.45 (s, 1H), 5.62 (d, J=19.6 Hz, 1H), 5.18 (d, J=11 Hz,1H), 2.27 (s, 3H). MS: 329.2 (M+H).

(e)

AD-mix β was dissolved in 50% aq. tert-butanol (10 mL) followed by 3-(3-methyl-isoxazol-5-yl)-4-phenyl-6-vinyl-1H-quinolin-2-one (d) (60 mg, 0.18 mmol) and the resulting mixture was stirred at room temperature overnight. Sodium sulfite (0.3 g) was added and stirring was continued until the solution cleared. The mixture was extracted with ethyl acetate (1×20 mL, 2×10 mL) and the combined organic layers were dried (MgSO$_4$), filtered, and concentrated. The residue was purified by flash chromatography on silica gel (5% methanol in DCM) to give 6-(1,2-dihydroxy-ethyl)-3-(3-methyl-isoxazol-5-yl)-4-phenyl-1H-quinolin-2-one (e) (66 mg, 100%). $^1$H NMR (300 MHz, DMSO-d$_6$) δ 12.3 (s, 1H), 7.56 (dd, J=2.6, 6.9 Hz, 1H), 7.49-7.41 (m, 3H), 7.37 (d, J=8.6 Hz, 1H), 7.27-7.18 (m, 1H), 7.09-7.04 (m, 1H), 6.41 (s, 1H), 5.25-5.20 (m, 1H), 4.65 (dd, J=6.4, 7.7Hz, 1H), 4.46-4.36 (m, 1H), 2.12 (s, 3H). MS: 363.2 (M+H).

EXAMPLE 43

3-(3-Methyl-isoxazol-5-yl)-2-oxo-4-phenyl-1,2-di-hydroquinoline-6-carboxaldehyde (a)

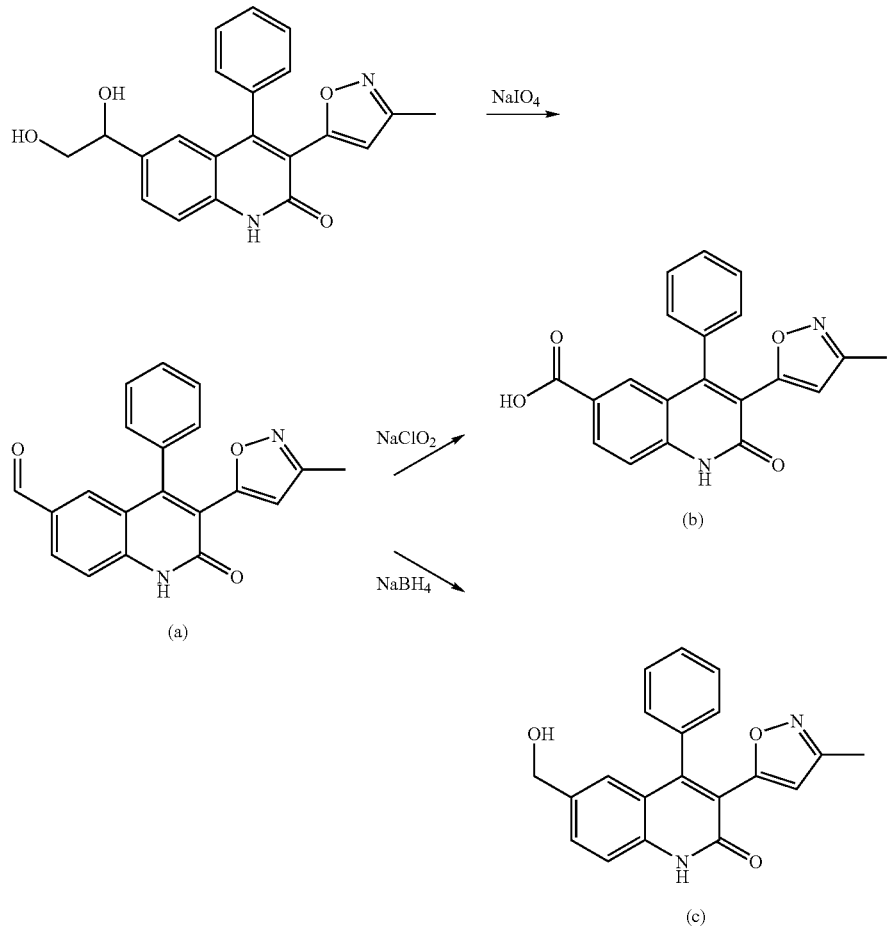

A mixture of 6-(1,2-dihydroxy-ethyl)-3-(3-methyl-isoxazol-5-yl)-4-phenyl-1H-quinolin-2-one (40 mg, 0.11 mmol), sodium periodate (94 mg, 0.44 mmol), saturated aqueous sodium bicarbonate (0.2 mL), and DCM (5 mL) was stirred for 4 h at room temperature, then filtered and concentrated. The residue was purified by flash chromatography on silica gel to provide 3-(3-methyl-isoxazol-5-yl)-2-oxo-4-phenyl-1,2-dihydroquinoline-6-carboxaldehyde (a) as a white solid (31 mg, 85%).

EXAMPLE 44

3-(3-Methylisoxazol-5-yl)-2-oxo-4-phenyl-1,2-dihydroquinoline-6-carboxylic acid (b)

3-(3-methyl-isoxazol-5-yl)-2-oxo-4-phenyl-1,2-dihydroquinoline-6-carboxaldehyde (a) (16 mg, 0.05 mmol) was dissolved in tert-butanol (2 mL) followed by the sequential addition of saturated aqueous sodium phosphate monobasic solution (0.25 mL), 2-methyl-2-butene (0.05 mL), and sodium chlorite (NaClO$_2$) (7 mg, 0.08 mmol). The mixture was stirred at room temperature for 3.5 h and concentrated. The residue was dissolved in ethyl acetate (15 mL), dried (MgSO$_4$), filtered, and concentrated to give 3-(3-methyl-isoxazol-5-yl)-2-oxo-4-phenyl-1,2-dihydroquinoline-6-carboxylic acid (b) as a white solid (17.3 mg, 100%). $^1$H NMR (300 MHz, CD$_3$OD) δ 8.19 (dd, J=6.4, 8.0 Hz, 1H), 7.96 (d, J=6.4 Hz, 1H), 7.51-7.43 (m, 4H), 7.31-7.23 (m, 2H), 6.33 (s, 1H), 2.18 (s, 3H). MS: 347.2 (M+H).

EXAMPLE 45

6-Hydroxymethyl-3-(3-methylisoxazol-5-yl)-4-phenyl-1H-quinolin-2-one (c)

A mixture of 3-(3-methyl-isoxazol-5-yl)-2-oxo-4-phenyl-1,2-dihydro-quinoline-6-carboxaldehyde (a) (33 mg, 0.11 mmol), sodium borohydride (NaBH4) (4 mg, 0.1 mmol) in DCM (1 mL) and methanol (1 mL) was stirred at room temperature for 1.5 h, and then concentrated. To the residue was added DCM (10 mL) and water (1 mL). The organic layer was separated from the aqueous layer, dried (MgSO$_4$), filtered, and concentrated. The residue was purified by flash chromatography on silica gel to give 6-hydroxymethyl-3-(3-methylisoxazol-5-yl)-4-phenyl-1H-quinolin-2-one (c) (33 mg, 90%). $^1$H NMR (300 MHz, CD$_3$OD) δ 7.65-7.58

(m, 1H), 7.49-7.38 (m, 4H), 7.30-7.20 (m, 3H), 6.30 (s, 1H), 4.51 (s, 2H), 2.17 (s, 3H). MS: 333.2 (M+H).

EXAMPLE 46

(General Procedure for the Preparation of 3-(3-Alkyl-isoxazol-5-yl)-Quinolinones)

3-(3-tert-Butyl-isoxazol-5-yl)-6-chloro-4-phenyl-1H-quinolin-2-one (b)

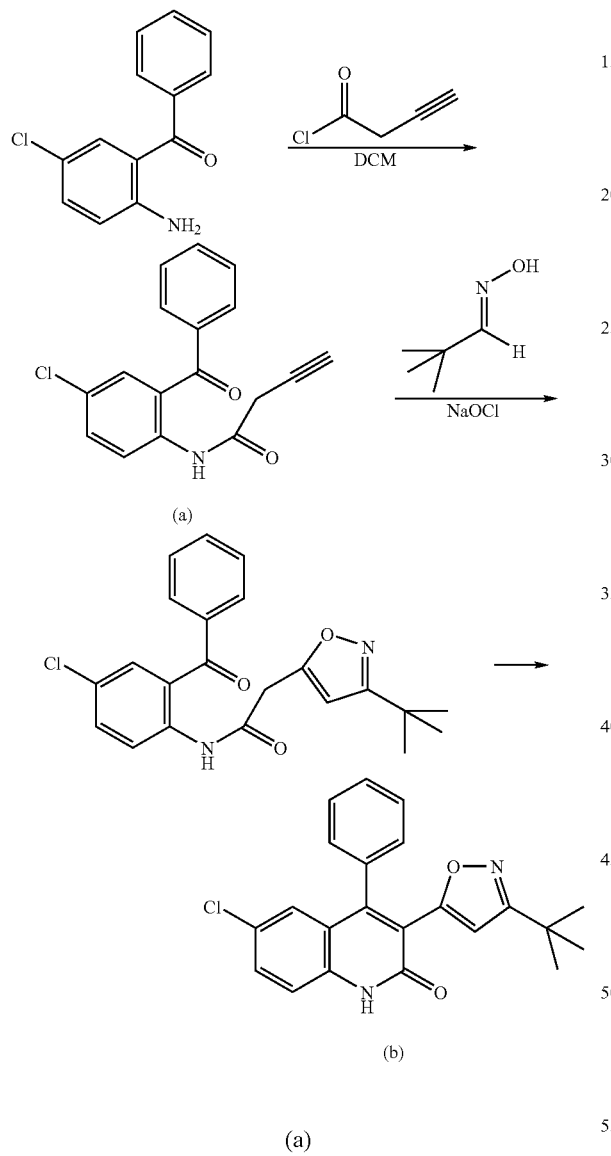

(a)

To a solution of 3-butynoic acid (0.421 g; 5.01 mmol) in anhydrous DCM (10 mL) was added oxalyl chloride (0.48 mL, 5.5 mmol) and a drop of DMF. After stirring for 1 h, 2-amino-5-chlorobenzophenone (1.16 g, 5.01 mmol) was added to the newly generated acid chloride at 0° C. The reaction mixture was stirred at 25° C. for 15 min, and then refluxed for 30 min. After cooling to room temperature, the solvent was evaporated to provide a yellow oil which was purified by flash chromatography (silica gel) to afford but-3-ynoic acid (2-benzoyl-4-chlorophenyl)amide (a) (1.33 g, 89%) as a yellow solid. $^1$H NMR (300 MHz, CDCl$_3$): δ 11.25 (s, 1H), 8.59 (d, J=9.3 Hz, 1H), 7.74-7.72 (m, 2H), 7.72-7.61 (m, 1H), 7.55-7.26 (m, 4H), 3.41 (d, J=2.7 Hz, 2H), 2.60 (t, J=2.7 Hz, 1H). MS: 298 (M+H).

(b)

To an ice-cold solution of but-3-ynoic acid (2-benzoyl-4-chlorophenyl)amide (a) (0.100 g, 0.336 mmol) in anhydrous DCM (7 mL) was added 2,2-dimethylpropionaldehyde oxime (0.204 g, 2.02 mmol) and sodium hypochlorite solution (3.50 mL). After stirring for 2 h at 0° C., the reaction was warmed to 25° C. and stirred overnight. The organic layer was separated, dried (MgSO$_4$), and concentrated to provide N-(2-benzoyl-4-chlorophenyl)-2-(3-tert-butyl-isoxazol-5-yl)-acetamide as a yellow oil. This ketoamide was dissolved in anhydrous toluene (4 mL) and treated with triethylamine (0.5 mL). After stirring for 12 h at 25° C., the reaction mixture was evaporated to afford the crude product as a yellow oil. Purification by flash chromatography afforded 3-(3-tert-butyl-isoxazol-5-yl)-6-chloro-4-phenyl-1H-quinolin-2-one (b) (0.10 g, 77% yield) as a white solid. $^1$H NMR (300 MHz, CDCl$_3$): δ 11.83 (s, 1H), 7.52-7.45 (m 4H), 7.36 (d, J=8.6 Hz, 1H), 7.26-7.20 (m, 3H), 6.42 (s, 1H), 1.26 (s, 9H). MS: 379 (M+H).

EXAMPLE 47

6-Chloro-3-(3-isopropyl-isoxazol-5-yl)-4-phenyl-1H-quinolin-2-one

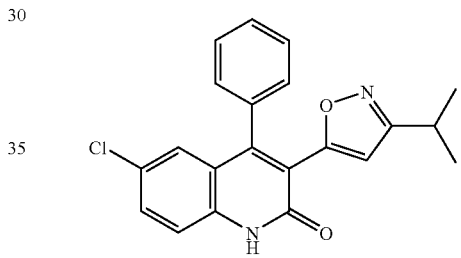

Prepared according to the procedure described for Example 46, in 74% yield. $^1$H NMR (300 MHz, CDC$_3$): δ 12.77 (s, 1H), 7.52-7.7.41 (m, 5H), 7.26-7.20 (m, 3H), 3.00 (h, J=6.9 Hz, 1H), 1.22 (d, J=6.9 Hz, 6H). MS: 365 (M+H).

EXAMPLE 48

6-Chloro-3-(3-phenethyl-isoxazol-5-yl)-4-phenyl-1H-quinolin-2-one

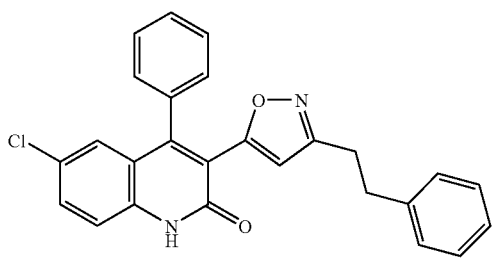

Prepared according to the procedure described for Example 46, in. 75% yield. $^1$H NMR (300 MHz, CDCl$_3$): δ 12.23 (s, 1H), 7.53-7.46 (m, 4H), 7.37 (d, J=8.9 Hz, 1H), 7.32-7.21 (m, 6H), 7.19-7.15 (m, 2H), 6.38 (s, 1H), 2.94 (s, 4H). MS: 427 (M+H).

EXAMPLE 49

(General Procedure for the Preparation of 3-(Oxazol-2-yl)-Quinolinones)

6-Chloro-3-(4-isobutyl-oxazol-2-yl)-4-phenyl-1H-quinolin-2-one (d)

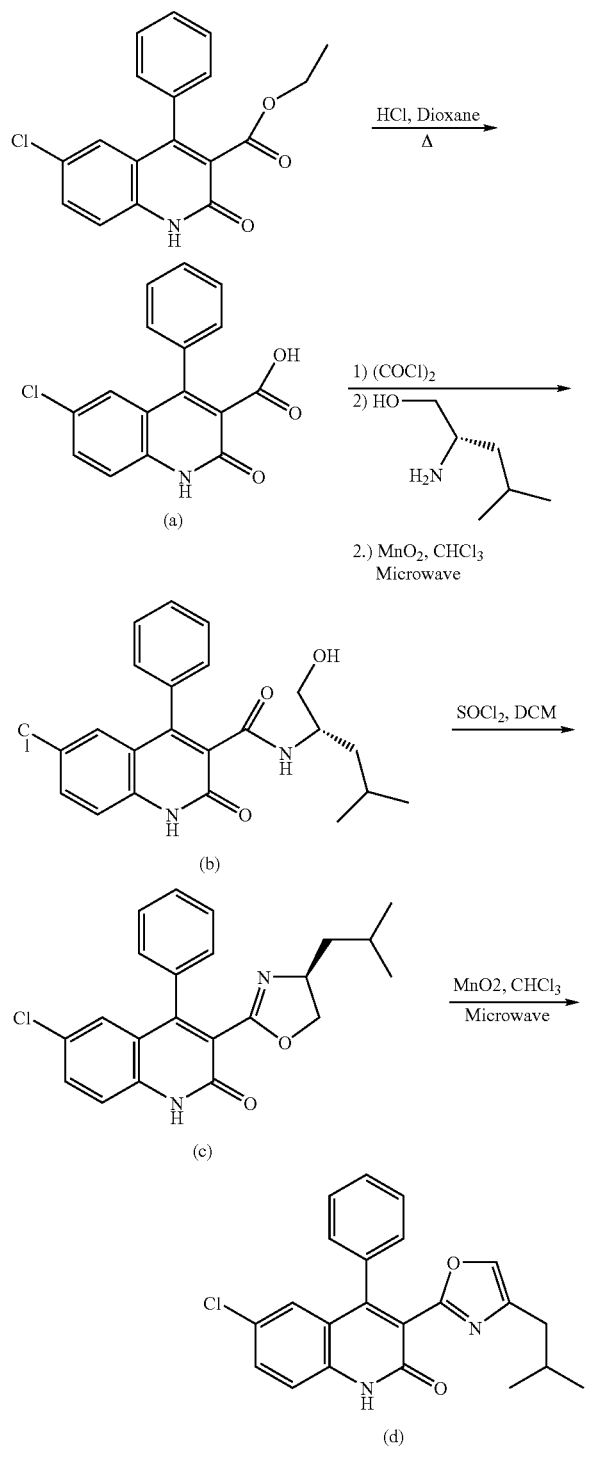

(a)

A mixture of 6-chloro-2-oxo-4-phenyl-1,2-dihydro-quinoline-3-carboxylic acid ethyl ester (200 mg, 0.61 mmol), 10% HCl (1 mL) and dioxane (3 mL) was heated to reflux for 48 h. After cooling, water was added and the resulting precipitate was collected by filtration, washed with water and dried to afford 6-chloro-2-oxo-4-phenyl-1,2-dihydro-quinoline-3-carboxylic acid (a) (143 mg, 78%). MS: 300.5 (M+H).

To a suspension of 6-chloro-2-oxo-4-phenyl-1,2-dihydro-quinoline-3-carboxylic acid (a) (600 mg, 2 mmol) in DCM (10 mL) was added oxalyl chloride (220 µL, 2.5 mmol) followed by a few drops of DMF. After stirring for 4 h at room temperature, the mixture was concentrated to dryness and a portion of the crude acid chloride thus obtained (IR: 1780 cm$^{-1}$) was used directly in the next step.

(b)

To a stirring suspension of 6-chloro-2-oxo-4-phenyl-1,2-dihydro-quinoline-3-carboxylic acid chloride (29 mg, 0.09 mmol) in DCM (0.5 mL) was added (S)-(+)-leucinol (30 µL, 0.23 mmol). Within 5 min, the mixture became homogeneous and the reaction was complete as determined by LCMS. Chloroform (2 mL) was added, and the solution was extracted with IN HCl (4×1 mL) and water (2×1 mL). The chloroform layer was purified directly by flash chromatography eluting with chloroform, then chloroform/methanol (100:1)->(50:1)->(25:1) to afford 6-chloro-2-oxo-4-phenyl-1,2-dihydro-quinoline-3-carboxylic acid (1-hydroxymethyl-3-methylbutyl)amide (b) (19 mg, 52%) as a white powder. MS: 399.2 (M+H).

(c)

To a mixture of 6-chloro-2-oxo-4-phenyl-1,2-dihydro-quinoline-3-carboxylic acid (1-hydroxymethyl-3-methylbutyl)amide (b) (30.0 mg, 0.075 mmol) in DCM (8.0 mL) was added thionyl chloride (31.0 gL, 0.40 mmol) at rt. The reaction was stirred for 0.5 h at rt, cooled to 0° C., quenched with a cold solution of NaOH (1 N), and extracted with DCM (3×10 mL). The solvent was then removed in vacuo to provide 6-chloro-3-(4-isobutyl-4,5-dihydro-oxazol-2-yl)-4-phenyl-1H-quinolin-2-one (c) (25 mg, 87%). $^1$H NMR (CDCl$_3$): δ 12.60 (b s, 1 H), 7.55-7.35 (m, 7 H); 7.20 (d, 1 H), 4.40 (t, 1 H), 4.30-4.20 (m, 1 H), 3.7 (t, 1 H), 1.60-1.50 (m, 1 H), 1.20-1.00 (m, 2 H), 0.80(dd, 6 H). MS: 381.3 (M+H).

(d)

A mixture of 6-chloro-3-(4-isobutyl-4,5-dihydro-oxazol-2-yl)-4-phenyl-1H-quinolin-2-one (c) (10.0 mg, 0.025 mmol), MnO$_2$ (15 mg) and CHCl$_3$ (1.0 mL) in a sealed tube was heated at 125° C. for 45 min in a microwave reactor (Smith Synthesizer). The mixture was then filtered through a small pad of celite and purified by prep TLC (5% MeOH/EtOAc) to afford 6-chloro-3-(4-isobutyl-oxazol-2-yl)-4-phenyl-1H-quinolin-2-one (d) (2 mg, 20%). $^1$H NMR (acetone-d$_6$): δ 11.20 (b s, 1 H), 7.60-7.20 (m, 9 H), 2.20 (d, 2 H), 1.80-1.65 (m, 1 H), 0.75 (d, 6 H). LCMS: 379.3 (M+H).

EXAMPLE 50

(General Procedure for the Preparation of 3-(1,2,3-Triazol-4-yl)-Quinolinones)

3-(1-Benzyl-1H-[1,2,3]triazol-4-yl)-6-chloro-4-phenyl-1H-quinolin-2-one

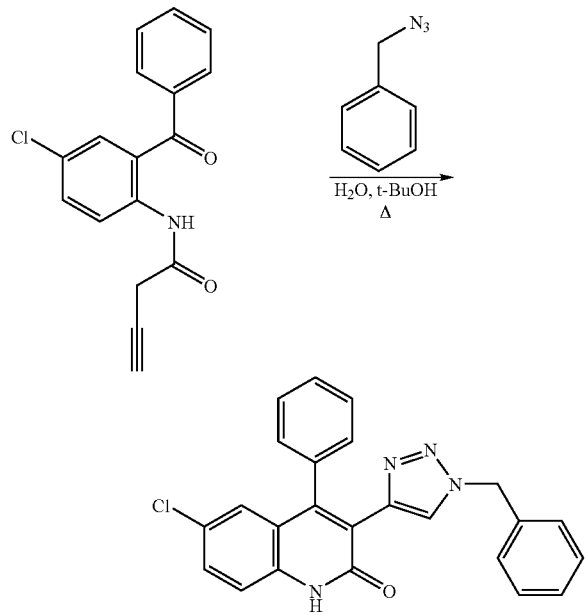

To a solution of but-3-ynoic acid (2-benzoyl-4-chlorophenyl)-amide (from Example 7) (0.056 g, 0.188 mmol) in 50% aq. tert-butanol (5 mL) was added benzyl azide (0.07 mL, 0.56 mmol), sodium ascorbate (0.012 g, 0.0564 mmol), and copper(II) sulfate pentahydrate (0.002 g, 5.64 µmol). After stirring at 70° C. for 15 hours, the reaction mixture was partitioned between ethyl acetate (15 mL) and water (15 mL). The aqueous layer was further extracted with ethyl acetate (2×15 mL) and the combined organic layers were dried (MgSO$_4$) and concentrated. The residual yellow oil was purified by flash chromatography (silica gel) to afford 3-(1-benzyl-1H-[1,2,3]triazol-4-yl)-6-chloro-4-phenyl-1H-quinolin-2-one (0.064 g, 82% yield) as white solid. $^1$H NMR (300 MHz, CDCl$_3$): δ 12.42 (s, 1H), 7.51 (s, 1H), 7.39-7.32 (m, 7.5H), 7.29 (s, 0.5H), 7.18-7.15 (m, 3H), 7.09-7.06 (m, 2H), 5.46 (s, 2H). MS: 413 (M+H).

EXAMPLE 51

3-(3-Methyl-isoxazol-5-yl)-6-nitro-4-phenyl-1H-quinolin-2-one

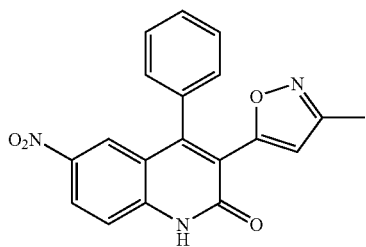

Prepared according to the procedure described in Example 41, 80% yield. $^1$H NMR (400 MHz, CDCl$_3$) δ 8.32 (m, 1H), 8.12 (d, 1H), 7.46 (m, 4H), 7.20 (m, 2H), 6.41 (s, 1H), 2.20 (s, 3H). Mass spectrum (ESI, m/z) calcd. for C$_{19}$H$_{13}$N$_3$O$_4$ 347.1, found 348.1 (M+H).

EXAMPLE 52

6-Amino-3-(3-methyl-isoxazol-5-yl)-4-phenyl-1H-quinolin-2-one

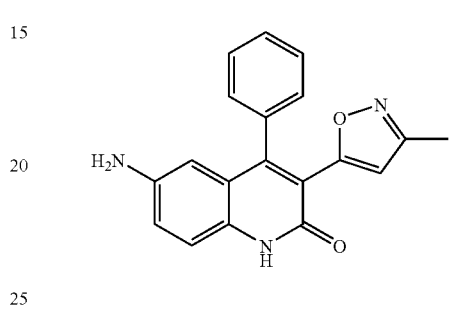

A flask charged with 3-(3-methyl-isoxazol-5-yl)-6-nitro-4-phenyl-1H-quinolin-2-one (0.2 g, 0.58 mmol)(Example 51), 50 mg of 10% Pd/C, and 10 mL of methanol was shaken on a Parr apparatus under 15 PSI of H$_2$ for 8 hrs. The solution was filtered and concentrated to give 0.18 g (100%) of the title compound as a white solid. $^1$H NMR (400 MHz, CD$_3$OD) δ 7.44 (m, 3H), 7.22 (m, 3H), 7.04 (m, 1H), 6.50 (m, 1H), 6.34 (s, 1H), 2.20 (s, 3H). Mass spectrum (ESI, m/z) calcd. for C$_{19}$H$_{15}$N$_3$O$_2$ 317.1, found 318.1 (M+H).

EXAMPLE 53

N-[3-(3-Methyl-isoxazol-5-yl)-2-oxo-4-phenyl-1,2-dihydro-quinolin-6-yl]-acetamide

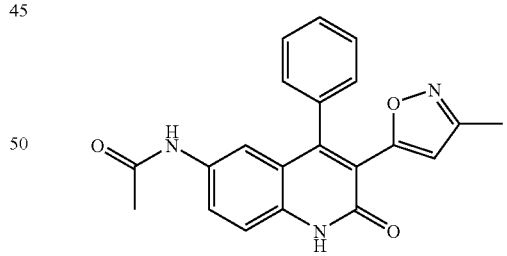

A flask charged with 6-amino-3-(3-methyl-isoxazol-5-yl)-4-phenyl-1H-quinolin-2-one (0.027 mg, 0.085 mmol)(Example 52), acetic anhydride (0.01 mL, 0.100 mmol), NEt$_3$ (0.018 mL, 0.13 mmol) and 1 mL of THF was stirred for 6 hrs at 25° C. The title compound was eluted from a 5 g SPE with 100% EtAc to give 0.015 g (50%) of a white solid. $^1$H NMR (400 MHz, CDCl$_3$) 12.30 (s, 1H), 8.06 (s, 1H), 7.72 (m, 1H), 7.36 (m, 5H), 7.14 (m, 2H), 6.36 (s, 1H), 2.22 (s, 3H), 2.02 (s, 3H). Mass spectrum (ESI, m/z) calcd. for C$_{21}$H$_{17}$N$_3$O$_3$ 359.1, found 360.2 (M+H).

EXAMPLE 54

N-[3-(3-Methyl-isoxazol-5-yl)-2-oxo-4-phenyl-1,2-dihydro-quinolin-6-yl]-methanesulfonamide

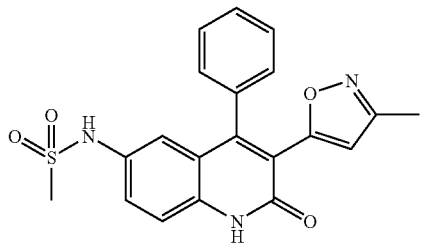

Prepared according to the procedure described in Example 53 substituting methane sulfonyl chloride for acetic anhydride. $^1$H NMR (400 MHz, DMSO-$d_6$) δ 12.32 (s, 1H), 9.66 (s, 1H), 7.45 (m, 5H), 7.24 (m, 2H), 7.02 (m, 1H), 6.44 (s, 1H), 2.88 (s, 3H), 2.12 (s, 3H). Mass spectrum (ESI, m/z) calcd. for $C_{20}H_{17}N_3O_4S$ 395.1, found 396.1 (M+H).

EXAMPLE 55

N-[3-(3-Methyl-isoxazol-5-yl)-2-oxo-4-phenyl-1,2-dihydro-quinolin-6-yl]-acrylamide

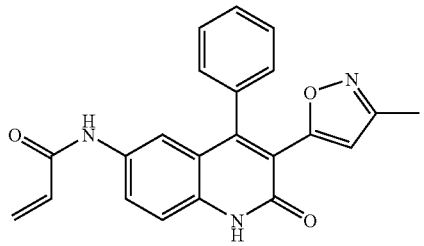

Prepared according to the procedure described in Example 53. $^1$H NMR (400 MHz, CDCl$_3$) δ 7.98 (m, 1H), 7.40 (m, 5H), 7.24 (m, 2H), 6.32 (m, 3H), 6.78 (m, 1H), 2.22 (s, 3H). Mass spectrum (ESI, m/z) calcd. for $C_{22}H_{17}N_3O_3$ 371.1, found 372.1 (M+H).

EXAMPLE 56

3-(3-Methyl-isoxazol-5-yl)-4-phenyl-6-(pyridin-2-ylamino)-1H-quinolin-2-one

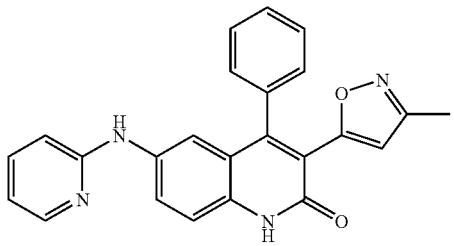

a) 2-Chloro-3-(3-methyl-isoxazol-5-yl)-6-nitro-4-phenyl-quinoline

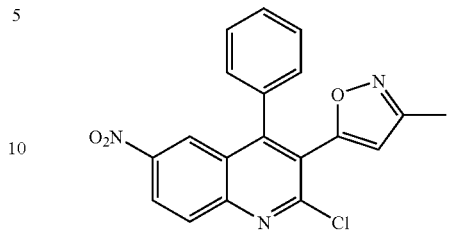

A flask charged with (2-amino-5-nitro-phenyl)-phenyl-methanone (1.3 g, 5.4 mmol), (3-methyl-isoxazol-5-yl)-acetic acid (0.74 g, 5.3 mmol), and 10 mL of phosphorus oxychloride was heated to 60° C. for 6 hrs. The reaction was concentrated and triturated with saturated NaHCO$_3$ to give a 1.9 g of a white solid that was used without further purification.

b) 2-Chloro-3-(3-methyl-isoxazol-5-yl)-4-phenyl-quinolin-6-ylamine

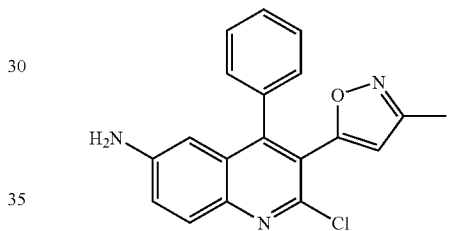

A flask charged with 2-chloro-3-(3-methyl-isoxazol-5-yl)-6-nitro-4-phenyl-quinoline (1.1 g, 3.0 mmol), NH$_4$Cl (1.6 g, 30 mmol), iron powder (0.87 g, 15 mmol), EtOH (20 mL) and H$_2$O (10 mL) was heated to 80° C. for 1 hr. The reaction was filtered and concentrated and eluted from a 20 g SPE with 30% EtAc/hex to give 0.8 g (80%) of the title compound as a white solid. $^1$H NMR (400 MHz, CDCl$_3$) δ7.96 (m, 1H), 7.40 (m, 3H), 7.22 (m, 3H), 6.62 (m, 1H), 5.92 (s, 1H), 3.98m (m, 2H), 2.22 (s, 3H). Mass spectrum (ESI, m/z) calcd. for $C_{19}H_{14}ClN_3O$ 335.1, found 336.1 (M+H).

A flask charged with 2-chloro-3-(3-methyl-isoxazol-5-yl)-4-phenyl-quinolin-6-ylamine (35 mg, 0.10 mmol), 2-bromopyridine (22 mg, 0.14 mmol), Xanthphos (7 mg, 12 mol %), Pd$_2$(dba)$_3$ (5 mg, 5 mol %), potassium t-butoxide (13 mg, 0.11 mmol) and dioxane (0.5 mL) was heated at 110° C. for 3 hrs. The product was eluted from a 5 g SPE with 30% EtAc/hex and then dissolved in 1.8 mL of acetic acid and 0.2 mL of H$_2$O and heated at 110° C. for 5 hrs. The solution was concentrated, and the residue dissolved in DCM and washed with aqueous NaHCO$_3$, dried (Na$_2$SO$_4$) and concentrated. The title compound was eluted from a 5 g SPE 30% EtAc/hex to give 10 mg (25%) of a white solid. $^1$H NMR (400 MHz, CDCl$_3$+CD$_3$OD) δ 7.98 (m, 1H), 7.59 (m, 1H), 7.38 (m, 4H), 7.14 (m, 4H), 6.61 (m, 2H), 6.32 (s, 1H), 2.14 (s, 3H). Mass spectrum (ESI, m/z) calcd. for $C_{24}H_{18}N_4O_2$ 394.1, found 394.1 (M+H).

EXAMPLE 57

3-(3H-Imidazol-4-yl)-2-oxo-4-phenyl-1,2-dihydro-quinoline-6-carbonitrile

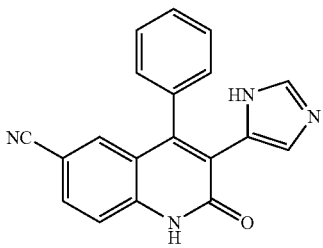

a) (2-Amino-5-bromo-phenyl)-phenyl-methanone

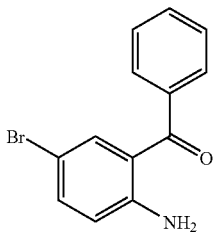

A flask charged with (2-amino-phenyl)-phenyl-methanone (5 g, 25 mmol) and DCM (80 mL) was cooled to −10° C. and NBS (4.5 g, 25 mmol) was added over 30 minutes via an addition funnel. The reaction was complete following addition of NBS and the reaction was diluted with 80 mL of DCM, washed with sat NaHCO$_3$ (2×100 mL), dried over Na$_2$SO$_4$ and concentrated to give 7 g of a crude product which was used without further purification.

b) 4-Amino-3-benzoyl-benzonitrile

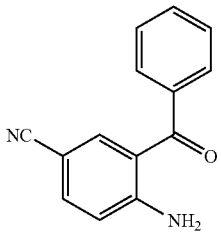

A flask charged with (2-amino-5-bromo-phenyl)-phenyl-methanone (93 mg, 0.33 mmol), copper cyanide (50 mg, 0.56 mmol), and 2 mL of DMA was heated at 180° C. for 30 min in a microwave reactor. The title compound was eluted from a 5 g SPE with 20% EtAc/hex to give 50 mg (71%) of a white solid. $^1$H NMR (400 MHz, CDCl$_3$) δ 7.81 (m, 1H), 7.62 (m, 3H), 7.50 (m, 3H), 6.78 (m, 1H), 6.68 (m, 2H).

The title compound was obtained from 4-amino-3-benzoyl-benzonitrile and (3H-imidazol-4-yl)-acetic acid according to the procedure in Example 41. $^1$H NMR (400 MHz, DMSO-d$_6$) δ 14.30 (br, 1H), 12.90 (br, 1H), 8.92 (s, 1H), 8.02 (m, 1H), 7.56 (m, 4H), 7.32 (m, 3H), 6.72 (s, 1H). Mass spectrum (ESI, m/z) calcd. for C$_{19}$H$_{12}$N$_4$O 312.1, found 313.1 (M+H).

EXAMPLE 58

3-(1-Methyl-1H-imidazol-4-yl)-2-oxo-4-phenyl-1,2-dihydro-quinoline-6-carbonitrile

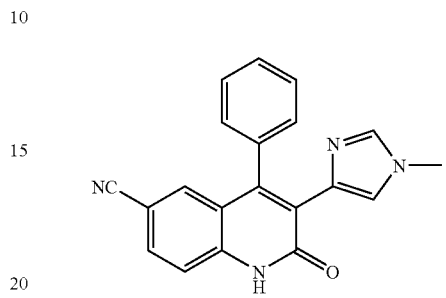

The title compound was prepared according the to procedure in Example 41. $^1$H NMR (400 MHz, CD$_3$OD) δ 8.82 (s, 1H), 7.92 (m, 1H), 7.62 (m, 4H), 7.49 (s, 1H), 7.38 (m, 2H), 6.62 (s, 1H), 3.78 (s, 3H). Mass spectrum (ESI, m/z) calcd. for C$_{20}$H$_{14}$N$_4$O 326.1, found 327.2 (M+H).

EXAMPLE 59

3-(3-Amino-isoxazol-5-yl)-6-chloro-4-phenyl-1H-quinolin-2-one

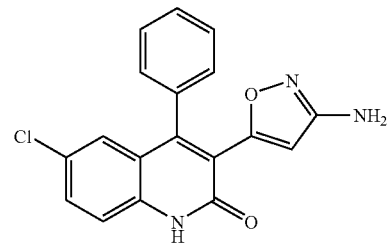

a) 6-Chloro-4-phenyl-3-[3-(trityl-amino)-isoxazol-5-yl]-1H-quinolin-2-one

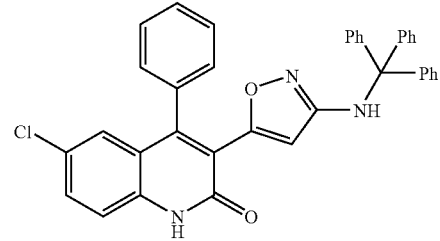

The title compound was prepared from [3-(trityl-amino)-isoxazol-5-yl]-acetic acid (U.S. Pat. No. 4,394,504) according to Example 3. $^1$H NMR (400 MHz, DMSO-d$_6$) δ 12.36 (s, 1H), 7.64 (dd, 1H), 7.42 (m, 4H), 7.20 (m, 18H), 6.90 (d, 1H), 6.02 (s, 1H). Mass spectrum (ESI, m/z) calcd. for C$_{37}$H$_{26}$ClN$_3$O$_2$ 579.1, found 580.0 (M+H).

A flask was charged with 6-chloro-4-phenyl-3-[3-(tritylamino)-isoxazol-5-yl]-1H-quinolin-2-one (0.43 g, 0.74 mmol), DCM (9 mL), MeOH (1 mL), and (TFA 1 mL) was stirred at 25° C. for 1 hr and then concentrated. The residue was triturated with EtOAc and the title compound collected by filtration to give 0.17 g (75%) of a white solid. $^1$H NMR (400 MHz, DMSO-$d_6$) δ 12.45 (s, 1H), 7.64 (dd, 1H), 7.46 (m, 4H), 7.28 (m, 2H), 6.90 (d, 1H), 5.98 (s, 1H), 5.42 (br s, 2H). Mass spectrum (ESI, m/z) calcd. for $C_{18}H_{12}ClN_3O_2$ 337.1, found 338.0 (M+H).

EXAMPLE 60

N-[5-(6-Chloro-2-oxo-4-phenyl-1,2-dihydro-quinolin-3-yl)-isoxazol-3-yl]-acetamide

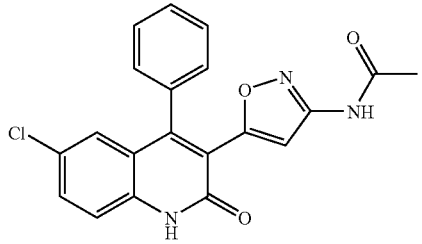

A flask charged with 3-(3-amino-isoxazol-5-yl)-6-chloro-4-phenyl-1H-quinolin-2-one (example 59)(22 mg, 0.063 mmol), acetic anhydride (9 mg, 0.082 mmol), 2,6-lutidine (11 mg, 0.10 mmol), DMAP (10 mg, 0.082 mmol) and DMF (0.5 mL) was heated at 50° C. for 2 hrs. The reaction was concentrated and the title compound was purified by RP-HPLC, eluting with 40-100% $CH_3CN$ in 0.1% $TFA/H_2O$ over 30 mins to give 15 mg (60%) the title cpd. $^1$H NMR (400 MHz, DMSO-$d_6$) δ 12.54 (s, 1H), 10.80 (s, 1H), 7.68 (m, 1H), 7.46 (m, 4H), 7.30 (m, 2H), 6.96 (m, 2H), 2.04 (s, 3H). Mass spectrum (ESI, m/z) calcd. for $C_{20}H_{14}ClN_3O_3$ 379.1, found 380.0 (M+H).

EXAMPLE 61

N'-[5-(6-Chloro-2-oxo-4-phenyl-1,2-dihydro-quinolin-3-yl)-isoxazol-3-yl]-N,N-dimethyl-formamidine

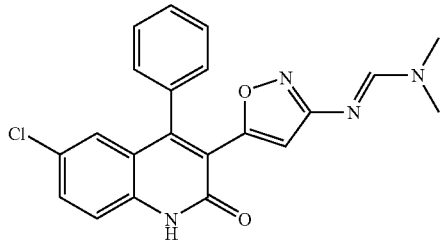

A flask charged with 3-(3-amino-isoxazol-5-yl)-6-chloro-4-phenyl-1H-quinolin-2-one (example 59)(15 mg, 0.045 mmol), methanesulfonyl chloride (7.4 mg, 0.065 mmol), 2,6-lutidine (7.4 mg, 0.068 mmol), and DMF (0.1 mL) was stirred at 25° C. for 2 hrs. The reaction was concentrated and the title compound was purified by RP-HPLC, eluting with 40-70% $CH_3CN$ in 0.1% $TFA/H_2O$ over 20 mins to give 15 mg (68%) the title cpd as a TFA salt. $^1$H NMR (400 MHz, DMSO-$d_6$) δ 12.62 (s, 1H), 8.52 (s, 1H), 7.68 (dd, 1H), 7.48 (m, 4H), 7.32 (m, 2H), 6.96 (d, 1H), 6.80 (s, 1H), 3.25 (s, 3H), 3.12 (s, 3H). Mass spectrum (ESI, m/z) calcd. for $C_{21}H_{17}ClN_4O_2$ 392.1, found 393.1 (M+H).

EXAMPLE 62

N'-[5-(6-Chloro-2-oxo-4-phenyl-1,2-dihydro-quinolin-3-yl)-isoxazol-3-yl]-N,N-dimethyl-acetamidine

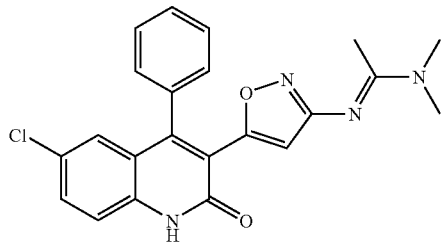

This was prepared according to Example 61 substituting dimethylacetamide for dimethylformamide and heating at 50° C. for 8 hrs. 1H NMR (400 MHz, $CD_3OD$) δ7.68 (dd, 1H), 7.52 (m, 4H), 7.32 (m, 2H), 7.18 (d, 1H), 6.60 (s, 1H), 3.42 (s, 3H), 3.32 (s, 3H), 2.36 (s, 3H). Mass spectrum (ESI, m/z) calcd. for $C_{22}H_{19}ClN_4O_2$ 406.1, found 407.1 (M+H).

EXAMPLE 63

N'-[5-(6-Chloro-2-oxo-4-phenyl-1,2-dihydro-quinolin-3-yl)-isoxazol-3-yl]-N,N-dimethyl-propionamidine

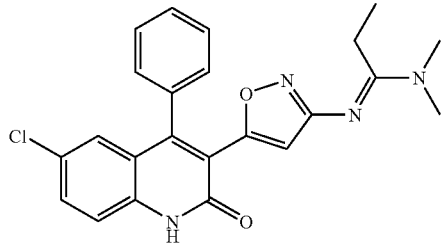

This was prepared according to example 62 substituting N,N-dimethylpropionamide for N,N-dimethylacetamide. $^1$H NMR (400 MHz, $CD_3OD$) δ 7.68 (dd, 1H), 7.52 (m, 4H), 7.32 (m, 2H), 7.18 (d, 1H), 6.60 (s, 1H), 3.44 (s, 3H), 3.32 (s, 3H), 2.72 (q, 2H), 1.14 (t, 3H). Mass spectrum (ESI, m/z) calcd. for $C_{23}H_{21}ClN_4O_2$ 420.1, found 421.1 (M+H).

EXAMPLE 64

N-[5-(6-Chloro-2-oxo-4-phenyl-1,2-dihydro-quinolin-3-yl)-isoxazol-3-yl]-methanesulfonamide

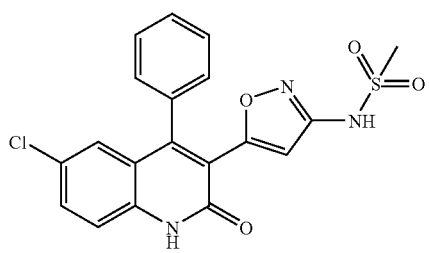

A flask charged with 3-(3-amino-isoxazol-5-yl)-6-chloro-4-phenyl-1H-quinolin-2-one (Example 59)(17 mg, 0.050 mmol), methanesulfonyl chloride (7.5 mg, 0.066 mmol), and pyridine (0.2 mL) was stirred at 25° C. for 3 hrs. The reaction was concentrated and the title compound was purified by RP-HPLC, eluting with 40-70% CH$_3$CN in 0.1% TFA/H$_2$O over 10 mins to give 40 mg (50%). $^1$H NMR (400 MHz, CD$_3$OD) δ 7.52 (dd, 1H), 7.46 (m, 3H), 7.36 (d, 1H), 7.22 (m, 2H), 7.12 (d, 1H), 6.54 (s, 1H), 3.00 (s, 3H). Mass spectrum (ESI, m/z) calcd. for C$_{19}$H$_{14}$ClN$_3$O$_4$S 415.0, found 416.0 (M+H).

EXAMPLE 65

[5-(6-Chloro-2-oxo-4-phenyl-1,2-dihydro-quinolin-3-yl)-isoxazol-3-yl]-carbamic acid 2-methanesulfonyl-ethyl ester

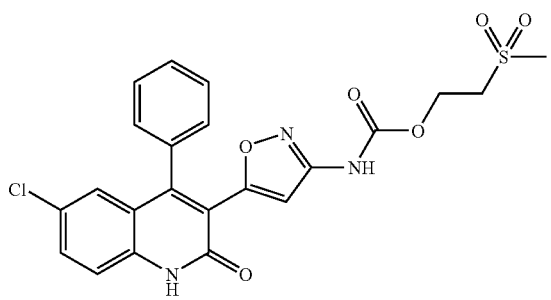

This was prepared according to Example 64 from 3-(3-amino-isoxazol-5-yl)-6-chloro-4-phenyl-1H-quinolin-2-one and carbonic acid 2,5-dioxo-pyrrolidin-1-yl ester 2-methanesulfonyl-ethyl ester. $^1$H NMR (400 MHz, DMSO-d$_6$) δ 12.62 (s, 1H), 10.78 (s, 1H), 7.66 (dd, 1H), 7.48 (m, 4H), 7.32 (m, 2H), 6.96 (d, 1H), 6.89 (s, 1H), 4.42 (t, 2H), 3.56 (t, 2H), 3.12 (s, 3H). Mass spectrum (ESI, m/z) calcd. for C$_{22}$H$_{18}$ClN$_3$O$_6$S 487.0, found 488.0 (M+H).

EXAMPLE 66

1-[5-(6-Chloro-2-oxo-4-phenyl-1,2-dihydro-quinolin-3-yl)-isoxazol-3-yl]-3-(2-morpholin-4-yl-ethyl)-urea

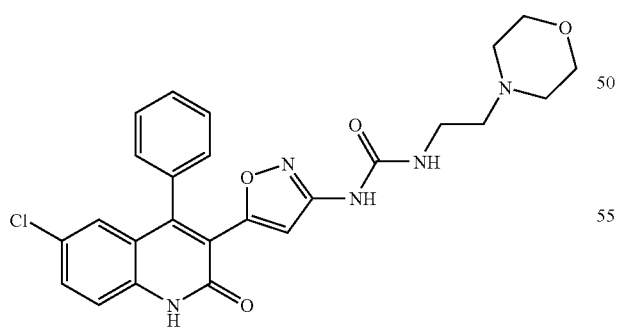

A flask charged with 3-(3-amino-isoxazol-5-yl)-6-chloro-4-phenyl-1H-quinolin-2-one (example 59)(15 mg, 0.045 mmol), 2,6-lutidine (5.5 mg, 0.052 mmol), 4-nitrophenyl chloroformate (10 mg, 0.05 mmol), and DMA (0.3 mL) was stirred at 25° C. for 10 mins and then 2-morpholin-4-yl-ethylamine (12 mg, 0.092 mmol) was added and stirring continued for 30 mins. The reaction was concentrated and the title compound was purified by RP-HPLC, eluting with 20-50% CH$_3$CN in 0.1% TFA/H$_2$O over 10 mins to give 6 mg (22%) the title cpd as a TFA salt. $^1$H NMR (400 MHz, CD$_3$OD) δ 7.62 (dd, 1H), 7.52 (m, 3H), 7.44 (m, 2H), 7.30 (m, 2H), 7.12 (d, 1H), 6.60 (s, 1H), 3.72 (m, 4H), 3.40 (m, 2H), 2.52 (m, 6H). Mass spectrum (ESI, m/z) calcd. for C$_{25}$H$_{24}$ClN$_5$O$_4$ 493.1, found 494.0 (M+H).

EXAMPLE 67

3-(3-Methyl-isoxazol-5-yl)-4,6-diphenyl-1H-quinolin-2-one

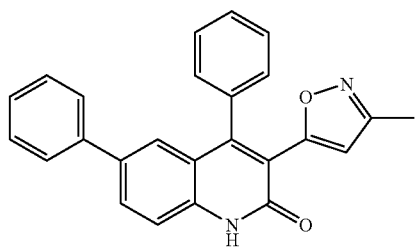

A flask was charged with 6-bromo-3-(3-methyl-isoxazol-5-yl)-4-phenyl-1H-quinolin-2-one (25 mg, 0.066 mmol)(Example 39), phenyl boronic acid (12 mg, 0.098 mmol), Pd(PPh$_3$)$_4$ (7 mg, 10 mol %), 2 M Na$_2$CO$_3$ (0.25 mL), EtOH (0.25 mL), and toluene (0.5 mL) and heated for 2 hrs at 80° C. The reaction was diluted with EtAc (10 mL) and washed with brine (2×10 mL). The organic layer was concentrated and the title product (12 mg, 50%) eluted from a 5 g SPE with 50% EtAc/hex. $^1$H NMR (400 MHz, CDCl$_3$) δ 11.42 (s, 1H), 7.82 (dd, 1H), 7.20 (m, 12H), 6.52 (s, 1H), 2.24 (s, 3H). Mass spectrum (ESI, m/z) calcd. for C$_{25}$H$_{18}$N$_2$O$_2$ 378.1, found 379.1 (M+H).

EXAMPLE 68

3-(3-Methyl-isoxazol-5-yl)-4-phenyl-6-(3-trifluoromethyl-phenyl)-1H-quinolin-2-one

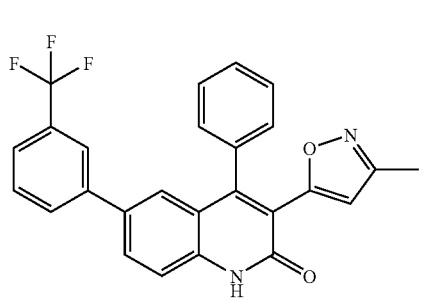

This was prepared according to Example 67. $^1$H NMR (400 MHz, CDCl$_3$) δ 12.68 (s, 1H), 7.84 (dd, 1H), 7.68 (m, 1H), 7.50 (m, 8H), 7.32 (m, 2H), 6.50 (s, 1H), 2.30 (s, 3H). Mass spectrum (ESI, m/z) calcd. for C$_{26}$H$_{17}$F$_3$N$_2$O$_2$ 446.1, found 447.1 (M+H).

EXAMPLE 69

6-(3-Methoxy-phenyl)-3-(3-methyl-isoxazol-5-yl)-4-phenyl-1H-quinolin-2-one

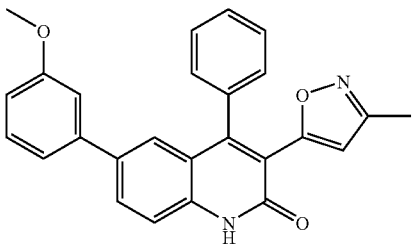

This was prepared according to Example 67. ¹H NMR (400 MHz, CDCl₃) δ 12.78 (s, 1H), 7.82 (dd, 1H), 7.44 (m, 5H), 7.26 (m, 3H), 7.08 (m, 1H), 6.98 (m, 1H), 6.84 (m, 1H), 6.46 (s, 1H), 3.86 (s, 3H), 2.28 (s, 3H). Mass spectrum (ESI, m/z) calcd. for $C_{26}H_{20}N_2O_3$ 408.1, found 409.1 (M+H).

EXAMPLE 70

3-(3-Methyl-isoxazol-5-yl)-2-oxo-4-phenyl-1,2-dihydro-quinoline-6-carbonitrile

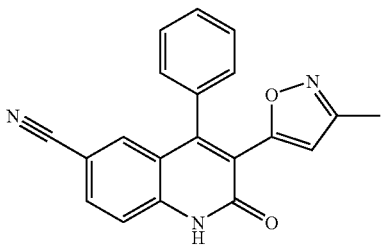

A flask was charged with 6-bromo-3-(3-methyl-isoxazol-5-yl)-4-phenyl-1H-quinolin-2-one (30 mg, 0.077 mmol)(example 39), Pd(PPh₃)₄ (5 mg, 5 mol %), NaCN (8 mg, 0.16 mmol), CuI (1.5 mg, 10 mol %), and 0.7 mL CH₃CN and heated in a sealed tube in a microwave reactor at 100° C. for 1 hr. The title compound was obtained by elution from a 10 g SPE with 50% EtAc/hex to give 13 mg (50%) of a white solid. ¹H NMR (400 MHz, CD₃OD) δ 7.78 (dd, 1H), 7.50 (m, 5H), 7.28 (m, 2H), 6.42 (s, 1H), 2.20 (s, 3H). Mass spectrum (ESI, m/z) calcd. for $C_{20}H_{13}N_3O_2$ 327.1, found 328.1 (M+H).

EXAMPLE 71

3-(3-Methyl-isoxazol-5-yl)-6-methylsulfanyl-4-phenyl-1H-quinolin-2-one

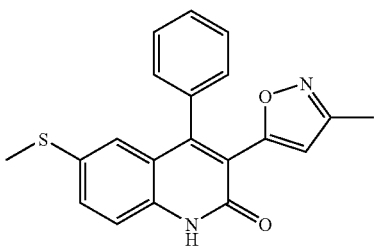

A flask was charged with 6-bromo-3-(3-methyl-isoxazol-5-yl)-4-phenyl-1H-quinolin-2-one (30 mg, 0.079 mmol)(example 39), 1 mL of THF and cooled to 0° C. A 2M solution of i-PrMgCl in THF (0.39 mL, 0.077 mmol) was added and the reaction stirred for 5 minutes at 0° C. and then cooled to −78° C. and a 2M solution of n-BuLi in hexanes (0.06 mL, 0.12 mmol) was added. After stirring for 15 minutes dimethyldisulfide (15 mg, 0.16 mmol) was added and the reaction allowed to attain RT and stirred for 30 minutes. The reaction was diluted with EtAc (10 mL) and washed with brine (2×10 mL). The organic layer was concentrated and the title product (14 mg, 50%) eluted from a 5 g SPE with 50% EtOAc/hexanes. ¹H NMR (400 MHz, CD₃OD) δ 7.54 (dd, 1H), 7.48 (m, 3H), 7.48 (d, 1H), 7.24 (m, 2H), 7.06 (d, 1H), 6.36 (s, 1H), 2.34 (s,3H), 2.24 (s, 3H). Mass spectrum (ESI, m/z) calcd. for $C_{20}H_{16}N_2O_2S$ 348.1, found 349.1 (M+H).

EXAMPLE 72

6-Methanesulfonyl-3-(3-methyl-isoxazol-5-yl)-4-phenyl-1H-quinolin-2-one

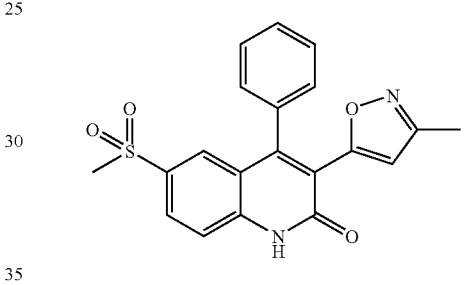

A flask charged with 3-(3-methyl-isoxazol-5-yl)-6-methylsulfanyl-4-phenyl-1H-quinolin-2-one (example 71)(50 mg, 0.14 mmol), MCPBA (77%, 64 mg, 0.29 mmol), and 2 mL of DCM was stirred for 30 mins at 25° C. The reaction was diluted with 10 mL of DCM, washed with sat. NaHCO₃ (2×10 mL) and brine (10 mL). The organic layer was concentrated and the title compound eluted from a 10 g SPE with 50% EtAc/hex to give 43 mg (80%) of a white solid. ¹H NMR (400 MHz, DMSO-d₆) δ 12.80 (s, 1H), 8.12 (dd, 1H), 7.62 (d, 1H), 7.59 (d, 1H), 7.50 (m, 3H), 7.32 (m, 2H), 6.52 (s, 1H), 3.18 (s, 3H), 2.18 (s, 3H). Mass spectrum (ESI, m/z) calcd. for $C_{20}H_{16}N_2O_4S$ 380.1, found 381.0 (M+H).

EXAMPLE 73

6-Fluoro-3-(3-methyl-isoxazol-5-yl)-4-phenyl-1H-quinolin-2-one

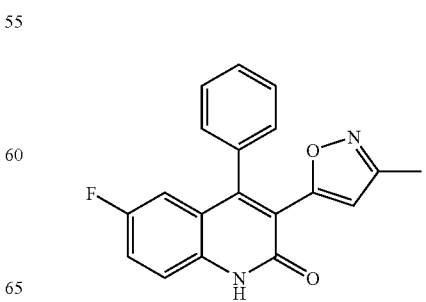

a) (2-Amino-5-fluoro-phenyl)-phenyl-methanone

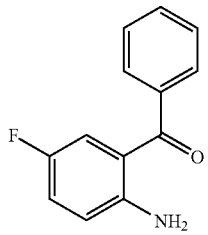

A flask charged with (2-amino-phenyl)-phenyl-methanone (0.23 g, 1.2 mmol), N-fluorobenzenesulfonimide (0.37 g, 1.2 mmol), and 4 mL of $CH_3CN$ was stirred for 4 days at RT. The reaction was diluted with 20 mL of EtOAc, washed with sat. $NaHCO_3$ (2×20 mL) and brine (20 mL). The organic layer was concentrated and the title compound eluted from a 20 g SPE with 5% EtAc/hex to give 40 mg (15%) of a white solid. $^1$H NMR (400 MHz, $CDCl_3$) δ 7.60 (m, 5H), 7.10 (m, 2H), 6.72 (m, 1H), 5.1 (br s, 2H).

The title compound was obtained according to the procedure for Example 41 from (2-amino-5-fluoro-phenyl)-phenyl-methanone. $^1$H NMR (400 MHz, $CDCl_3$) δ 12.20 (s, 1H), 7.48 (m, 4H), 7.35 (m, 1H), 7.26 (m, 2H), 6.96 (dd, 1H), 6.48 (s, 1H), 2.30 (s, 3H). Mass spectrum (ESI, m/z) calcd. for $C_{19}H_{13}FN_2O_2$ 320.1, found 321.1 (M+H).

EXAMPLE 74

3-(3-Methyl-isoxazol-5-yl)-4-phenyl-1H-quinolin-2-one

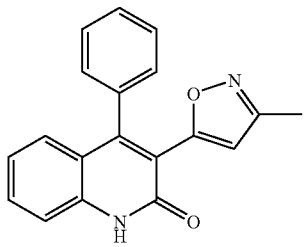

The title compound prepared according to example 41 from (2-amino-phenyl)-phenyl-methanone. $^1$H NMR (400 MHz, DMSO-$d_6$) δ 12.38 (s, 1H), 7.60 (t, 1H), 7.42 (m, 4H), 7.28 (m, 2H), 7.18 (t, 1H), 7.04 (d, 1H), 6.42 (s, 1H), 2.16 (s, 3H). Mass spectrum (ESI, m/z) calcd. for $C_{19}H_{14}N_2O_2$ 302.1, found 303.1 (M+H).

EXAMPLE 75

6-Fluoro-7-methoxy-3-(3-methyl-isoxazol-5-yl)-4-phenyl-1H-quinolin-2-one

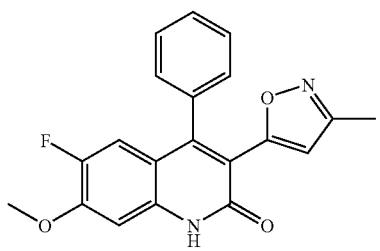

a) (2-Amino-5-fluoro-4-methoxy-phenyl)-phenyl-methanone

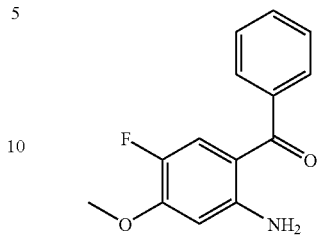

To a solution of 6,7-difluoro-2-phenyl-benzo[d][1,3]oxazin-4-one (WO 0050427A1) (0.3 g, 1.2 mmol) in 4 mL of THF at 0° C. was added a 1M THF solution of phenyl magnesium bromide (1.2 mL, 1.2 mmol) and the solution allowed to stir for 30 mins at 0° C. The reaction was diluted with 20 mL of EtAc, washed with sat. $NaHCO_3$ (2×20 mL) and brine (20 mL) and the organic layer concentrated. The residue was dissolved in MeOH (10 mL) and 6N NaOH added (0.6 mL, 3.5 mmol) and the reaction heated at 90° C. for 1 hr. The reaction was concentrated and then diluted with EtOAc (20 mL) and washed with brine (2×20 mL). The title compound was eluted from a 10 g SPE with 30% EtOAc/hexanes to give 34 mg (12%) of a white solid. Mass spectrum (ESI, m/z) calcd. for $C_{14}H_{12}FNO_2$ 245.1, found 246.1 (M+H).

The title compound was obtained according to example 41. $^1$H NMR (400 MHz, $CDCl_3$) δ 12.90 (s, 1H), 7.46 (m, 3H), 7.22 (m, 2H), 7.04 (d, 1H), 6.94 (d, 1H), 6.30 (s, 1H), 4.02 (s, 3H), 2.26 (s, 3H). Mass spectrum (ESI, m/z) calcd. for $C_{20}H_{15}FN_2O_3$ 350.1, found 351.1 (M+H).

EXAMPLE 76

5,6-Dichloro-3-(3-methyl-isoxazol-5-yl)-4-phenyl-1H-quinolin-2-one

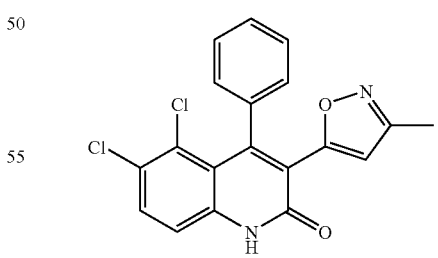

This was prepared according to Example 5 from (6-amino-2,3-dichloro-phenyl)-phenyl-methanone (J. Chem. Soc. Sec. C., 1968, (19), 2452-4). $^1$H NMR (400 MHz, $CDCl_3$+$CD_3OD$) δ 7.58 (d, 1H), 7.24 (m, 4H), 7.04 (m, 1H), 5.84 (s, 1H), 2.22 (s, 3H). Mass spectrum (ESI, m/z) calcd. for $C_{19}H_{12}Cl_2N_2O_2$ 370.1, found 371.1 (M+H).

EXAMPLE 77

6-Chloro-4-(4-ethyl-phenyl)-3-(3H-imidazol-4-yl)-1H-quinolin-2-one

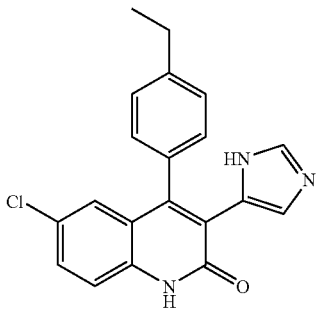

a) (2-Amino-5-chloro-phenyl)-(4-ethyl-phenyl)-methanone

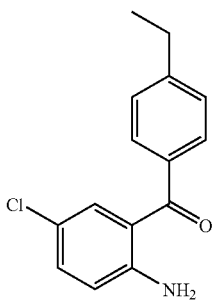

The title compound was prepared from 6-chloro-2-phenyl-benzo[d][1,3]bxazin-4-one and 4-ethylphenyl magnesium bromide according to the procedure in Example 75a in 60% yield. $^1$H NMR (400 MHz, CDCl$_3$) δ 7.61 (d, 2H), 7.42 (d, 1H), 7.30 (m, 4H), 6.72 (d, 1H), 6.01 (br s, 2H), 2.78 (q, 2H), 1.30 (t, 3H). Mass spectrum (ESI, m/z) calcd. for C$_{15}$H$_{14}$ClNO 259.1, found 260.1 (M+H).

This was prepared according to Example 5. $^1$H NMR (400 MHz, CD$_3$OD) δ 8.68 (s, 1H), 7.62 (dd, 1H), 7.48 (m, 3H), 7.22 (d, 2H), 7.12 (d, 1H), 6.42 (s, 1H), 2.82 (q, 2H), 1.36 (t, 3H). Mass spectrum (ESI, m/z) calcd. for C$_{20}$H$_{16}$ClN$_3$O 349.1, found 350.1 (M+H).

EXAMPLE 78

6-Bromo-4-(4-ethyl-phenyl)-3-(3H-imidazol-4-yl)-1H-quinolin-2-one

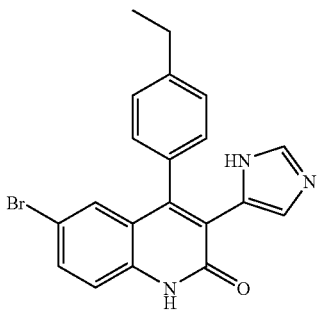

This was prepared according to example 41. $^1$H NMR (400 MHz, CD$_3$OD) δ 8.82 (s, 1H), 7.78 (dd, 1H), 7.48 (d, 2H), 7.42 (d, 1H), 7.30 (d, 1H), 7.22 (d, 2H), 6.48 (s, 1H), 2.82 (q, 2H), 1.36 (t, 3H). Mass spectrum (ESI, m/z) calcd. for C$_{20}$H$_{16}$BrN$_3$O 393.1, found 394.1 (M+H).

EXAMPLE 79

4-(4-Ethyl-phenyl)-3-(3H-imidazol-4-yl)-2-oxo-1,2-dihydro-quinoline-6-carbonitrile

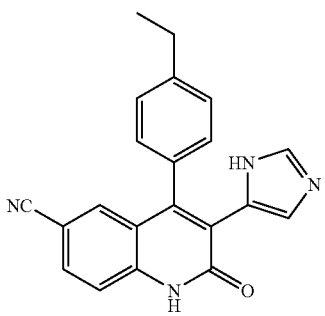

a) 4-Amino-3-(4-ethyl-benzoyl)-benzonitrile

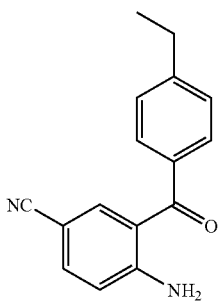

A flask charged with (2-amino-5-bromo-phenyl)-(4-ethyl-phenyl)-methanone (0.10 g, 0.32 mmol), copper cyanide (0.0347 g, 0.41 mmol), and 1 mL of DMF was heated at 180° C. for 1 hour in a microwave reactor. The title compound was eluted from a 5 g SPE with 100% DCM to give 0.07 g (81%) of a white solid. $^1$H NMR (400 MHz, CDCl$_3$) δ 7.84 (d, 1H), 7.58 (d, 2H), 7.50 (dd, 1H), 7.36 (d, 2H), 6.78 (d, 1H), 6.60 (br s, 2H), 2.78 (q, 2H), 1.30 (t, 3H).

This was prepared according to example 41. $^1$H NMR (400 MHz, CD$_3$OD) δ 8.60 (s, 1H), 7.90 (dd, 1H), 7.50 (m, 4H), 7.22 (d, 2H), 6.48 (s, 1H), 2.82 (q, 2H), 1.36 (t, 3H). Mass spectrum (ESI, m/z) calcd. for C$_{21}$H$_{16}$N$_4$O 340.1, found 341.1 (M+H).

EXAMPLE 80

6-Chloro-4-(4-ethyl-phenyl)-3-(3-methyl-isoxazlo-5-yl)-1H-quinolin-2-one

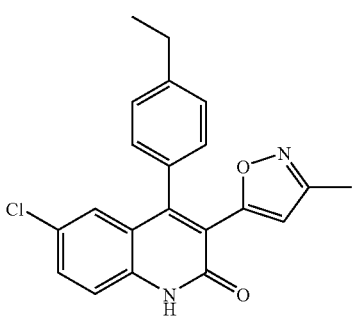

a. 2-Benzylamino-5-chloro-benzoic acid benzyl ester

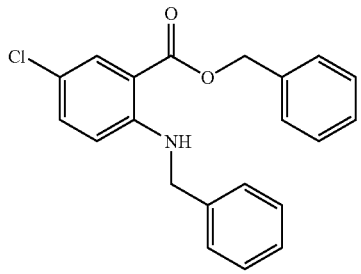

To a mixture of 5-chloroisatoic anhydride (5.00 g, 25.3 mmol) and benzylbromide (78.83 g, 50.6 mmol) in 50 ml of CH$_3$CN was added 7.57 ml of DBU (50.6 mmol) at rt under Ar. The resulting mixture was stirred at rt for 16 hr. Treated with 100 ml of EtOAc, the mixture was washed with H$_2$O, brine and dried (Na$_2$SO$_4$). Removal of the solvent in vacuo followed by flash chromatography of the residue on silica gel (10% DCM/hexanes-5% EtOAc/hexanes) gave 6.50 g (73%) of product as a brown oil.: $^1$H-NMR (CDCl$_3$; 400 MHz) 3 8.17 (t, 1H, J=5.2 Hz), 7.92 (d, 1H, J=2.8 Hz), 7.19-7.48 (m, 11H), 6.56 (d, 1H, J=9.2 Hz), 5.31 (s, 2H), 4.43 (d, 2H, J=5.2 Hz). Mass spectrum (ESI, m/z): Calcd. for C21H18ClNO2, 352.1 (M+H), found 352.0.

b. 2-{Benzyl-[2-(3-methyl-isoxazol-5-yl)-acetyl]-amino}-5-chloro-benzoic acid benzyl ester

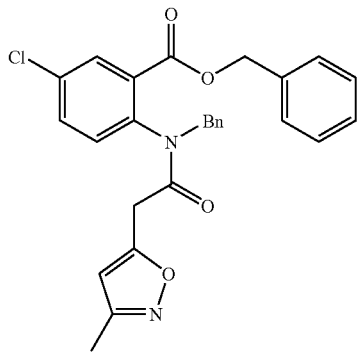

A solution of 2-benzylamino-5-chloro-benzoic acid benzyl ester (3.30 g, 9.38 mmol) and (3-methyl-isoxazol-5-yl)-acetic acid (1.39 g, 9.85 mmol) in 15 ml of POCl$_3$ was heated at 80° C. for 3 hr and then cooled to RT. Treated with 50 ml of EtOAc, the mixture was washed with H$_2$O (5×20 ml), brine (20 ml) and dried (Na$_2$SO$_4$). Removal of the solvent under reduced pressure followed by flash chromatography of the residue on silica gel (10-40% EtOAc/hexanes) gave 3.60 g (81%) of product as a brown oil: $^1$H-NMR (CDCl$_3$; 400 MHz) δ7.92 (d, 1H, J=2.5 Hz), 7.34-7.43 (m, 6H), 7.22-7.26 (m, 3H), 7.08-7.14 (m, 2H), 6.84 (d, 2H, J=8.6 Hz), 6.01 (s, 1H), 5.10-5.20 (m, 3H), 4.32 (d, 1H, J=14.2 Hz), 3.44 (d, 2H, J=1.9 Hz), 2.25 (s, 3H). Mass spectrum (ESI, m/z): Calcd. for C27H23ClN2O4, 475.1 (M+H), found 475.1.

c. 1-Benzyl-6-chloro-4-hydroxy-3-(3-methyl-isoxazol-5-yl)-1H-quinolin-2-one

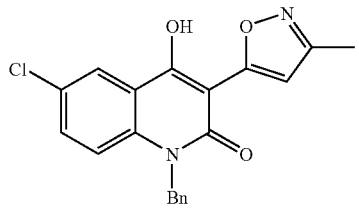

To a mixture of 2-{benzyl-[2-(3-methyl-isoxazol-5-yl)-acetyl]-amino}-5-chloro-benzoic acid benzyl ester (3.30 g, 7.58 mmol) in 25 ml of DMF at 0° C. was added NaH (340 mg). The mixture was stirred at rt for 1 h under Ar. Treated with 200 ml of EtOAc, the mixture was extracted with H$_2$O (4×50 ml). The combined aqueous layers were neutralized to pH=6 with 1N HCl and extracted with EtOAc (4×50 ml). The combined org. layers were washed with H$_2$O (2×50 ml), brine (50 ml) and dried (Na$_2$SO$_4$). Removal of the solvent under reduced pressure gave. 2.35 g (92%) of product as a white solid: $^1$H-NMR (CD$_3$OD, 400 MHz) δ 9.49 (s, 1H), 8.21 (d, 1H, J=2.6 Hz), 7.48 (dd, 1H, J=9.0, 2.6 Hz), 7.17-7.36 (m, 7H), 5.60 (s, 2H), 2.43 (s, 3H), 2.54 (s, 3H). Mass spectrum (ESI, m/z): Calcd. for C20H15ClN2O3, 367.1 (M+H), found 367.0.

d. Trifluoro-methanesulfonic acid 1-benzyl-6-chloro-3-(3-methyl-isoxazol-5-yl)-2-oxo-1,2-dihydro-quinolin-4-yl ester

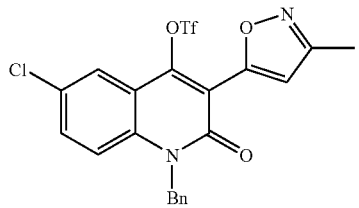

To a solution of 1-benzyl-6-chloro-4-hydroxy-3-(3-methyl-isoxazol-5-yl)-1H-quinolin-2-one (1.00 g, 2.73 mmol) and Et$_3$N (0.57 ml, 4.10 mmol) in 20 ml of DCM under at −78° C. was added Tf$_2$O (0.50 ml, 3.0 mmol) slowly under Ar. The mixture was warmed to rt. Treated with 150 ml of EtOAc, the mixture was washed with H2O (4×50 mL), brine (40 mL) and dried (Na$_2$SO$_4$). Removal of the solvent under reduced pressure gave 1.35 g (99%) of product as a light yellow solid: $^1$H-NMR (CDCl$_3$; 400 MHz) δ 7.95 (d, 1H, J=2.3 Hz), 7.55 (dd, 1H, J=9.0, 2.3 Hz), 7.27-7.37 (m, 4H), 7.21 (d, 2H, J=8.3 Hz), 7.17 (s, 1H), 5.60 (s, 2H), 2.42 (s, 3H). Mass spectrum (ESI, m/z): Calcd. for C$_{21}$H$_{14}$ClF$_3$N$_2$O$_5$S, 499.0 (M+H), found 499.0.

e. 1-Benzyl-6-chloro-4-(4-ethyl-phenyl)-3-(3-m ethyl-isoxazol-5-yl)-1H-quinolin-2-one

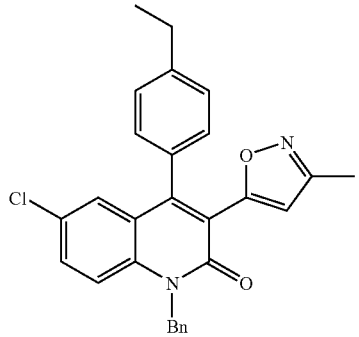

A mixture of trifluoro-methanesulfonic acid 1-benzyl-6-chloro-3-(3-methyl-isoxazol-5-yl)-2-oxo-1,2-dihydro-quinolin-4-yl ester (40 mg, 0.080 mmol), 4-ethylbenzeneboronic acid (14.4 mg, 0.096 mmol), Pd(PPh$_3$)$_4$ (9.2 mg, 0.0080 mmol) and Na$_2$CO$_3$ (80 ul, 0.16 mmol, 2.0 M) in 1 ml of 1,4-dioxane was stirred at 100° C. for 1 h, then cooled to rt. Treated with 40 ml of EtOAc, the mixture was washed with H$_2$O (2×10 ml), brine (10 mL) and dried (Na$_2$SO$_4$). Removal of the solvent under reduced pressure followed by flash chromatography of the residue on silica gel (25% EtOAc/hexane) gave 29.5 mg (81%) of product as a white solid: $^1$H-NMR (CDCl$_3$; 400 MHz) δ7.41 (dd, 1H, J=9.0, 2.2 Hz), 7.24-7.38 (m, 8H), 7.15 (d, 2H, J=8.0 Hz), 6.48 (s, 1H), 5.64 (s, 2H), 3.71 (s, 1H), 2.74 (q, 2H, J=7.6 Hz), 2.23 (s, 3H), 1.31 (t, 2H, J=7.6 Hz),. Mass spectrum (ESI, m/z): Calcd. for C$_{28}$H$_{23}$ClN$_2$O$_2$, 455.1 (M+H), found 455.1.

f. 6-Chloro-4-(4-ethyl-phenyl)-3-(3-methyl-isoxazlo-5-yl)-1H-quinolin-2-one

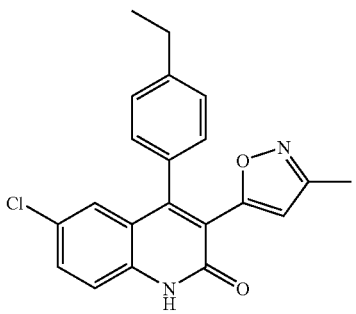

A solution of 1-benzyl-6-chloro-4-(4-ethyl-phenyl)-3-(3-methyl-isoxazol-5-yl)-1H-quinolin-2-one (29 mg, 0.064 mmol) in 1 mL of CH$_3$SO$_3$H was stirred at 100° C. for 16 h, then cooled to rt. Treated with 20 mL of H$_2$O, the mixture was neutralized to pH=7 with 2N NaOH solution and extracted with EtOAc (2×30 ml). The combined organic layers were washed with H$_2$O (10 ml), brine (10 ml) and dried (Na$_2$SO$_4$). Removal of the solvent under reduced pressure followed by flash chromatography of the residue on silica gel (40% EtOAc/DCM) gave 14 mg (60%) of product as a yellow solild: $^1$H-NMR (CDCl$_3$; 400 MHz) δ 12.0 (s, 1H), 7.51 (dd, 1H, J=8.7, 2.4 Hz), 7.36 (d, 1H, J=8.7 Hz), 7.25-7.30 (m, 3H), 7.13 (d, 2H, J=8.2 Hz), 6.40 (s, 1H), 2.74 (q, 2H, J=7.6 Hz), 2.27 (s, 3H), 1.31 (t, 2H, J=7.6 Hz), Mass spectrum (ESI, m/z): Calcd. for C$_{21}$H$_{17}$ClN$_2$O$_2$, 365.1 (M+H), found 365.1.

EXAMPLE 81

6-Chloro-3-(3-methyl-isoxazol-5-yl)-4-piperidin-1-yl-1H-quinolin-2-one

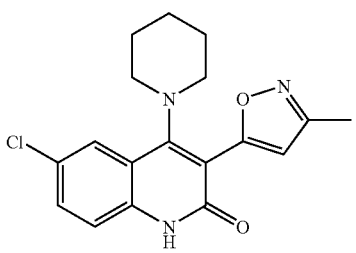

a. 1-Benzyl-6-chloro-3-(3-methyl-isoxazol-5-yl)-4-piperidin-1-yl-1H-quinolin-2-one

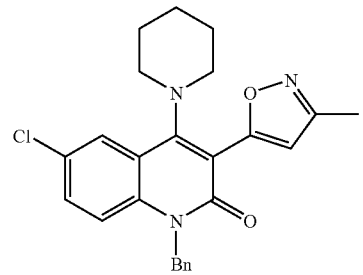

To a solution of trifluoro-methanesulfonic acid 1-benzyl-6-chloro-3-(3-methyl-isoxazol-5-yl)-2-oxo-1,2-dihydro-quinolin-4-yl ester (25 mg, 0.050 mmol) in 1 ml of THF was added piperidine (17 mg, 0.20 mmol). The mixture was stirred at rt for 16 h. Removal of the solvent under reduced pressure followed by flash chromatography of the residue on silica gel (20% EtOAc/hexanes) gave 21.0 mg (97%) of product as a yellow green oil: $^1$H-NMR (CDCl$_3$; 400 MHz) δ 7.93 (d, 1H, J=2.6 Hz), 7.37 (dd, 1H, J=9.0, 2.3 Hz), 7.18-7.33 (m, 6H), 6.56 (s, 1H), 5.50 (s, 2H), 2.99 (m, 4H), 2.40 (s, 3H), 1.64-1.76 (m, 6H). Mass spectrum (ESI, m/z): Calcd. for C$_{25}$H$_{24}$ClN$_3$O$_2$, 434.2 (M+H), found 434.1.

b. 6-Chloro-3-(3-methyl-isoxazol-5-yl)-4-piperidin-1-yl-1H-quinolin-2-one

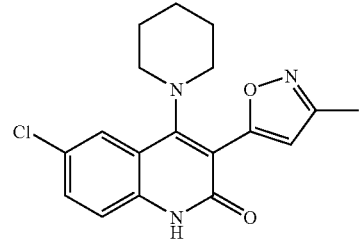

A solution of 1-benzyl-6-chloro-3-(3-methyl-isoxazol-5-yl)-4-piperidin-1-yl-1H-quinolin-2-one (21 mg, 0.048 mmol) in 1 mL of CH$_3$SO$_3$H was stirred at 110° C. for 8 h, then cooled to rt. Treated with 20 mL of H$_2$O, the mixture was neutralized to pH=7 with 2N NaOH solution and extracted with EtOAc (2×30 ml). The combined organic layers were washed with H$_2$O (10 ml), brine (10 ml) and dried (Na$_2$SO$_4$). Removal of the solvent under reduced pressure followed by flash chromatography of the residue on silica gel (20-40% EtOAc/DCM) gave 4.5 mg (27%) of product as a yellow solild: $^1$H-NMR (CDCl$_3$; 400 MHz) δ 10.9 (s, 1H), 7.83 (d, 1H, J=2.2 Hz), 7.45 (dd, 1H, J=8.6, 2.2 Hz), 7.18 (d, 1H, J=8.6 Hz), 6.50 (s, 1H), 3.00 (br s, 4H), 2.42 (s, 3H), 1.62-1.78 (m, 6H). Mass spectrum (ESI, m/z): Calcd. for C$_{18}$H$_{18}$ClN$_3$O$_2$, 344.1 (M+H), found 344.1.

EXAMPLE 82

6-Chloro-4-cyclohexyl-3-(3-methyl-isoxazol-5-yl)-1H-quinolin-2-one

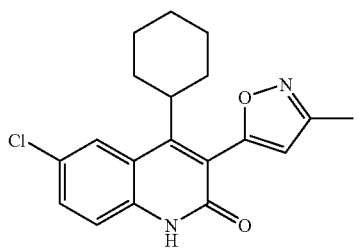

a. 1-Benzyl-6-chloro-4-cyclohexyl-3-(3-methyl-isoxazol-5-yl)-1H-quinolin-2-one

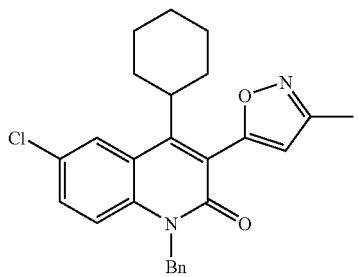

A solution of cyclohexylmagnesium chloride (250 ul, 0.50 mmol, 2M in THF) was added to a suspension of cupper (I) bromide-dimethylsulfide (51 mg, 0.25 mmol) in 2 ml of THF at −78° C. under $N_2$. The mixture was warmed to rt until a dark color homogenous solution was observed (ca. 15 min), then re-cooled to −78° C. A solution of trifluoro-methanesulfonic acid 1-benzyl-6-chloro-3-(3-methyl-isoxazol-5-yl)-2-oxo-1,2-dihydro-quinolin-4-yl ester (80 mg, 0.16 mmol) in 2 ml of THF was added to the mixture. The resulting mixture was stirred at −78° C. for 2 h and warmed to rt. Treated with 2 ml of sat. $NH_4Cl$ followed by 20 ml $H_2O$, the mixture was extracted with EtOAc (2×20 ml). The combined organic layers were washed with $H_2O$ (10 ml), brine (10 ml) and dried ($Na_2SO_4$). Removal of the solvent under reduced pressure followed by flash chromatography of the residue on silica gel (20-30% EtOAc/hexanes) gave 61 mg (88%) of product as a white solid: $^1$H-NMR (CDCl$_3$; 400 MHz) δ8.08 (br s, 1H), 7.40 (dd, 1H, J=9.2, 2.2 Hz), 7.20-7.34 (m, 6H), 6.42 (s, 1H), 5.53 (s, 2H), 2.98 (br s, 1H), 2.41 (s, 3H), 1.67-1.93 (m, 7H), 1.22-1.40 (m, 3H). Mass spectrum (ESI, m/z): Calcd. for $C_{26}H_{25}ClN_2O_2$, 433.2 (M+H), found 433.1.

b. 6-Chloro-4-cyclohexyl-3-(3-methyl-isoxazol-5-yl)-1H-quinolin-2-one

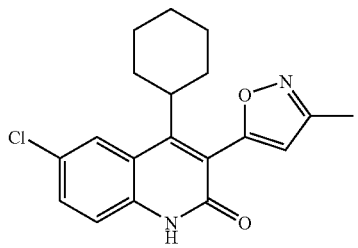

A solution of 1-benzyl-6-chloro-4-cyclohexyl-3-(3-methyl-isoxazol-5-yl)-1H-quinolin-2-one in 1 mL of $CH_3SO_3H$ was stirred at 110° C. for 4 h, then cooled to rt. Treated with 20 ml of $H_2O$, the mixture was neutralized to pH=7 with 2N NaOH solution and extracted with EtOAc (2×20 ml). The combined organic layers were washed with $H_2O$ (10 ml), brine (10 ml) and dried ($Na_2SO_4$). Removal of the solvent under reduced pressure followed by flash chromatography of the residue on silica gel (20-40% EtOAc/DCM) gave 25 mg (61%) of product as a white solild: $^1$H-NMR (CDCl$_3$; 400 MHz) δ 12.5 (s, 1H), 8.04 (br s, 1H), 7.47 (dd, 1H, J=8.8, 1.9 Hz), 7.28 (d, 1H, J=8.8 Hz), 6.38 (s, 1H), 2.94 (br s, 1H), 2.45 (s, 3H), 1.71-1.97 (m, 7H), 1.11-1.40 (m, 3H). Mass spectrum (ESI, m/z): Calcd. for C19H19ClN2O2, 343.1 (M+H), found 343.1.

EXAMPLE 83

4-Cyclohept-1-enyl-3-(3-methyl-isoxazol-5-yl)-2-oxo-1,2-dihydro-quinoline-6-carbonitrile

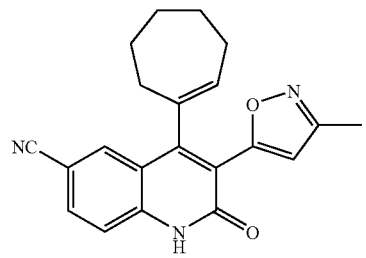

a. 2-Amino-5-cyano-benzoic acid methyl ester

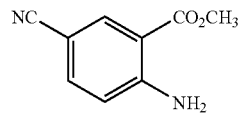

A mixture of 2-amino-5-bromo-benzoic acid methyl ester (5.00 g, 21.7 mmol) and CuCN (2.34 g, 26.1 mmol, 2.0 M) in 25 ml of NMP was stirred at reflux for 5 h, then cooled to rt. The mixture was poured into a solution of hydrated FeCl$_3$ (15 g of FeCl$_3$.6H$_2$O) and conc. HCl (2.2 ml) in 15 ml of H$_2$O. The resulting mixture was stirred at 60° C. for 1 h, cooled to rt. Treated with 200 ml of EtOAc, the mixture was washed with H$_2$O (40 ml), 1N NaOH (3×30 ml), brine (30 ml) and dried (Na$_2$SO$_4$). Removal of the solvent under reduced pressure gave a slightly dark solid. Recrystalization of the solid in hexanes/DCM/EtOAc yielded 3.25 g (85%) of product as a yellow solid: $^1$H-NMR (CDCl$_3$; 400 MHz) δ 8.20 (d, 1H, J=1.9 Hz), 7.45 (dd, 1H, J=8.9, 1.9 Hz), 6.67 (d, 1H, J=8.9 Hz), 6.29 (br s, 2H), 3.90 (s, 3H). Mass spectrum (ESI, m/z): Calcd. for $C_9H_8N_2O_2$, 177.1 (M+H), found 177.2.

b. 5-Cyano-2-[2-(3-methyl-isoxazol-5-yl)-acetylamino]-benzoic acid methyl ester

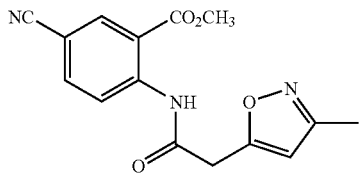

A solution of 2-amino-5-cyano-benzoic acid methyl ester (1.50 g, 8.51 mmol) and (3-methyl-isoxazol-5-yl)-acetic acid (1.32 g, 9.36 mmol) in 40 ml of POCl₃ was heated at 80° C. for 2 hr and then cooled to RT. Treated with 50 mL of EtOAc, the mixture was washed with H₂O (3×40 ml), sat. NaHCO₃ (40 ml), brine (40 ml) and dried (Na₂SO₄). Removal of the solvent under reduced pressure gave 2.31 g (91%) of product as a light yellow solid: $^1$H-NMR (CDCl₃; 400 MHz) δ 11.49 (s, 1H), 8.85 (d, 1H, J=8.8 Hz), 8.35 (d, 1H, J=2.0 Hz), 7.79 (dd, 1H, J=8.8, 2.0 Hz), 6.20 (s, 1H), 3.97 (s, 3H), 3.95 (s, 2H), 2.33 (s, 3H). Mass spectrum (ESI, m/z): Calcd. for $C_{15}H_{13}N_3O_4$, 300.1 (M+H), found 299.9.

c. Trifluoro-methanesulfonic acid 6-cyano-3-(3-methyl-isoxazol-5-yl)-2-oxo-1,2-dihydro-quinolin-4-yl ester

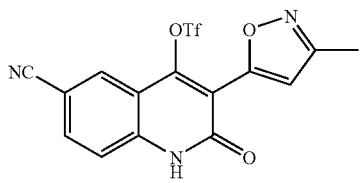

To a mixture of 5-cyano-2-[2-(3-methyl-isoxazol-5-yl)-acetylamino]-benzoic acid methyl ester (1.00 g, 3.34 mmol) in 30 ml of DMSO at rt was added KO'Bu (809 mg, 6.85 mmol). The mixture was stirred at rt for 15 min under Ar, N-phenyltrifluoromethanesufonimide (2.53 g, 7.02 mmol) was added. The mixture was stirred at rt for 1 h. Treated with 150 ml of EtOAc, the mixture was washed with H₂O (2×50 ml). The combined aqueous layers were extracted with EtOAc (2×30 ml). The combined org. layers were washed with H₂O (2×50 ml), brine (50 ml) and dried (Na₂SO₄). Removal of the solvent under reduced pressure followed by flash chromatography of the residue on silica gel (10-25% EtOAc/DCM) gave 670 mg (50%) of product as a white solid: $^1$H-NMR (CD₃OD, 400 MHz) δ8.20 (d, 1H, J=1.7 Hz), 7.99 (dd, 1H, J=8.6, 1.7 Hz), 7.56 (d, 1H, J=8.6 Hz), 7.17 (s, 1H), 2.40 (s, 3H). Mass spectrum (ESI, m/z): Calcd. for $C_{15}H_8F_3N_3O_5S$, 400.0 (M+H), found 399.9.

d. 4-Cyclohept-1-enyl-3-(3-methyl-isoxazol-5-yl)-2-oxo-1,2-dihydro-quinoline-6-carbonitrile

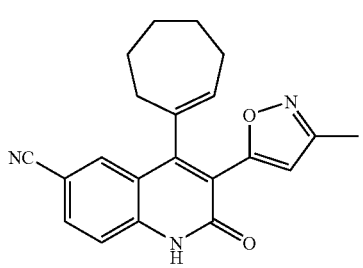

A mixture of trifluoro-methanesulfonic acid 6-cyano-3-(3-methyl-isoxazol-5-yl)-2-oxo-1,2-dihydro-quinolin-4-yl ester (30 mg, 0.075 mmol), cyclohepten-1-ylboronic acid (12.6 mg, 0.090 mmol), Pd(PPh₃)₄ (8.7 mg, 0.0075 mmol) and Na₂CO₃ (375 ul, 0.75 mmol, 2.0 M) in 1 ml of 1,4-dioxane was stirred at 80° C. for 1 h, then cooled to rt. Treated with 20 ml of H₂O, the mixture was acidified to PH=7 with 1N HCl and then extracted with EtOAc (3×15 ml). The combined organic layers were washed with H₂O (20 ml), brine (15 ml) and dried (Na₂SO₄). Removal of the solvent under reduced pressure followed by flash chromatography of the residue on silica gel (10-20% EtOAc/DCM) gave 15.1 mg (58%) of product as a white solid: $^1$H-NMR (CDCl₃; 400 MHz) δ 12.3 (s, 1H), 8.08 (d, 1H, J=1.7 Hz), 7.77 (dd, 1H, J=8.6, 1.7 Hz), 7.43 (d, 1H, J=8.6 Hz), 6.70 (s, 1H), 5.79 (t, 1H, J=6.1 Hz), 2.44 (s, 3H), 2.26-2.52 (m, 4H), 1.62-1.94 (m, 6H). Mass spectrum (ESI, m/z): Calcd. for C21H19N3O2, 346.2 (M+H), found 346.1.

EXAMPLE 84

6-Chloro-3-(3-methyl-isoxazol-5-yl)-4-m-tolyl-1H-quinolin-2-one

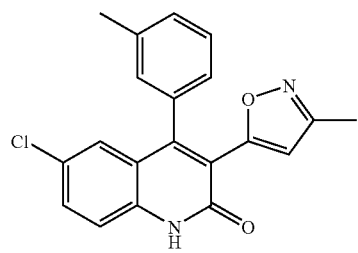

Prepared according to the procedure described for Example 80.

EXAMPLE 85

6-Chloro-3-(3-methyl-isoxazol-5-yl)-4-p-tolyl-1H-quinolin-2-one

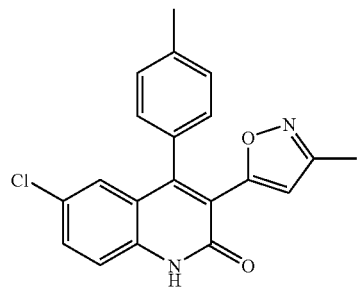

Prepared according to the procedure described for Example 80.

EXAMPLE 86

6-Chloro-3-(3-methyl-isoxazol-5-yl)-4-o-tolyl-1H-quinolin-2-one

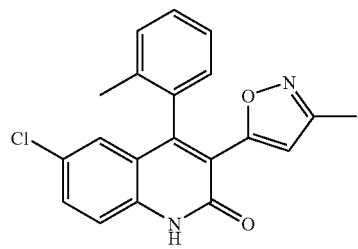

Prepared according to the procedure described for Example 80.

EXAMPLE 87

6-Chloro-4-(2-chloro-phenyl)-3-(3-methyl-isoxazol-5-yl)-1H-quinolin-2-one

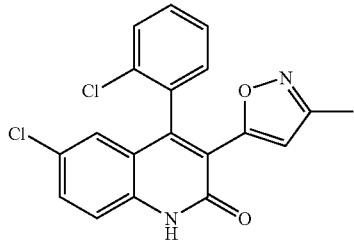

Prepared according to the procedure described for Example 80.

EXAMPLE 88

6-Chloro-4-(4-chloro-phenyl)-3-(3-methyl-isoxazol-5-yl)-1H-quinolin-2-one

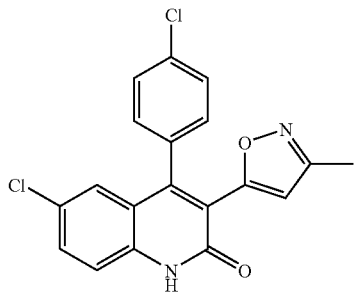

Prepared according to the procedure described for Example 80.

EXAMPLE 89

4-(4-Acetyl-3-hydroxy-phenyl)-6-chloro-3-(3-methyl-isoxazol-5-yl)-1H-quinolin-2-one

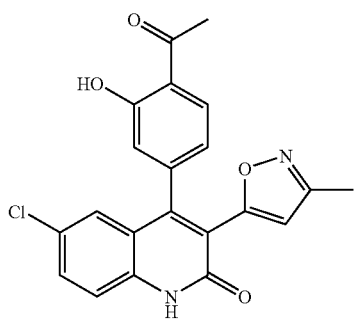

Prepared according to the procedure described for Example 80.

EXAMPLE 90

4-(3-Acetyl-4-hydroxy-phenyl)-6-chloro-3-(3-methyl-isoxazol-5-yl)-1H-quinolin-2-one

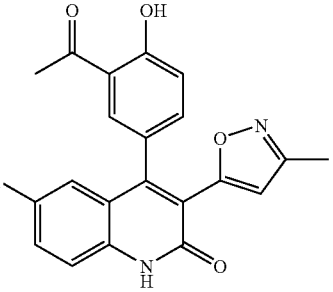

Prepared according to the procedure described for Example 80.

EXAMPLE 91

6-Chloro-4-(4-hydroxy-phenyl)-3-(3-methyl-isoxazol-5-yl)-1H-quinolin-2-one

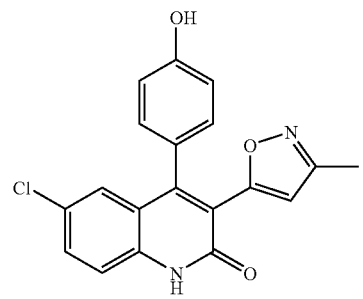

Prepared according to the procedure described for Example 80.

EXAMPLE 92

4-(5-Acetyl-2-methoxy-phenyl)-6-chloro-3-(3-methyl-isoxazol-5-yl)-1H-quinolin-2-one

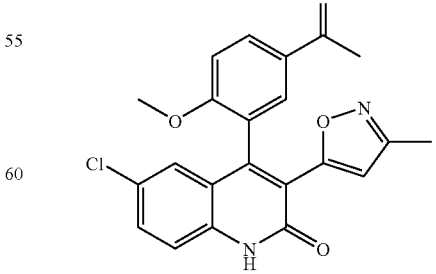

Prepared according to the procedure described for Example 80.

EXAMPLE 93

4-(5-Acetyl-2-hydroxy-phenyl)-6-chloro-3-(3-methyl-isoxazol-5-yl)-1H-quinolin-2-one

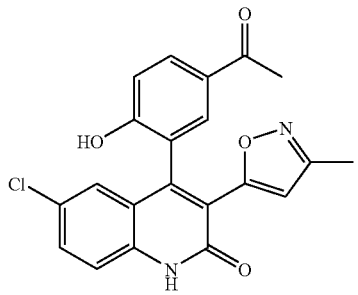

Prepared according to the procedure described for Example 80.

EXAMPLE 94

6-Chloro-4-(2-methoxy-phenyl)-3-(3-methyl-isoxazol-5-yl)-1H-quinolin-2-one

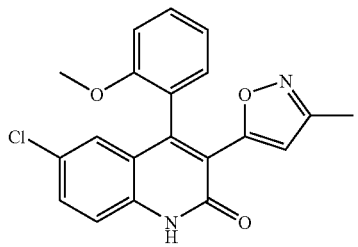

Prepared according to the procedure described for Example 80.

EXAMPLE 95

6-Chloro-4-(4-methoxy-phenyl)-3-(3-methyl-isoxazol-5-yl)-1H-quinolin-2-one

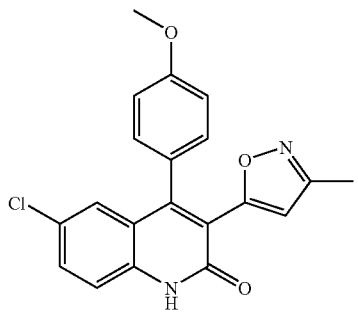

Prepared according to the procedure described for Example 80.

EXAMPLE 96

6-Chloro-4-(2-hydroxy-phenyl)-3-(3-methyl-isoxazol-5-yl)-1H-quinolin-2-one

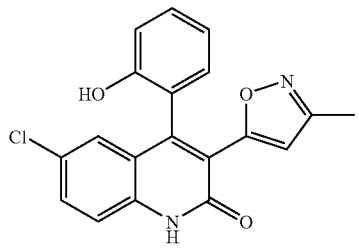

Prepared according to the procedure described for Example 80.

EXAMPLE 97

6-Chloro-4-(3-methoxy-phenyl)-3-(3-methyl-isoxazol-5-yl)-1H-quinolin-2-one

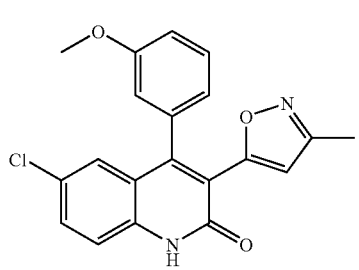

Prepared according to the procedure described for Example 80.

EXAMPLE 98

6-Chloro-3-(3-methyl-isoxazol-5-yl)-4-naphthalen-1-yl-1H-quinolin-2-one

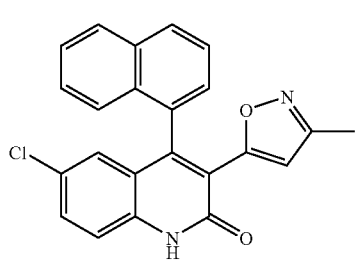

Prepared according to the procedure described for Example 80.

EXAMPLE 99

6-Chloro-3-(3-methyl-isoxazol-5-yl)-4-naphthalen-2-yl-1H-quinolin-2-one

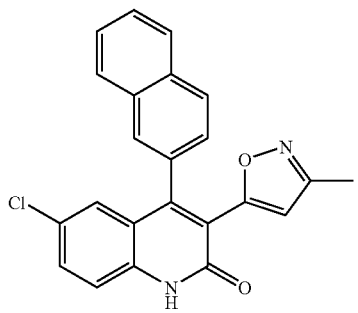

Prepared according to the procedure described for Example 80.

EXAMPLE 100

6-Chloro-4-(4-fluoro-phenyl)-3-(3-methyl-isoxazol-5-yl)-1H-quinolin-2-one

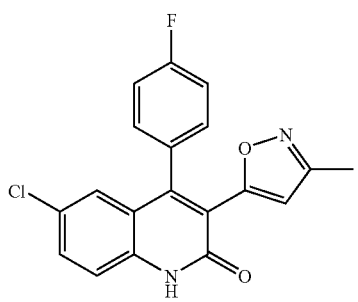

Prepared according to the procedure described for Example 80.

EXAMPLE 101

4-Biphenyl-4-yl-6-chloro-3-(3-methyl-isoxazol-5-yl)-1H-quinolin-2-one

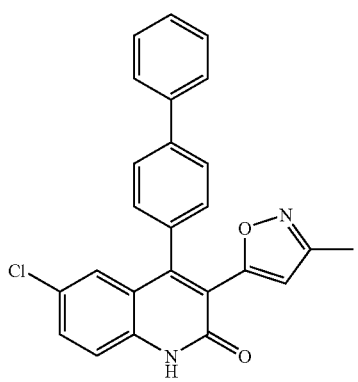

Prepared according to the procedure described for Example 80.

EXAMPLE 102

6-Chloro-4-cyclohex-1-enyl-3-(3-methyl-isoxazol-5-yl)-1H-quinolin-2-one

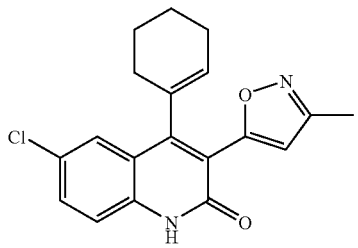

Prepared according to the procedure described for Example 80.

EXAMPLE 103

6-Chloro-4-furan-2-yl-3-(3-methyl-isoxazol-5-yl)-1H-quinolin-2-one

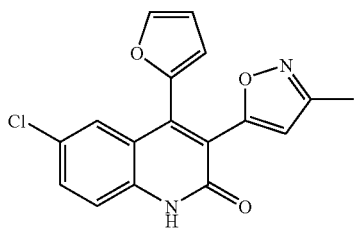

Prepared according to the procedure described for Example 80.

EXAMPLE 104

6-Chloro-3-(3-methyl-isoxazol-5-yl)-4-thiophen-2-yl-1H-quinolin-2-one

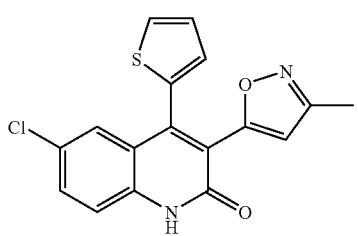

Prepared according to the procedure described for Example 80.

EXAMPLE 105

4-Benzofuran-2-yl-6-chloro-3-(3-methyl-isoxazol-5-yl)-1H-quinolin-2-one

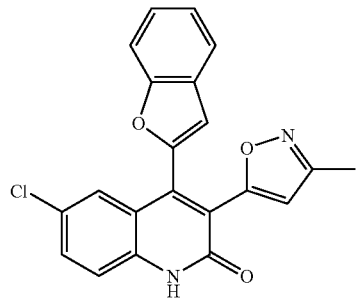

Prepared according to the procedure described for Example 80.

EXAMPLE 106

3-[6-Chloro-3-(3-methyl-isoxazol-5-yl)-2-oxo-1,2-dihydro-quinolin-4-yl]-benzoic acid

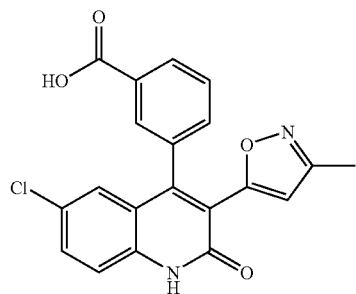

Prepared according to the procedure described for Example 80.

EXAMPLE 107

6-Chloro-3-(3-methyl-isoxazol-5-yl)-4-morpholin-4-yl-1H-quinolin-2-one

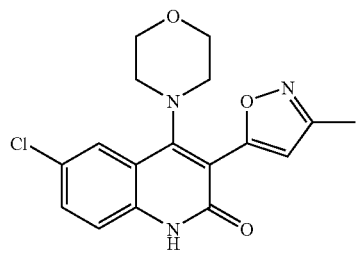

Prepared according to the procedure described for Example 81.

EXAMPLE 108

6-Chloro-3-(3-methyl-isoxazol-5-yl)-4-(4-methyl-piperazin-1-yl)-1H-quinolin-2-one

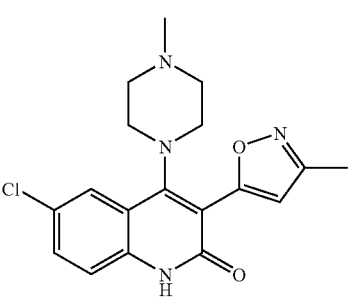

Prepared according to the procedure described for Example 81.

EXAMPLE 109

6-Chloro-3-(3-methyl-isoxazol-5-yl)-4-(4-methyl-piperidin-1-yl)-1H-quinolin-2-one

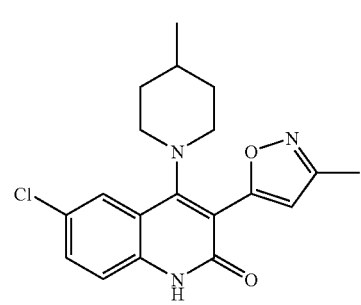

Prepared according to the procedure described for Example 81.

EXAMPLE 110

6-Chloro-4-imidazol-1-yl-3-(3-methyl-isoxazol-5-yl)-1H-quinolin-2-one

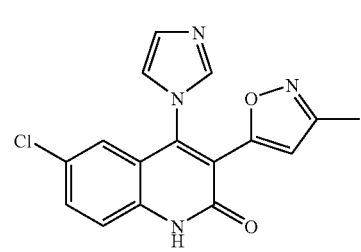

Prepared according to the procedure described for Example 81.

EXAMPLE 111

4-Benzo[b]thiophen-2-yl-6-chloro-3-(3-methyl-isoxazol-5-yl)-1H-quinolin-2-one

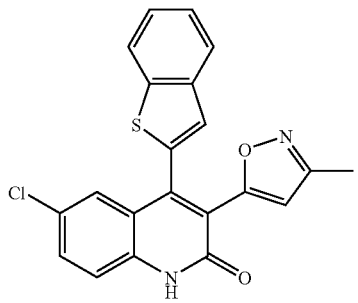

Prepared according to the procedure described for Example 81.

EXAMPLE 112

6-Chloro-4-cyclohept-1-enyl-3-(3-methyl-isoxazol-5-yl)-1H-quinolin-2-one

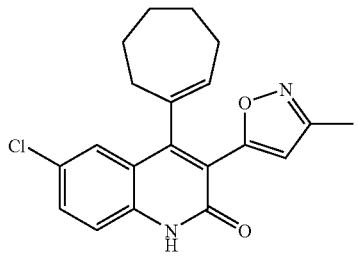

Prepared according to the procedure described for Example 80.

EXAMPLE 113

6-Chloro-3-(3-methyl-isoxazol-5-yl)-4-(4-propyl-piperidin-1-yl)-1H-quinolin-2-one

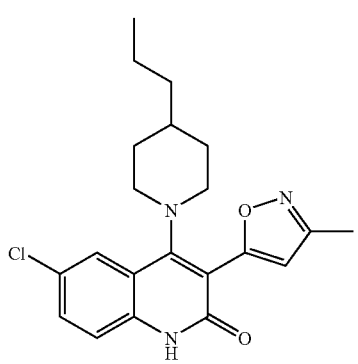

Prepared according to the procedure described for Example 81.

EXAMPLE 114

6-Chloro-3-(3-methyl-isoxazol-5-yl)-4-(3-methyl-piperidin-1-yl)-1H-quinolin-2-one

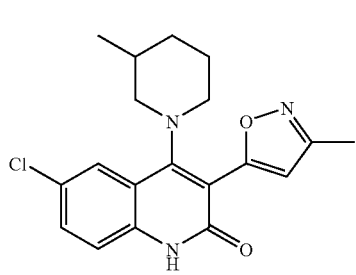

Prepared according to the procedure described for Example 81.

EXAMPLE 115

6-Chloro-4-cycloheptyl-3-(3-methyl-isoxazol-5-yl)-1H-quinolin-2-one

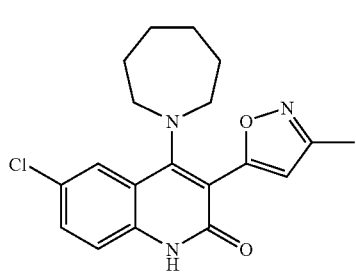

Prepared according to the procedure described for Example 81.

EXAMPLE 116

6-Chloro-4-(4,4-dimethyl-piperidin-1-yl)-3-(3-methyl-isoxazol-5-yl)-1H-quinolin-2-one

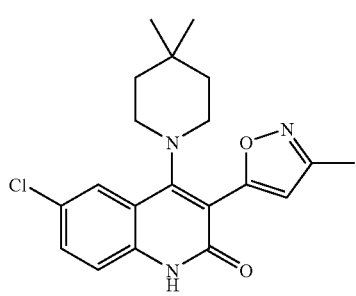

Prepared according to the procedure described for Example 81.

EXAMPLE 117

4-(4-tert-Butyl-phenyl)-6-chloro-3-(3-methyl-isoxazol-5-yl)-1H-quinolin-2-one

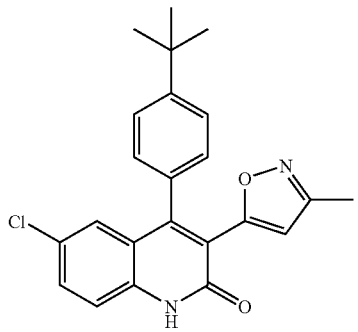

Prepared according to the procedure described for Example 80.

EXAMPLE 118

6-Chloro-3-(3-methyl-isoxazol-5-yl)-4-(4-propyl-phenyl)-1H-quinolin-2-one

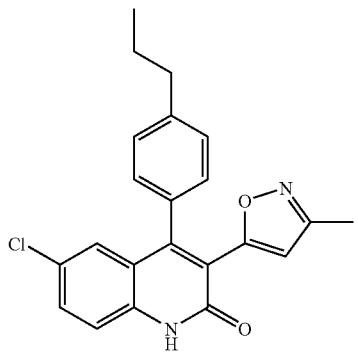

Prepared according to the procedure described for Example 80.

EXAMPLE 119

6-Chloro-4-(4-isopropyl-phenyl)-3-(3-methyl-isoxazol-5-yl)-1H-quinolin-2-one

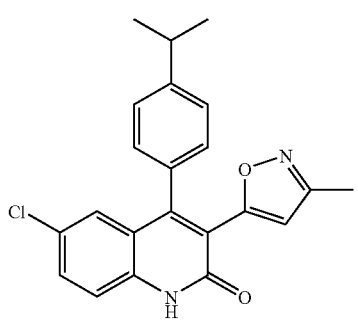

Prepared according to the procedure described for Example 80.

EXAMPLE 120

6-Bromo-4-(4-ethyl-phenyl)-3-(3-methyl-isoxazol-5-yl)-1H-quinolin-2-one

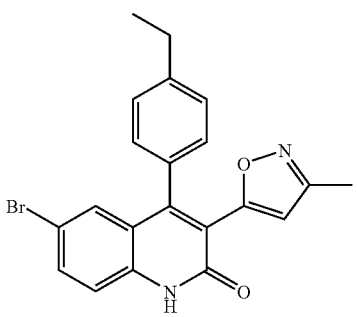

Prepared according to the procedure described for Example 41.

EXAMPLE 121

4-(4-Ethyl-phenyl)-3-(3-methyl-isoxazol-5-yl)-2-oxo-1,2-dihydro-quinoline-6-carbonitrile

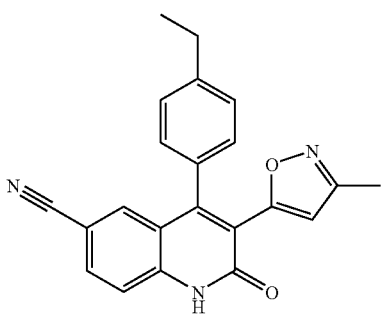

Prepared according to the procedures described for examples 83 and 79.

EXAMPLE 122

4-(4-tert-Butyl-phenyl)-3-(3-methyl-isoxazol-5-yl)-2-oxo-1,2-dihydro-quinoline-6-carbonitrile

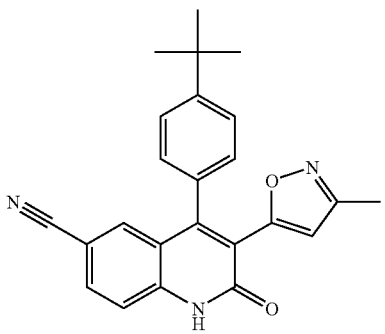

Prepared according to the procedure described for Example 83.

EXAMPLE 123

3-(3-Methyl-isoxazol-5-yl)-2-oxo-4-(4-propyl-phenyl)-1,2-dihydro-quinoline-6-carbonitrile

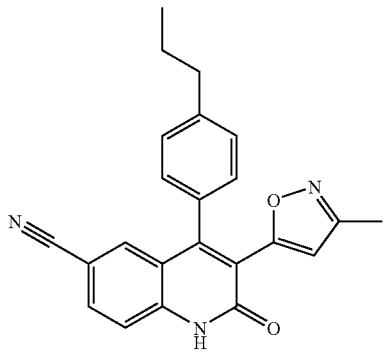

Prepared according to the procedure described for Example 83.

EXAMPLE 124

4-(4-Isopropyl-phenyl)-3-(3-methyl-isoxazol-5-yl)-2-oxo-1,2-dihydro-quinoline-6-carbonitrile

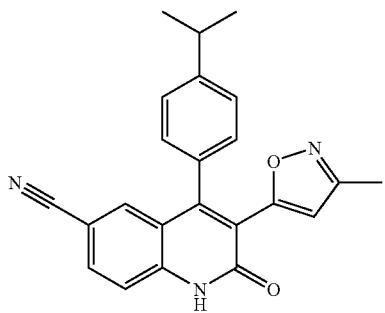

Prepared according to the procedure described for Example 83.

EXAMPLE 125

3-(3-Methyl-isoxazol-5-yl)-2-oxo-4-(4-trifluoromethyl-phenyl)-1,2-dihydro-quinoline-6-carbonitrile

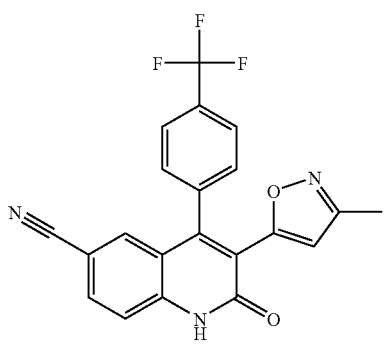

Prepared according to the procedure described for Example 83.

EXAMPLE 126

4-(4-Acetyl-phenyl)-3-(3-methyl-isoxazol-5-yl)-2-oxo-1,2-dihydro-quinoline-6-carbonitrile

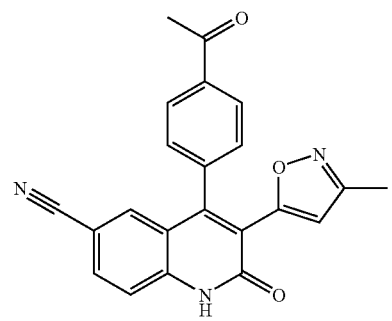

Prepared according to the procedure described for Example 83.

EXAMPLE 127

3-(3-Methyl-isoxazol-5-yl)-4-(4-methylsulfanyl-phenyl)-2-oxo-1,2-dihydro-quinoline-6-carbonitrile

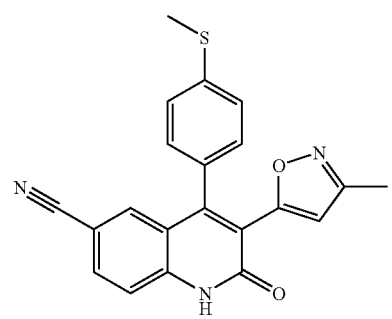

Prepared according to the procedure described for Example 83.

EXAMPLE 128

3-(3-Methyl-isoxazol-5-yl)-2-oxo-4-(4-vinyl-phenyl)-1,2-dihydro-quinoline-6-carbonitrile

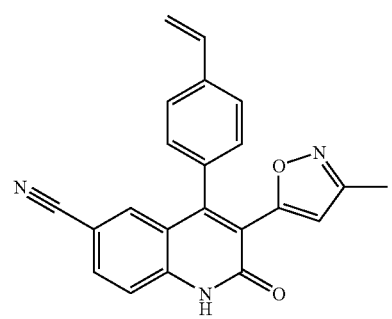

Prepared according to the procedure described for Example 83.

EXAMPLE 129

4-(4-Ethyl-phenyl)-3-(2-methyl-thiazol-4-yl)-2-oxo-1,2-dihydro-quinoline-6-carbonitrile

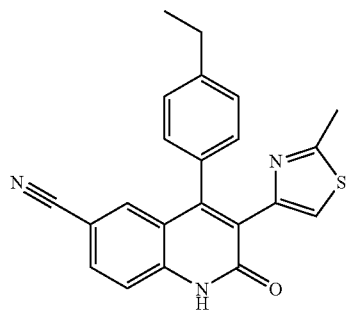

Prepared according to the procedure described for Example 83.

EXAMPLE 130

3-(3-Methyl-isoxazol-5-yl)-2-oxo-4-(4-trifluoromethoxy-phenyl)-1,2-dihydro-quinoline-6-carbonitrile

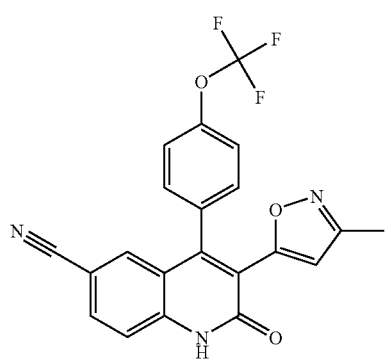

Prepared according to the procedure described for Example 83.

EXAMPLE 131

4-(4-Cyano-phenyl)-3-(3-methyl-isoxazol-5-yl)-2-oxo-1,2-dihydro-quinoline-6-carbonitrile

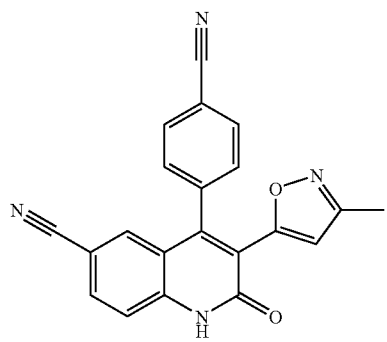

Prepared according to the procedure described for Example 83.

EXAMPLE 132

4-(4-Methanesulfonyl-phenyl)-3-(3-methyl-isoxazol-5-yl)-2-oxo-1,2-dihydro-quinoline-6-carbonitrile

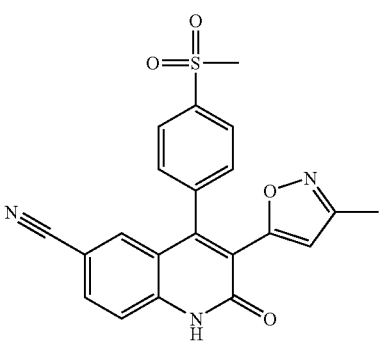

Prepared according to the procedure described for Example 83.

EXAMPLE 133

6-Bromo-3-(3-methyl-isoxazol-5-yl)-4-phenyl-1H-quinoline-2-thione

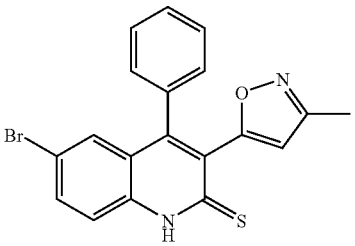

A flask charged with (2-amino-5-bromo-phenyl)-phenyl-methanone (0.69 g, 2.5 mmol), (3-methyl-isoxazol-5-yl)-acetic acid (0.35 g, 2.5 mmol), and 5 mL of phosphorus oxychloride was heated to 80° C. for 6 hrs. The reaction was concentrated and triturated with saturated $NaHCO_3$ to give 0.6 g of a 6-bromo-2-chloro-3-(5-methyl-isoxazol-3-yl)-4-phenyl-quinoline. Solution of the preceding compound in 20 mL of ethanol was followed by treatment with thiourea (0.12 g, 1.6 mmol) and the solution heated to 80° C. for 3 hrs. The solution was concentrated and the title compound purified by flash chromatography to give 0.06 g (50%) of a white solid. $^1$H NMR (400 MHz, $CDCl_3$) δ 12.92 (s, 1H); 7.72 (dd, 1H), 7.56 (d, 1H), 7.42 (m, 4H), 7.20 (m, 2H), 6.00 (s, 1H), 2.24 (s, 3H). Mass spectrum (ESI, m/z) calcd. for $C_{19}H_{13}BrN_2OS$ 396.0, found 397.0 (M+H).

EXAMPLE 134

6-Bromo-3-(3H-imidazol-4-yl)-4-phenyl-1H-quinolin-2-one

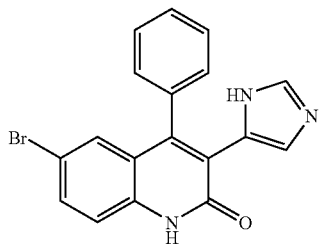

Prepared according to the procedure described for Example 41. $^1$H NMR (400 MHz, CD$_3$OD) δ7.60 (m, 5H), 7.38 (d, 1H), 7.28 (m, 2H), 7.18 (m, 1H), 5.90 (br s, 1H). Mass spectrum (ESI, m/z) calcd. for C$_{18}$H$_2$BrN$_3$O 365.1, found 366.2 (M+H).

EXAMPLE 135

6-Bromo-3-(3H-imidazol-4-yl)-1-methyl-4-phenyl-1H-quinolin-2-one

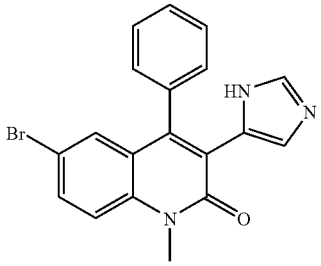

A flask containing 6-bromo-3-(3H-imidazol-4-yl)-4-phenyl-1H-quinolin-2-one (23 mg, 0.063 mmol) (Example 134), K$_2$CO$_3$ (30 mg, 0.22 mmol), methyl iodide (4 μL, 0.063 mmol) and 0.1 mL of DMF was stirred at 25° C. for 3 hrs. The compound was purified by RP-HPLC, eluting with 30-70% CH$_3$CN in 0.1% TFA/H$_2$O over 20 mins to give 13 mg (42%) the title compound as a TFA salt. $^1$H NMR (400 MHz, CD$_3$OD) δ 8.82 (s, 1H), 7.90 (dd, 1H), 7.70 (d, 1H), 7.62 (m, 3H), 7.34 (m, 3H), 6.60 (s, 1H), 3.92 (s, 3H). Diff Noe, irradiation at 3.92 ppm (N—CH$_3$) enhanced 7.70 ppm (d, 1H, H-8). Mass spectrum (ESI, m/z) calcd. for C$_{19}$H$_1$BrN$_3$O$_2$ 379.0, found 380.0 (M+H).

TABLE 1 lists LC and mass spectral data of selected compounds of the present invention:

| Structure | Name | Data |
|---|---|---|
| 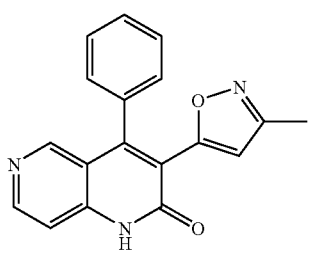 | 3-(3-Methyl-isoxazol-5-yl)-4-phenyl-1H-[1,6]naphthyridin-2-one | LC 1.35<br>[M+H]$^+$ Expected for C$_{18}$H$_{13}$N$_3$O$_2$: 304.1<br>Observed: 304.1 |
| 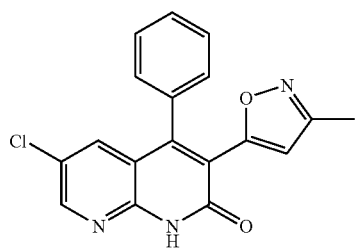 | 6-Chloro-3-(3-Methyl-isoxazol-5-yl)-4-phenyl-1H-[1,8]naphthyridin-2-one | LC 2.61<br>[M+H]$^+$ Expected for C$_{18}$H$_{12}$ClN$_3$O$_2$: 338.1<br>Observed: 338.1, 340.1 |
| 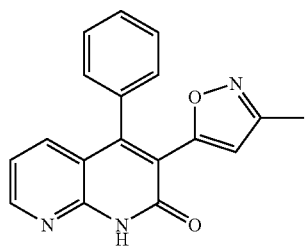 | 3-(3-Methyl-isoxazol-5-yl)-4-phenyl-1H-[1,8]naphthyridin-2-one | LC 2.24<br>[M+H]$^+$ Expected for C$_{18}$H$_{13}$N$_3$O$_2$: 304.1<br>Observed: 304.1 |

TABLE 1-continued lists LC and mass spectral data of selected compounds of the present invention:

| Structure | Name | Data |
|---|---|---|
| | 3-(3-Methyl-isoxazol-5-yl)-4-phenyl-1H-[1,7]naphthyridin-2-one | LC 1.81<br>[M+H]+ Expected for C$_{18}$H$_{13}$N$_3$O$_2$: 304.1<br>Observed: 304.1 |
| | 3-(3-Methyl-isoxazol-5-yl)-4-phenyl-1H-[1,5]naphthyridin-2-one | LC 1.93<br>[M+H]+ Expected for C$_{18}$H$_{13}$N$_3$O$_2$: 304.1<br>Observed: 304.1 |
| | 6-Bromo-3-(3-Methyl-isoxazol-5-yl)-4-phenyl-1H-[1,8]naphthyridin-2-one | LC 2.67<br>[M+H]+ =<br>384.0 and 385.0 |
| | 6-Chloro-3-(3-Methyl-isoxazol-5-yl)-4-phenyl-1H-[1,8]naphthyridin-2-one | LC 2.50<br>[M+H]+ =<br>338.1 and 340.1 |
| | 3-Methyl-benzo[b]thiophen-2-yl-6-chloro-4-phenyl-1H-quinolin-2-one | LC 3.62<br>[M+H]+ =<br>402.1 and 404.1 |
| | 6-Chloro-4-phenyl-3-thiophen-2-yl-1H-quinolin-2-one | LC 3.26<br>[M+H]+ =<br>338.1 and 340.1 |

TABLE 1-continued lists LC and mass spectral data of selected compounds of the present invention:

| Structure | Name | Data |
|---|---|---|
| 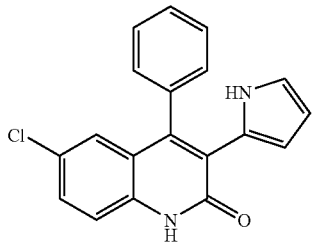 | 6-Chloro-4-phenyl-3-(1H-pyrrol)-2-yl-1H-quinolin-2-one | LC 3.29 [M+H]$^+$ = 321.1 and 323.1 |
| 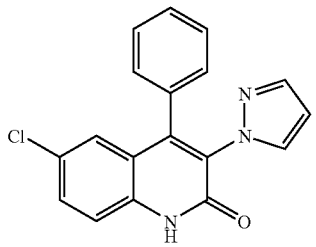 | 6-Chloro-4-phenyl-3-pyrazol-1-yl-1H-quinolin-2-one | LC 2.49 [M+H]$^+$ = 322.1 and 324.1 |
| 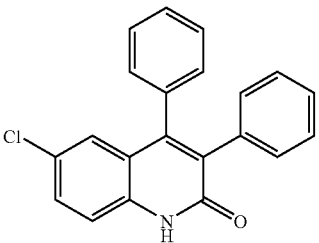 | 6-Chloro-3,4-diphenyl-1H-quinolin-2-one | LC 3.20 [M+H]$^+$ = 332.2 and 334.2 |
| 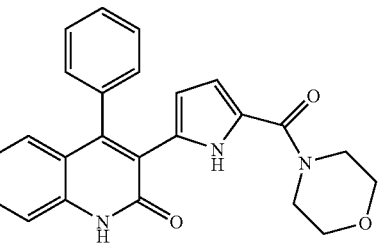 | 6-Chloro-3-[(5-morpholine-4-carbonyl)1H-pyrrol-2-yl]-4-phenyl-1H-quinolin-2-one | LC 3.03 [M+H]$^+$ = 434.0 and 436.0 |
| 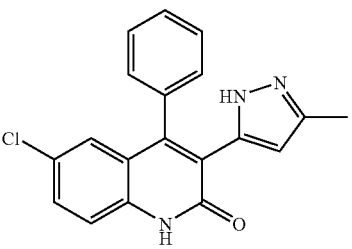 | 6-Chloro-3-(5-methyl-2H-pyrazol-3-yl)-4-phenyl-1H-quinolin-2-one | LC 2.36 [M+H]$^+$ = 336.2 and 338.2 |
| 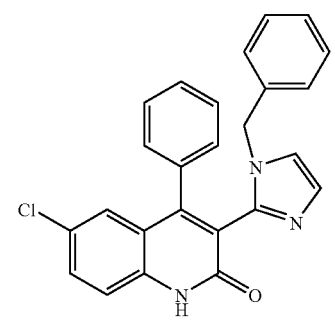 | 3-(1-Benzyl-1H-imidazol-2-yl)-6-Chloro-4-phenyl-1H-quinolin-2-one | LC 2.18 [M+H]$^+$ = 412.2 and 414.2 |

TABLE 1-continued lists LC and mass spectral data of selected compounds of the present invention:

| Structure | Name | Data |
|---|---|---|
| 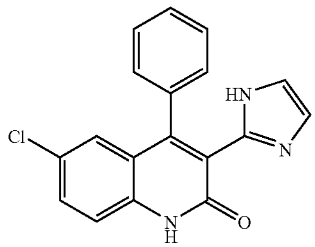 | 6-Chloro-3-(1H-imidazol-2-yl)-4-phenyl-1H-quinolin-2-one | LC 1.69 [M+H]$^+$ = 322.3 and 324.2 |
| 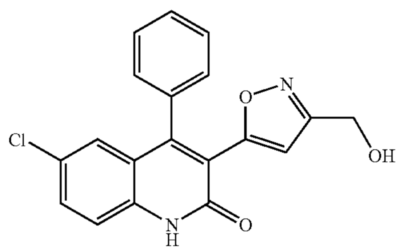 | 6-Chloro-3-(3-hydroxymethyl-isoxazol-5-yl)-4-phenyl-1H-quinolin-2-one | LC 2.33 [M+H]$^+$ = 322.3 and 324.2 |
| 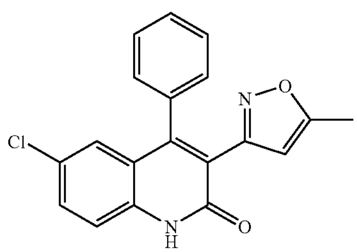 | 6-Chloro-3-(5-methyl-isoxazol-3-yl)-4-phenyl-1H-quinolin-2-one | LC 2.75 [M+H]$^+$ = 337.0 and 339.1 |
| 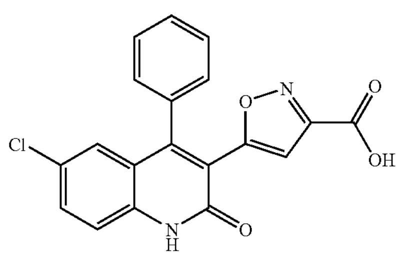 | 5-(6-Chloro-2-oxo-4-phenyl-1,2-dihydro-quinolin-3-yl)-isoxazol-3-carboxylic acid | LC 2.50 [M+H]$^+$ = 367.0 and 369.0 |
| 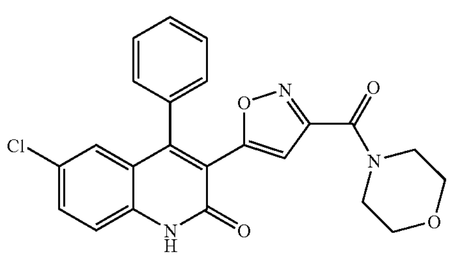 | 6-Chloro-3-[(3-morpholine-4-carbonyl)isoxazol-5-yl]-4-phenyl-1H-quinolin-2-one | LC 2.65 [M+H]$^+$ = 435.9 and 437.9 |
| 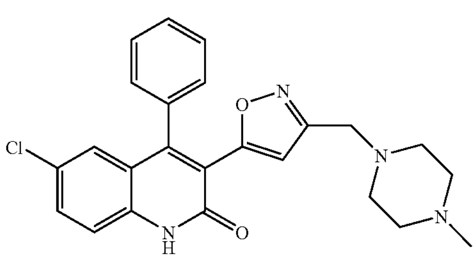 | 6-Chloro-3-[(3-(4-methyl-piperazin-1-ylmethyl)-isoxazol-5-yl]-4-phenyl-1H-quinolin-2-one | LC 1.94 [M+H]$^+$ = 435.1 and 437.0 |

TABLE 1-continued lists LC and mass spectral data of selected compounds of the present invention:

| Structure | Name | LC/MS |
|---|---|---|
| | 6-Chloro-4-phenyl-3-{3-[(2-piperidin-1-yl-ethylamino)-methyl]-isoxazol-5-yl}-1H-quinolin-2-one | LC 1.78 [M+H]⁺ = 463.1 and 465.1 |
| | {[5-(Chloro-2-oxo-4-phenyl-1,2-dihydro-quinolin-3-yl)-isoxazol-3-ylmethyl]-amino}-pentanedioic acid dimethyl ester | LC 2.57 [M+H]⁺ = 481.9 and 483.9 |
| | 6-Chloro-4-phenyl-3-{3-[(2-pyrrolodin-1-yl-ethylamino)-methyl]-isoxazol-5-yl}-1H-quinolin-2-one | LC 1.76 [M+H]⁺ = 449.1 and 451.1 |
| | 6-Chloro-3-{3-[(2-morpholin-4-yl-ethylamino)-methyl]-isoxazol-5-yl}-4-phenyl-1H-quinolin-2-one | LC 1.77 [M+H]⁺ = 465.2 and 466.2 |
| | 6-Chloro-4-phenyl-3-[(3-(4-pyridin-2-yl-piperazin-1-ylmethyl)-isoxazol-5-yl]-1H-quinolin-2-one | LC 1.88 [M+H]⁺ = 498.1 and 500.1 |

TABLE 1-continued lists LC and mass spectral data of selected compounds of the present invention:

| Structure | Name | Data |
|---|---|---|
| | 4-({[5-(6-Chloro-2-oxo-4-phenyl-1,2-dihydro-quinolin-3-yl)-isoxazol-3-ylmethyl]-amino}-methyl)-benzene sulfonamide | LC 2.16 [M+H]$^+$ = 520.9 and 522.0 |
| | 5-(6-Chloro-2-oxo-4-phenyl-1,2-dihydro-quinolin-3-yl)-isoxazol-3-carbonytrile | LC 3.10 [M+H]$^+$ = 348.1 and 350.2 |
| | 6-Chloro-4-phenyl-3-pyridin-2-yl-1H-quinolin-2-one | LC 1.81 [M+H]$^+$ = 333.2 and 335.2 |
| | 4-(4-Ethyl-phenyl)-3-(2-methyl-thiazol-4-yl)-2-oxo-1,2-dihydro-quinolin-6-carbonitrile | LC 2.48 [M+H]$^+$ = 372.2 |
| | 4-(4-Ethyl-phenyl)-3-(3-methyl-isoxasol-5-yl)-2-oxo-1,2-dihydro-quinoline-6-carbonitrile | LC 2.78 [M+H]$^+$ Expected for $C_{22}H_{17}N_3O_2$: 356.1 Observed: 356.1 |

TABLE 1-continued lists LC and mass spectral data of selected compounds of the present invention:

| | | |
|---|---|---|
| 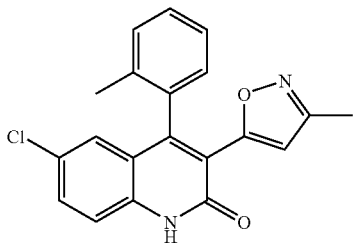 | 6-Chloro-3-(3-methyl-isoxazol-5-yl)-4-o-tolyl-1H-quinolin-2-one | LC 2.92<br>[M+H]$^+$ expected for C$_{20}$H$_{15}$ClN$_2$O$_2$: 351.1<br>Observed: 351.1 |
| 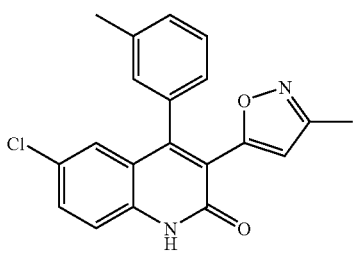 | 6-Chloro-3-(3-methyl-isoxazol-5-yl)-4-m-tolyl-1H-quinolin-2-one | LC 2.94<br>[M+H]$^+$ expected for C$_{20}$H$_{15}$ClN$_2$O$_2$: 351.1<br>Observed: 351.1 |
| 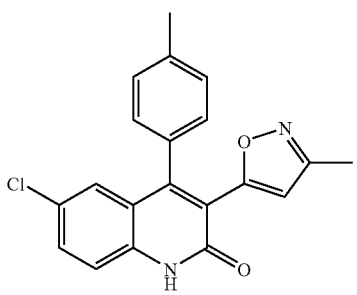 | 6-Chloro-3-(3-methyl-isoxazol-5-yl)-4-p-tolyl-1H-quinolin-2-one | LC 2.98<br>[M+H]$^+$ expected for C$_{20}$H$_{15}$ClN$_2$O$_2$: 351.1<br>Observed: 351.0 |
| 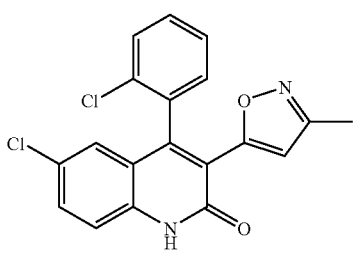 | 6-Chloro-4-(2-chloro-phenyl)-3-(3-methyl-isoxazol-5-yl)-1H-quinolin-2-one | LC 2.91<br>[M+H]$^+$ expected for C$_{19}$H$_{12}$Cl$_2$N$_2$O$_2$: 371.0<br>Observed: 371.0 |
| 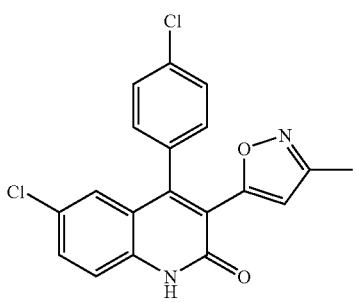 | 6-Chloro-4-(4-chloro-phenyl)-3-(3-methyl-isoxazol-5-yl)-1H-quinolin-2-one | LC 3.02<br>[M+H]$^+$ expected for C$_{19}$H$_{12}$Cl$_2$N$_2$O$_2$: 371.0<br>Observed: 371.0 |

TABLE 1-continued lists LC and mass spectral data of selected compounds of the present invention:

| Structure | Name | Data |
|---|---|---|
| | 4-(4-Acetyl-3-hydroxy-phenyl)-6-chloro-3-(3-methyl-isoxazol-5-yl)-1H-quinolin-2-one | LC 2.74<br>[M+H]$^+$ expected for C$_{21}$H$_{15}$ClN$_2$O$_4$: 395.1<br>Observed: 395.0 |
| | 4-(3-Acetyl-4-hydroxy-phenyl)-6-chloro-3-(3-methyl-isoxazol-5-yl)-1H-quinolin-2-one | LC 2.70<br>[M+H]$^+$ expected for C$_{21}$H$_{15}$ClN$_2$O$_4$: 395.1<br>Observed: 395.0 |
| | 6-Chloro-4-(4-hydroxy-phenyl)-3-(3-methyl-isoxazol-5-yl)-1H-quinolin-2-one | LC 2.29<br>[M+H]$^+$ expected for C$_{19}$H$_{13}$ClN$_2$O$_3$: 353.1<br>Observed: 353.0 |
| | 4-(5-Acetyl-2-methoxy-phenyl)-6-chloro-3-(3-methyl-isoxazol-5-yl)-1H-quinolin-2-one | LC 2.46<br>[M+H]$^+$ expected for C$_{22}$H$_{17}$ClN$_2$O$_4$: 409.1<br>Observed: 409.0 |
| | 4-(5-Acetyl-2-hydroxy-phenyl)-6-chloro-3-(3-methyl-isoxazol-5-yl)-1H-quinolin-2-one | LC 2.14<br>[M+H]$^+$ expected for C$_{21}$H$_{15}$ClN$_2$O$_4$: 395.1<br>Observed: 395.0 |

TABLE 1-continued lists LC and mass spectral data of selected compounds of the present invention:

| | | |
|---|---|---|
| 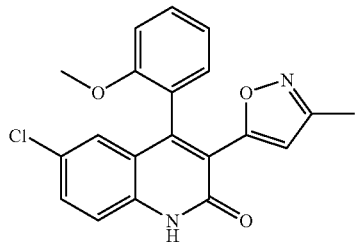 | 6-Chloro-4-(2-methoxy-phenyl)-3-(3-methyl-isoxazol-5-yl)-1H-quinolin-2-one | LC 2.71<br>[M+H]$^+$ expected for C$_{20}$H$_{15}$ClN$_2$O$_3$: 367.1<br>Observed: 367.0 |
| 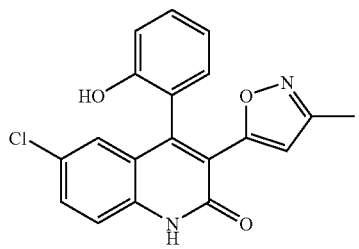 | 6-Chloro-4-(2-hydroxy-phenyl)-3-(3-methyl-isoxazol-5-yl)-1H-quinolin-2-one | LC 2.37<br>[M+H]$^+$ expected for C$_{19}$H$_{13}$ClN$_2$O$_3$: 353.1<br>Observed: 353.0 |
| 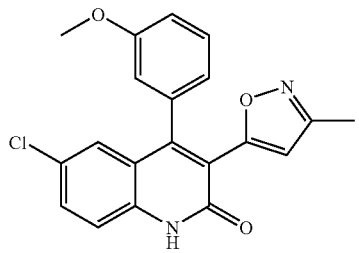 | 6-Chloro-4-(3-methoxy-phenyl)-3-(3-methyl-isoxazol-5-yl)-1H-quinolin-2-one | LC 2.79<br>[M+H]$^+$ expected for C$_{20}$H$_{15}$ClN$_2$O$_3$: 367.1<br>Observed: 367.0 |
| 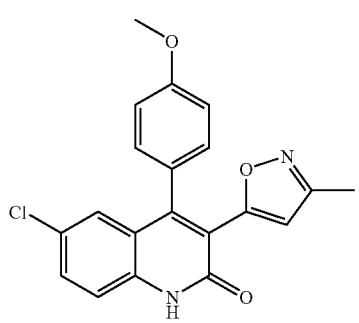 | 6-Chloro-4-(4-methoxy-phenyl)-3-(3-methyl-isoxazol-5-yl)-1H-quinolin-2-one | LC 2.78<br>[M+H]$^+$ expected for C$_{20}$H$_{15}$ClN$_2$O$_3$: 367.1<br>Observed: 367.0 |
| 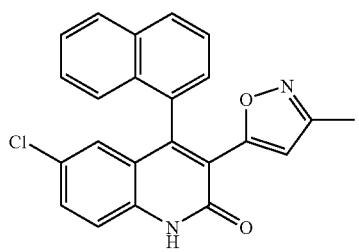 | 6-Chloro-3-(3-methyl-isoxazol-5-yl)-4-naphthalen-1-yl-1H-quinolin-2-one | LC 3.05<br>[M+H]$^+$ expected for C$_{23}$H$_{15}$ClN$_2$O$_2$: 387.1<br>Observed: 387.1 |

TABLE 1-continued lists LC and mass spectral data of selected compounds of the present invention:

| | | |
|---|---|---|
| 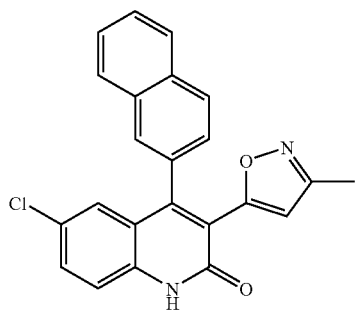 | 6-Chloro-3-(3-methyl-isoxazol-5-yl)-4-naphthalen-2-yl-1H-quinolin-2-one | LC 3.17<br>[M+H]$^+$ expected for<br>$C_{23}H_{15}ClN_2O_2$: 387.1<br>Observed: 387.1 |
| 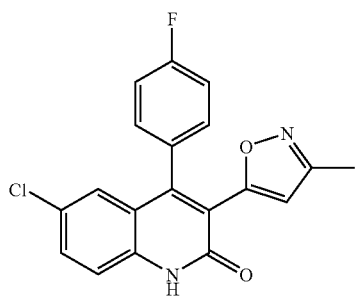 | 6-Chloro-4-(4-fluoro-phenyl)-3-(3-methyl-isoxazol-5-yl)-1H-quinolin-2-one | LC 2.78<br>[M+H]$^+$ expected for<br>$C_{19}H_{12}ClFN_2O_2$: 355.1<br>Observed: 355.0 |
| 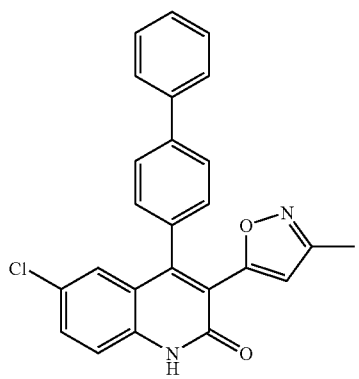 | 4-Biphenyl-4-yl-6-chloro-3-(3-methyl-isoxazol-5-yl)-1H-quinolin-2-one | LC 3.34<br>[M+H]$^+$ expected for<br>$C_{25}H_{17}ClN_2O_2$: 413.1<br>Observed: 413.0 |
| 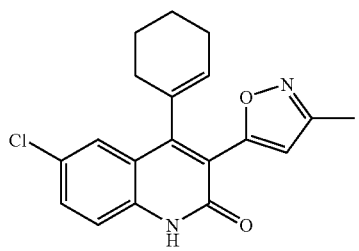 | 6-Chloro-4-cyclohex-1-enyl-3-(3-methyl-isoxazol-5-yl)-1H-quinolin-2-one | LC 3.03<br>[M+H]$^+$ expected for<br>$C_{19}H_{17}ClN_2O_2$: 341.1<br>Observed: 341.1 |
| 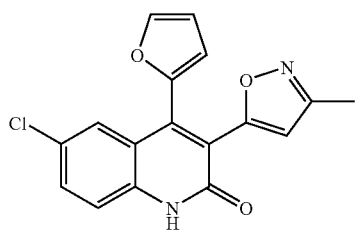 | 6-Chloro-4-furan-2-yl-3-(3-methyl-isoxazol-5-yl)-1H-quinolin-2-one | LC 2.52<br>[M+H]$^+$ expected for<br>$C_{17}H_{11}ClN_2O_3$: 327.1<br>Observed: 327.0 |

TABLE 1-continued lists LC and mass spectral data of selected compounds of the present invention:

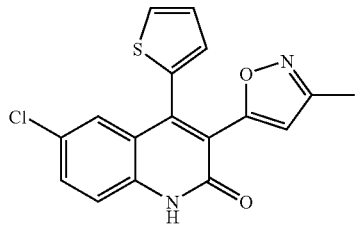

6-Chloro-3-(3-methyl-isoxazol-5-yl)-4-thiophen-2-yl-1H-quinolin-2-one

LC 2.72
[M+H]+ expected for
$C_{17}H_{11}ClN_2O_2S$: 343.0
Observed: 343.0

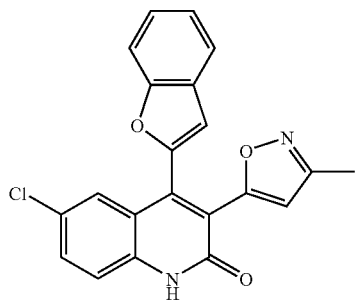

4-Benzofuran-2-yl-6-chloro-3-(3-methyl-isoxazol-5-yl)-1H-quinolin-2-one

LC 3.02
[M+H]+ expected for
$C_{21}H_{13}ClN_2O_3$: 377.1
Observed: 377.0

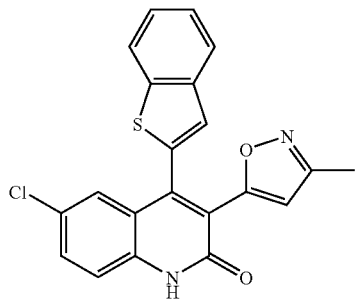

4-Benzo[b]thiophen-2-yl-6-chloro-3-(3-methyl-isoxazol-5-yl)-1H-quinolin-2-one

LC 3.15
[M+H]+ expected for
$C_{21}H_{13}ClN_2O_2S$: 393.0
Observed: 393.0

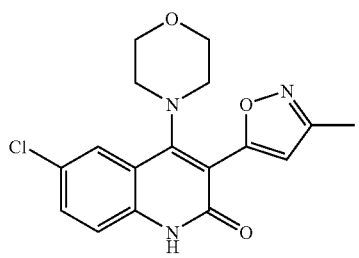

6-Chloro-3-(3-methyl-isoxazol-5-yl)-4-morpholin-4-yl-1H-quinolin-2-one

LC 2.18
[M+H]+ expected for
$C_{17}H_{16}ClN_3O_3$: 346.1
Observed: 346.1

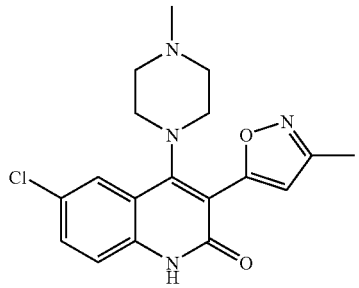

6-Chloro-3-(3-methyl-isoxazol-5-yl)-4-(4-methyl-piperazin-1-yl)-1H-quinolin-2-one LC 1.36
[M+H]+ expected for
$C_{18}H_{19}ClN_4O_2$: 359.1
Observed: 359.1

TABLE 1-continued lists LC and mass spectral data of selected compounds of the present invention:

| | | |
|---|---|---|
| 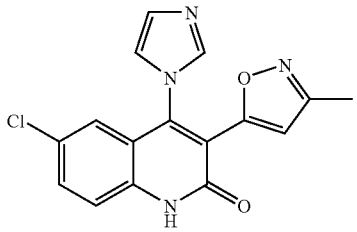 | 6-Chloro-4-imidazol-1-yl-3-(3-methyl-isoxazol-5-yl)-1H-quinolin-2-one | LC 1.33<br>[M+H]$^+$ expected for<br>$C_{16}H_{11}ClN_4O_2$: 327.1<br>Observed: 327.0 |
| 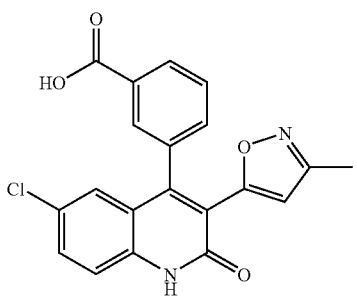 | 3-[6-Chloro-3-(3-methyl-isoxazol-5-yl)-2-oxo-1,2-dihydro-quinolin-4-yl]-benzoic acid | LC 2.25<br>[M+H]$^+$ expected for<br>$C_{20}H_{13}ClN_2O_4$: 381.1<br>Observed: 381.0 |
| 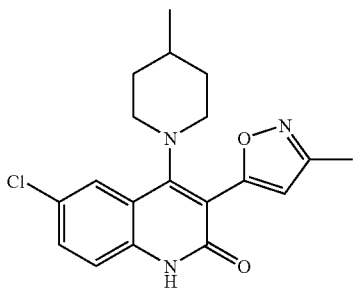 | 6-Chloro-3-(3-methyl-isoxazol-5-yl)-4-(4-methyl-piperidin-1-yl)-1H-quinolin-2-one | LC 3.16<br>[M+H]$^+$ expected for<br>$C_{19}H_{20}ClN_3O_2$: 358.1<br>Observed: 358.1 |
| 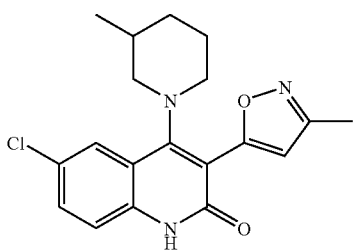 | 6-Chloro-3-(3-methyl-isoxazol-5-yl)-4-(3-methyl-piperidin-1-yl)-1H-quinolin-2-one | LC 3.15<br>[M+H]$^+$ expected for<br>$C_{19}H_{20}ClN_3O_2$: 358.1<br>Observed: 358.1 |
| 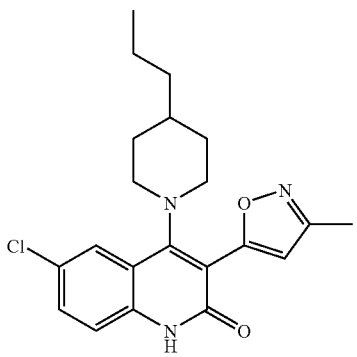 | 6-Chloro-3-(3-methyl-isoxazol-5-yl)-4-(4-propyl-piperidin-1-yl)-1H-quinolin-2-one | LC 3.66<br>[M+H]$^+$ expected for<br>$C_{21}H_{24}ClN_3O_2$: 386.1<br>Observed: 386.1 |

TABLE 1-continued lists LC and mass spectral data of selected compounds of the present invention:

| Structure | Name | Data |
|---|---|---|
| 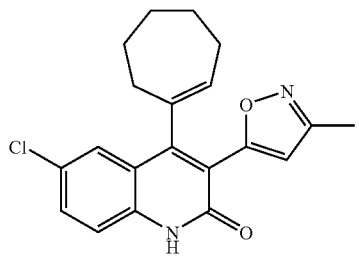 | 6-Chloro-4-cyclohept-1-enyl-3-(3-methyl-isoxazol-5-yl)-1H-quinolin-2-one | LC 3.26<br>[M+H]$^+$ expected for C$_{20}$H$_{19}$ClN$_2$O$_2$: 355.1<br>Observed: 355.1 |
| 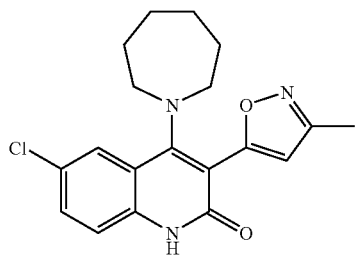 | 4-Azepan-1-yl-6-chloro-3-(3-methyl-isoxazol-5-yl)-1H-quinolin-2-one | LC 3.23<br>[M+H]$^+$ expected for C$_{19}$H$_{20}$ClN$_3$O$_2$: 358.1<br>Observed: 358.1 |
| 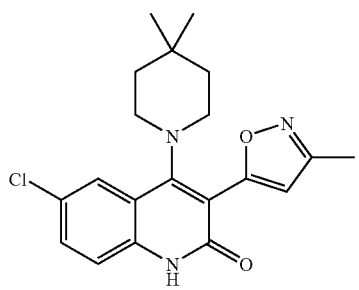 | 6-Chloro-4-(4,4-dimethyl-piperidin-1-yl)-3-(3-methyl-isoxazol-5-yl)-1H-quinolin-2-one | LC 3.27<br>[M+H]$^+$ expected for C$_{20}$H$_{22}$ClN$_3$O$_2$: 372.1<br>Observed: 372.1 |
| 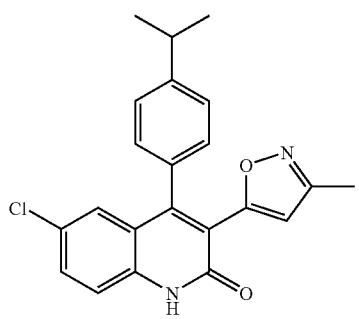 | 6-Chloro-4-(4-isopropyl-phenyl)-3-(3-methyl-isoxazol-5-yl)-1H-quinolin-2-one | LC 3.32<br>[M+H]$^+$ expected for C$_{22}$H$_{19}$ClN$_2$O$_2$: 379.1<br>Observed: 379.1 |
| 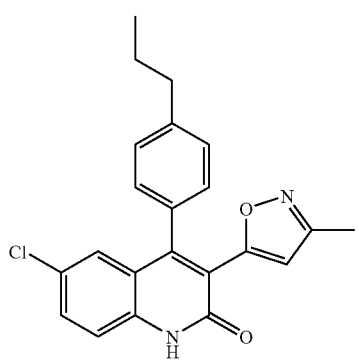 | 6-Chloro-3-(3-methyl-isoxazol-5-yl)-4-(4-propyl-phenyl)-1H-quinolin-2-one | LC 3.38<br>[M+H]$^+$ expected for C$_{22}$H$_{19}$ClN$_2$O$_2$: 379.1<br>Observed: 379.1 |

TABLE 1-continued lists LC and mass spectral data of selected compounds of the present invention:

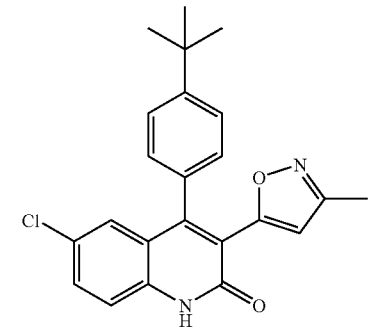

4-(4-tert-Butyl-phenyl)-6-chloro-3-(3-methyl-isoxazol-5-yl)-1H-quinolin-2-one

LC 3.45
[M+H]$^+$ expected for C$_{23}$H$_{21}$ClN$_2$O$_2$: 393.1
Observed: 393.1

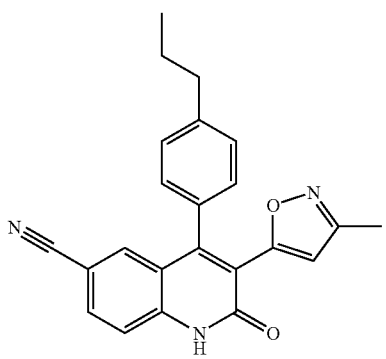

3-(3-Methyl-isoxazol-5-yl)-2-oxo-4-(4-propyl-phenyl)-1,2-dihydro-quinolin-6-carbonitrile LC 2.97
[M+H]$^+$ expected for C$_{23}$H$_{19}$N$_3$O$_2$: 370.2
Observed: 370.1

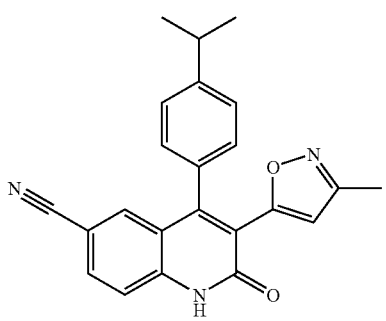

4-(4-Isopropyl-phenyl)-3-(3-methyl-isoxazol-5-yl)-2-oxo-1,2-dihydro-quinolin-6-carbonitrile LC 2.92
[M+H]$^+$ expected for C$_{23}$H$_{19}$N$_3$O$_2$: 370.2
Observed: 370.1

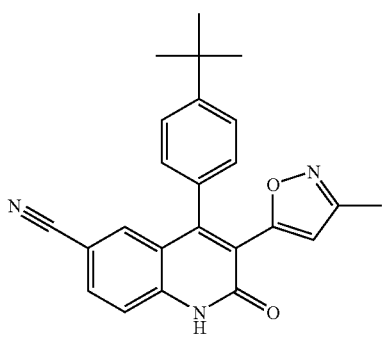

4-(4-tert-Butyl-phenyl)-3-(3-methyl-isoxazol-5-yl)-2-oxo-1,2-dihydro-quinolin-6-carbonitrile LC 3.05
[M+H]$^+$ expected for C$_{24}$H$_{21}$N$_3$O$_2$: 384.2
Observed: 384.1

TABLE 1-continued lists LC and mass spectral data of selected compounds of the present invention:

| | | |
|---|---|---|
| 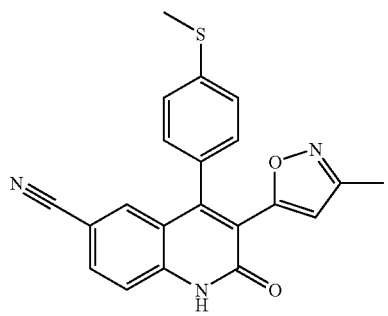 | 3-(3-Methyl-isoxazol-5-yl)-4-(4-methylsulfanyl-phenyl)-2-oxo-1,2-dihydro-quinolin-6-carbonitrile | LC 2.66<br>[M+H]$^+$ expected for $C_{21}H_{15}N_3O_2S$: 374.1<br>Observed: 374.0 |
| 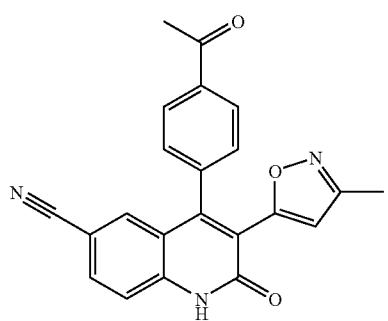 | 4-(4-Acetyl-phenyl)-3-(3-methyl-isoxazol-5-yl)-2-oxo-1,2-dihydro-quinolin-6-carbonitrile | LC 2.24<br>[M+H]$^+$ expected for $C_{22}H_{15}N_3O_3$: 370.1<br>Observed: 370.0 |
| 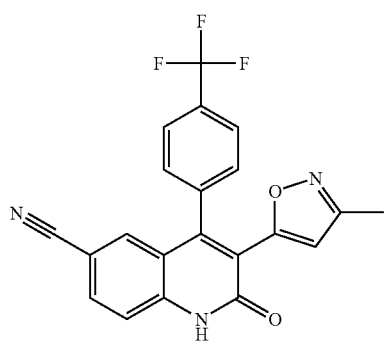 | 3-(3-Methyl-isoxazol-5-yl)-2-oxo-4-(4-trifluoromethyl-phenyl)-1,2-dihydro-quinolin-6-carbonitrile | LC 2.68<br>[M+H]$^+$ expected for $C_{21}H_{12}F_3N_3O_2$: 396.1<br>Observed: 396.0 |
| 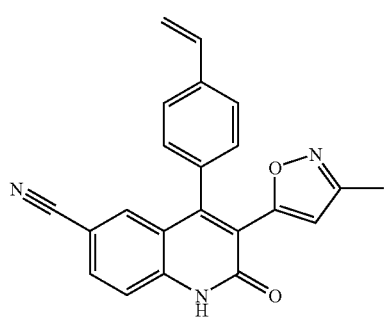 | 3-(3-Methyl-isoxazol-5-yl)-2-oxo-4-(4-vinyl-phenyl)-1,2-dihydro-quinolin-6-carbonitrile | LC 2.67<br>[M+H]$^+$ expected for $C_{22}H_{15}N_3O_2$: 354.1<br>Observed: 354.1 |

TABLE 1-continued lists LC and mass spectral data of selected compounds of the present invention:

| Structure | Name | Data |
|---|---|---|
| 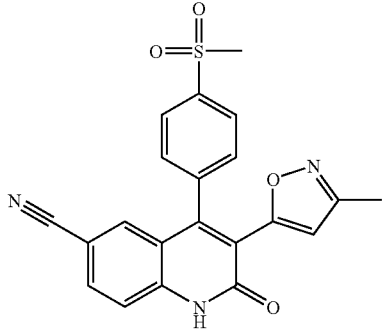 | 4-(4-Methanesulfonyl-phenyl)-3-(3-methyl-isoxazol-5-yl)-2-oxo-1,2-dihydro-quinolin-6-carbonitrile | LC 2.05<br>$[M+H]^+$ expected for $C_{21}H_{15}N_3O_4S$: 406.1<br>Observed: 406.1 |
| 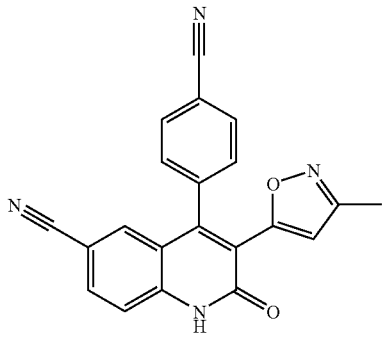 | 4-(4-Cyano-phenyl)-3-(3-methyl-isoxazol-5-yl)-2-oxo-1,2-dihydro-quinolin-6-carbonitrile | LC 2.36<br>$[M+H]^+$ expected for $C_{21}H_{12}N_4O_2$: 353.1<br>Observed: 353.1 |
| 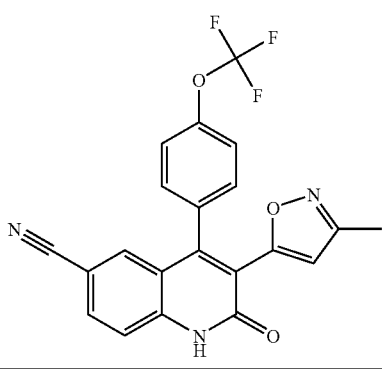 | 3-(3-Methyl-isoxazol-5-yl)-2-oxo-4-(4-trifluoromethoxy-phenyl)-1,2-dihydro-quinolin-6-carbonitrile | LC 2.78<br>$[M+H]^+$ expected for $C_{21}H_{12}F_3N_3O_3$: 412.1<br>Observed: 411.9 |

IV. Results

An autophosphorylation, fluorescence polarization competition immunoassay was used to determine the potency for c-fms inhibition exhibited by selected compounds of Formulae I and II. The assay was performed in black 96-well microplates (LJL BioSystems). The assay buffer used was 100 mM HEPES, pH 7.5, 1 mM DTT, 0.01% (v/v) Tween-20. Compounds were diluted in assay buffer containing 4% DMSO just prior to the assay. To each well, 5 μL of compound were added followed by the addition of 3 μL of a mix containing 33 nM c-fms (3DP) and 16.7 mM $MgCl_2$ (Sigma) in assay buffer. The kinase reaction was initiated by adding 2 μL of 5 mM ATP (Sigma) in assay buffer. The final concentrations in the assay were 10 nM c-fms, 1 mM ATP, 5 mM $MgCl_2$, 2% DMSO. Control reactions were ran in each plate: in positive and negative control wells, assay buffer (made 4% in DMSO) was substituted for the compound; in addition, positive control wells received 1.2 μL of 50 mM EDTA.

The plates were incubated at room temperature for 45 min. At the end of the incubation, the reaction was quenched with 1.2 μL of 50 mM EDTA (EDTA was not added to the positive control wells at this point; see above). Following a 5-min incubation, each well received 10 μL of a 1:1:3 mixture of anti-phosphotyrosine antibody, 10X, PTK green tracer, 10X (vortexed), FP dilution buffer, respectively (all from PanVera, cat. #P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction. The reported $IC_{50}$ values are averages of three independent measurements.

Table 2 lists representative compounds of Formulae I and II of the invention.

TABLE 2

| COMPOUND | IC$_{50}$ (uM) |
| --- | --- |
| 6-bromo-4-phenyl-3-(3-methylisoxazol-5-yl)quinolin-2(1H)-one | A |
| 6-chloro-4-phenyl-3-(3-methylisoxazol-5-yl)quinolin-2(1H)-one | A |
| 6-nitro-4-phenyl-3-(3-methylisoxazol-5-yl)quinolin-2(1H)-one | A |
| 4-(4-ethylphenyl)-3-(1H-imidazol-4-yl)-2-oxo-1,2-dihydroquinoline-6-carbonitrile | A |
| 4-(4-ethylphenyl)-3-(3-methylisoxazol-5-yl)-2-oxo-1,2-dihydroquinoline-6-carbonitrile | A |

TABLE 2-continued

| COMPOUND | IC$_{50}$ (uM) |
| --- | --- |
| 4-(4-isopropylphenyl)-3-(3-methylisoxazol-5-yl)-2-oxo-1,2-dihydroquinoline-6-carbonitrile | A |
| 4-(4-vinylphenyl)-3-(3-methylisoxazol-5-yl)-2-oxo-1,2-dihydroquinoline-6-carbonitrile | A |
| 4-(cyclohept-1-enyl)-3-(3-methylisoxazol-5-yl)-2-oxo-1,2-dihydroquinoline-6-carbonitrile | A |
| 6-chloro-4-phenyl-3-(1H-imidazol-4-yl)quinolin-2(1H)-one | A |
| 6-chloro-4-phenyl-3-(3-tert-butylisoxazol-5-yl)quinolin-2(1H)-one | A |

TABLE 2-continued

| COMPOUND | IC$_{50}$ (uM) |
|---|---|
| [6-chloro-4-phenyl-3-(3-isopropylisoxazol-5-yl)quinolin-2(1H)-one] | A |
| [6-chloro-4-(3-hydroxyphenyl)-3-(3-methylisoxazol-5-yl)quinolin-2(1H)-one] | A |
| [6-chloro-4-(2-fluorophenyl)-3-(3-methylisoxazol-5-yl)quinolin-2(1H)-one] | A |
| [6-chloro-3-(3-aminoisoxazol-5-yl)-4-phenylquinolin-2(1H)-one] | A |
| [6-chloro-3-(3-carboxyisoxazol-5-yl)-4-phenylquinolin-2(1H)-one] | A |
| [6-chloro-4-phenyl-3-(pyrrol-2-yl)quinolin-2(1H)-one] | A |

TABLE 2-continued

| COMPOUND | IC$_{50}$ (uM) |
|---|---|
| [6-chloro-3-(3-methylisoxazol-5-yl)-4-(thiophen-2-yl)quinolin-2(1H)-one] | A |
| [6-chloro-3-(3-methylisoxazol-5-yl)-4-(piperidin-1-yl)quinolin-2(1H)-one] | A |
| [6-bromo-3-(1H-imidazol-4-yl)-4-phenylquinolin-2(1H)-one] | A |
| [6-chloro-3-(3-methylisoxazol-5-yl)-4-phenyl-1,8-naphthyridin-2(1H)-one] | B |
| [6-cyano-3-(1-methylimidazol-4-yl)-4-phenylquinolin-2(1H)-one] | B |
| [6-chloro-4-(benzothiophen-2-yl)-3-(3-methylisoxazol-5-yl)quinolin-2(1H)-one] | B |

TABLE 2-continued
| COMPOUND | IC$_{50}$ (uM) |
|---|---|
| 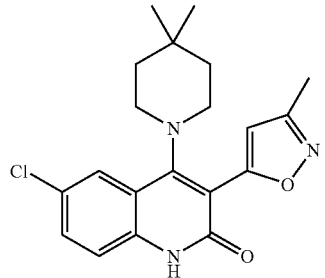 | B |
| 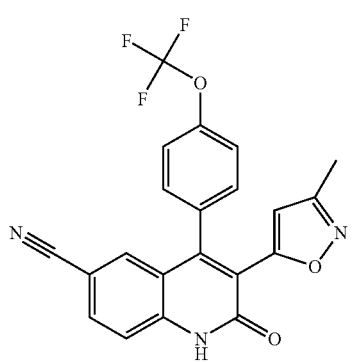 | B |
| 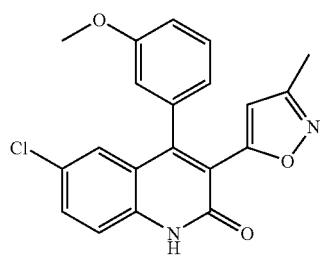 | B |
| 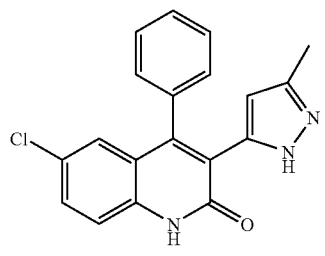 | B |
| 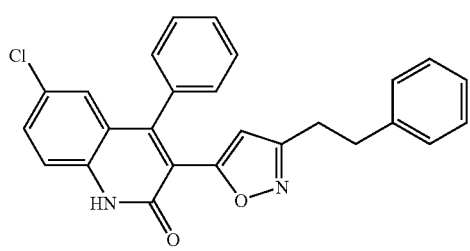 | C |
TABLE 2-continued
| COMPOUND | IC$_{50}$ (uM) |
|---|---|
| 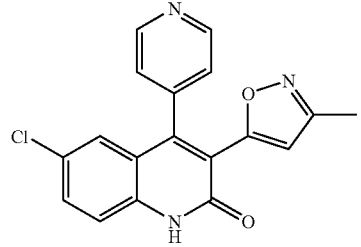 | C |
| 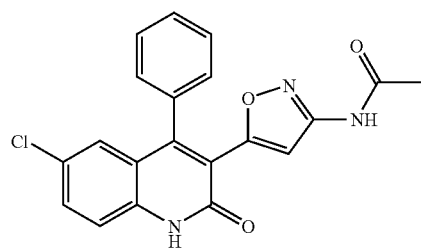 | C |
| 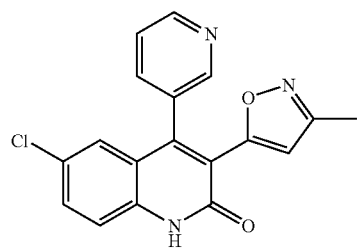 | C |
| 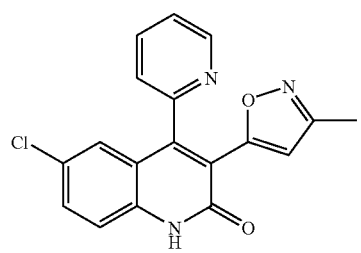 | C |
| 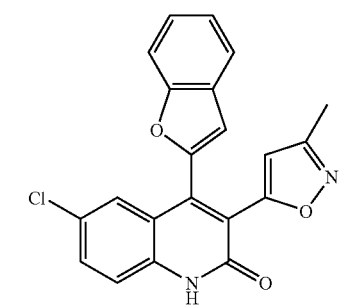 | C |

TABLE 2-continued

| COMPOUND | IC$_{50}$ (uM) |
|---|---|
| (6-chloro-4-(naphthalen-2-yl)-3-(3-methylisoxazol-5-yl)quinolin-2(1H)-one) | C |
| (3-(5-bromopyridin-3-yl)-6-chloro-4-phenylquinolin-2(1H)-one) | C |
| (6-chloro-4-phenyl-3-(pyridin-2-yl)quinolin-2(1H)-one) | C |
| (3-(1H-benzimidazol-2-yl)-6-chloro-4-phenylquinolin-2(1H)-one) | C |
| (6-chloro-4-phenyl-3-(pyridin-3-yl)quinolin-2(1H)-one) | C |
| (6-hydroxy-3-(3-methylisoxazol-5-yl)-4-phenylquinolin-2(1H)-one) | C |

TABLE 2-continued

| COMPOUND | IC$_{50}$ (uM) |
|---|---|
| (6-(1,2-dihydroxyethyl)-3-(3-methylisoxazol-5-yl)-4-phenylquinolin-2(1H)-one) | D |
| (7-chloro-3-(3-methylisoxazol-5-yl)-4-phenylquinolin-2(1H)-one) | D |
| (ethyl 3-(6-chloro-2-oxo-4-phenyl-1,2-dihydroquinolin-3-yl)benzoate) | D |
| (8-chloro-3-(3-methylisoxazol-5-yl)-4-phenylquinolin-2(1H)-one) | D |
| (6-chloro-4-phenyl-3-(2H-tetrazol-5-yl)quinolin-2(1H)-one) | D |
| (6-(hydroxymethyl)-3-(3-methylisoxazol-5-yl)-4-phenylquinolin-2(1H)-one) | D |

TABLE 2-continued

| COMPOUND | IC$_{50}$ (uM) |
|---|---|
| 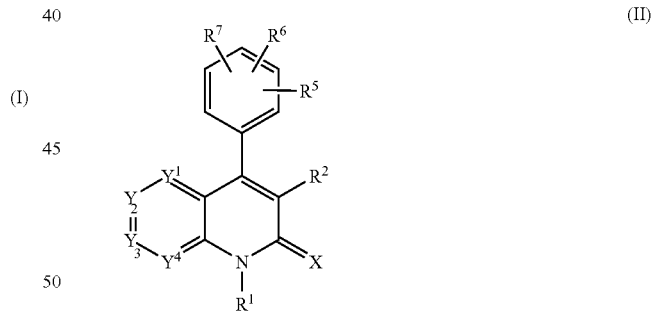 | C |
| | B |
| | D |

A: <0.5 μM
B: >0.5 μM and <1 μM
C: >1 μM and <10 μM
D: >10 μM

What is claimed is:

1. A compound of Formula (I):

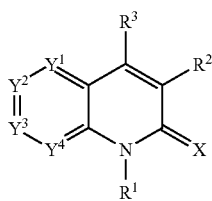

or a solvate, hydrate, tautomer or pharmaceutically acceptable salt thereof, wherein $R^1$ is —H;

$R^2$ is a 5- to 7-membered mono- or a 8- to 10-membered bicyclic heteroaromatic or heterocyclic ring having from one to four heteroatoms selected from N, O or S, and may be optionally substituted with one or more of —$C_{1-6}$ alkyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$, —$SO_2NR_aR_b$, —N=C($R_a$)—$NR_bR_c$, —$CH_2NR_aR_b$, —$CH_2NR_aR_bNR_cR_d$, —$NR_aSO_2R_b$, —$NR_aCONR_bR_c$, —$N(R_a)CON(R_b)$-alkyl-$R_c$, or —$CH_2N(CH_2CH_2)_2NR_a$;

$R^3$ is phenyl, naphthyl or cycloalkyl, each of which may be optionally substituted with one or more of —$C_{1-6}$ alkyl, —$C_{2-6}$ alkenyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SR_a$, —$SO_2R_a$, —$SO_3R_a$ or —$SO_2NR_aR_b$; or a 5- to 7-membered mono- or a 8- to 10-membered bicyclic heteroaromatic ring having from one to four heteroatoms selected from N, O or S, and may be optionally substituted with one or more of —$C_{1-6}$ alkyl, —$C_{2-6}$ alkenyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SR_a$, —$SO_2R_a$, —$SO_3R_a$ or —$SO_2NR_aR_b$;

X is O; and $Y^1$, $Y^2$, $Y^3$ and $Y^4$ are —C($R^4$)—, wherein each $R^4$ is independently —H, —$C_{1-6}$ alkyl, —$C_{2-6}$ alkenyl, amino, aminoalkyl, halogen, hydroxy, hydroxyalkyl, —$CF_3$, alkoxy, aryl, aralkyl, heteroaryl, heteroaralkyl, aryloxy, heteroaryloxy, arylalkoxy, $SR_a$, $NR_aR_b$, $PhCF_3$, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, —$N(R_a)SO_2R_b$, or wherein $R_a$, $R_b$, $R_c$ and $R_d$ are independently hydrogen, alkoxy, alkyl, alkenyl, cycloalkyl, aryl, aralkyl, heteroaralkyl or heteroaryl, any one of which except hydrogen may be substituted with one or more of the following: —$SO_2NH_2$, $SO_2$-alkyl, or —$CO_2$-alkyl.

2. A compound of Formula (II):

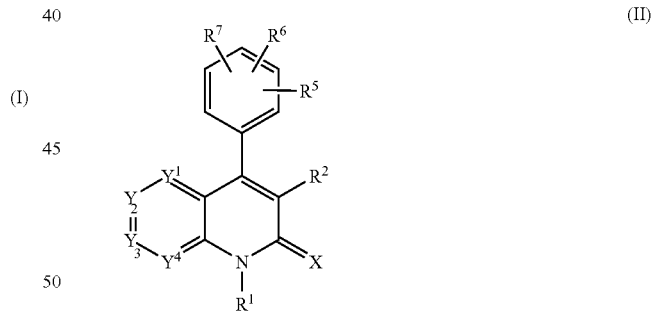

or a solvate, hydrate, tautomer or pharmaceutically acceptable salt thereof, wherein $R^1$ is —H, —$C_{1-6}$ alkyl, cycloalkyl, aryl, aralkyl, heteroaryl, heteroaralkyl, —$COR_a$, —$COOR_a$, —$CONR_aR_b$ or —$SO_2R_a$, $R^2$ is a 5- to 7-membered heterocyclic or heteroaromatic ring having from one to three heteroatoms selected from N, O or S, and may be optionally substituted with one or more of —$C_{1-6}$ alkyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, CON- $R_aR_b$, $N(R_a)COR_b$, —$NO_2$, —$SO_2R_a$, —$NR_aSO_2R_b$, —$SO_3R_a$ or —$SO_2NR_aR_b$;

$R^5$, $R^6$ and $R^7$ are independently
—$C_{1-6}$ alkyl, —$C_{2-6}$ alkenyl, amino, aminoalkyl, heteroaryl, halogen, meta-hydroxy, para-hydroxy, meta-methoxy, para-methoxy, —$C_{2-5}$ alkoxy, —$CF_3$, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SR_a$, —$SO_2R_a$, —$NR_aSO_2R_b$, —$SO_3R_a$ or —$SO_2NR_aR_b$;

X is
O, S, $N(R_a)N(R_a)(R_b)$, $N(R_a)N(R_b)COR_c$; and
$Y^1$, $Y^2$, $Y^3$ and $Y^4$ are —$C(R^4)$—,
wherein each $R^4$ is independently
—H, —$C_{1-6}$ alkyl, —$C_{2-6}$ alkenyl, amino, aminoalkyl, halogen, hydroxy, hydroxyalkyl, —$CF_3$, alkoxy, aryl, aralkyl, heteroaryl, heteroaralkyl, aryloxy, heteroaryloxy, arylalkoxy, $SR_a$, $NR_aR_b$, $PhCF_3$, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, —$N(R_a)SO_2R_b$, or wherein two independent $R^4$ substituents, taken together with $Y^1=Y^2$, $Y^2=Y^3$ or $Y^3=Y^4$, form a 5- to 7-membered cyclic, heterocyclic, aryl or heteroaryl ring containing from 0-3 heteroatoms selected from N, O or S, which may be optionally substituted with —H, —$C_{1-6}$ alkyl, amino, aminoalkyl, halogen, hydroxy, hydroxyalkyl, —$CF_3$, alkoxy, aryl, aralkyl, heteroaryl, heteroaralkyl, aryloxy, heteroaryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$N(R_a)SO_2R_b$, —$SO_3R_a$ or —$SO_2NR_aR_b$,
wherein $R_a$, $R_b$, $R_c$ and $R_d$ are independently hydrogen, alkoxy, alkyl, alkenyl, cycloalkyl, aryl, aralkyl, heteroaralkyl or heteroaryl, any one of which except hydrogen may be substituted with one or more of the following: —$SO_2NH_2$, $SO_2$-alkyl, or —$CO_2$-alkyl,
with the proviso that $R^2$ is neither isoxazoline, pyrazoline, nor a benzimidazole ring and with the proviso that if $Y^2$ is —$C(R^4)$, then $R^4$ is not a —$C_1$-heteroaromatic.

3. A compound of claim 1, wherein
$R^1$ is —H;
$R^2$ is
a 5- to 7-membered heterocyclic or heteroaromatic ring having from one to three heteroatoms selected from N, O or S, and may be optionally substituted with one or more of —$C_{1-6}$ alkyl, amino, aminoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$;
X is O; and
$Y^1$, $Y^2$, $Y^3$ and $Y^4$ are —$C(R^4)$—,
wherein each $R^4$ is independently
—H, —$C_{1-6}$ alkyl, —$C_{2-6}$ alkenyl, amino, aminoalkyl, halogen, hydroxy, hydroxyalkyl, —$CF_3$, alkoxy, aryl, aralkyl, heteroaryl, heteroaralkyl, aryloxy, heteroaryloxy, arylalkoxy, $SR_a$, $NR_aR_b$, $PhCF_3$, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, —$N(R_a)SO_2R_b$, or
wherein $R_a$, $R_b$, $R_c$ and $R_d$ are independently hydrogen, alkoxy, alkyl, alkenyl, cycloalkyl, aryl, aralkyl, heteroaralkyl or heteroaryl, any one of which except hydrogen may be substituted with one or more of the following: —$SO_2NH_2$, $SO_2$-alkyl, or —$CO_2$-alkyl.

4. A compound of claim 1, which is one of
6-chloro-3-(3-methyl-isoxazol-5-yl)-4-(pyridin-4-yl)-1H-quinolin-2-one;
6-chloro-3-(3-methyl-isoxazol-5-yl)-4-(pyridin-3-yl)-1H-quinolin-2-one;
6-chloro-3-(3-methyl-isoxazol-5-yl)-4-(pyridin-2-yl)-1H-quinolin-2-one;
6-Chloro-3,4-diphenyl-1H-quinolin-2-one;
6-Chloro-3-[3-(4-methyl-piperazin-1-ylmethyl)-isoxazol-5-yl]-4-phenyl-1H-quinolin-2-one;
6-Chloro-4-phenyl 3-{3-[(2-piperidin-1-yl-ethylamino)-methyl]-isoxazol-5-yl}-1H-quinolin-2-one;
6-Chloro-4-phenyl-3-{3-[(2-pyrrolidin-1-yl-ethylamino)-methyl]-isoxazol-5-yl}-1H-quinolin-2-one;
6-Chloro-3-{3-[(2-morpholin-4-yl-ethylamino)-methyl]-isoxazol-5-yl}-4-phenyl-1H-quinolin-2-one;
6-Chloro-4-phenyl-3-[3-(4-pyridin-2-yl-piperazin-1-ylmethyl)-isoxazol-5-yl]-1H-quinolin-2-one;
6-Chloro-4-cyclohex-1-enyl-3-(3-methyl-isoxazol-5-yl)-1H-quinolin-2-one;
6-Chloro-4-furan-2-yl-3-(3-methyl-isoxazol-5-yl)-1H-quinolin-2-one;
6-Chloro-3-(3-methyl-isoxazol-5-yl)-4-thiophen-2-yl-1H-quinolin-2-one;
4-Benzofuran-2-yl-6-chloro-3-(3-methyl-isoxazol-5-yl)-1H-quinolin-2-one6-Chloro-3-(3-methyl-isoxazol-5-yl)-4-morpholin-4-yl-1H-quinolin-2-one;
6-Chloro-3-(3-methyl-isoxazol-5-yl)-4-(4-methyl-piperazin-1-yl)-1H-quinolin-2-one;
6-Chloro-3-(3-methyl-isoxazol-5-yl)-4-(4-methyl-piperidin-1-yl)-1H-quinolin-2-one;
6-Chloro-4-imidazol-1-yl-3-(3-methyl-isoxazol-5-yl)-1H-quinolin-2-one;
4-Benzo[b]thiophen-2-yl-6-chloro-3-(3-methyl-isoxazol-5-yl)-1H-quinolin-2-one;
6-Chloro-4-cyclohept-1-enyl-3-(3-methyl-isoxazol-5-yl)-1H-quinolin-2-one;
6-Chloro-3-(3-methyl-isoxazol-5-yl)-4-(4-propyl-piperidin-1-yl)-1H-quinolin-2-one;
6-Chloro-3-(3-methyl-isoxazol-5-yl)-4-(3-methyl-piperidin-1-yl)-1H-quinolin-2-one;
6-Chloro-4-cycloheptyl-3-(3-methyl-isoxazol-5-yl)-1H-quinolin-2-one;
6-Chloro-4-(4,4-dimethyl-piperidin-1-yl)-3-(3-methyl-isoxazol-5-yl)-1H-quinolin-2-one;
4-(4-tert-Butyl-phenyl)-6-chloro-3-(3-methyl-isoxazol-5-yl)-1H-quinolin-2-one;
N'-[5-(6-Chloro-2-oxo-4-phenyl-1,2-dihydro-quinolin-3-yl)-isoxazol-3-yl]-N,N-dimethyl-formamidine;
N'-[5-(6-Chloro-2-oxo-4-phenyl-1,2-dihydro-quinolin-3-yl)-isoxazol-3-yl]-N,N-dimethyl-acetamidine;
N'-[5-(6-Chloro-2-oxo-4-phenyl-1,2-dihydro-quinolin-3-yl)-isoxazol-3-yl]-N,N-dimethyl-propionamidine;
N-[5-(6-Chloro-2-oxo-4-phenyl-1,2-dihydro-quinolin-3-yl)-isoxazol-3-yl]-methanesulfonamide;
6-Chloro-3-(3-methyl-isoxazol-5-yl)-4-piperidin-1-yl-1H-quinolin-2-one;
6-Chloro-4-cyclohexyl-3-(3-methyl-isoxazol-5-yl)-1H-quinolin-2-one;
4-Cyclohept-1-enyl-3-(3-methyl-isoxazol-5-yl)-2-oxo-1,2-dihydro-quinoline-6-carbonitrile;
6-Chloro-3-(3-methyl-isoxazol-5-yl)-4-naphthalen-1-yl-1H-quinolin-2-one; and
6-Chloro-3-(3-methyl-isoxazol-5-yl)-4-naphthalen-2-yl-1H-quinolin-2-one.

5. A compound of claim 2, which is one of
3-[6-Chloro-3-(3-methyl-isoxazol-5-yl)-2-oxo-1,2-dihydro-quinolin-4-yl]-benzoic acid;
6-Chloro-3-(3-methyl-benzo[b]thiophen-2-yl)-4-phenyl-1H-quinolin-2-one;
6-Chloro-4-phenyl-3-thiophen-2-yl-1H-quinolin-2-one;
6-Chloro-4-phenyl-3-(1H-pyrrol)-2-yl-1H-quinolin-2-one;
6-Chloro-4-phenyl-3-pyrazol-1-yl-1H-quinolin-2-one;
6-Chloro-3-(5-methyl-2H-pyrazol-3-yl)-4-phenyl-1H-quinolin-2-one;
3-(1-Benzyl-1H-imidazol-2-yl)-6-Chloro-4-phenyl-1H-quinolin-2-one;
6-Chloro-3-(5-methyl-isoxazol-3-yl)-4-phenyl-1H-quinolin-2-one;
6-Chloro-4-phenyl-3-pyridin-2-yl-1H-quinolin-2-one;
3-(2-Methyl-thiazol-4-yl)-2-oxo-4-phenyl-1,2-dihydro-quinoline-6-carbonitrile;
6-Chloro-3-(3-hydroxymethyl-isoxazol-5-yl)-4-phenyl-1H-quinolin-2-one;
5-(6-Chloro-2-oxo-4-phenyl-1,2-dihydro-quinolin-3-yl)-isoxazole-3-carboxylic acid;
6-Chloro-3-[(5-morpholine-4-carbonyl)1H-pyrrol-2-yl]-4-phenyl-1H-quinolin-2-one;
6-Chloro-3-[(3-morpholine-4-carbonyl)isoxazol-5-yl]-4-phenyl-1H-quinolin-2-one;
2-{[5-(6-Chloro-2-oxo-4-phenyl-1,2-dihydro-quinolin-3-yl)-isoxazol-3-ylmethyl]-amino}-malonic acid dimethyl ester;
4-({[5-(6-Chloro-2-oxo-4-phenyl-1,2-dihydro-quinolin-3-yl)-isoxazol-3-ylmethyl]-amino}-methyl)-benzene sulfonamide;
5-(6-Chloro-2-oxo-4-phenyl-1,2-dihydro-quinolin-3-yl)-isoxazole-3-carbonitrile;
6-Chloro-3-(1H-imidazol-2-yl)4-phenyl-1H-quinolin-2-one;
3-(5-bromo-pyridin-3-yl)-6-chloro-4-phenyl-1H-quinolin-2-one;
6-Chloro-4-(2-fluorophenyl)-3-(3-methyl-isoxazol-5-yl)-1H-quinolin-2-one;
6-Chloro-4-phenyl-3-(3-methyl-isoxazol-5-yl)-1H-quinolin-2-one;
6-Chloro-3-(3-methyl-isoxazol-5-yl)-4-pyridin-3-yl-1H-quinolin-2-one;
6-Bromo-3-(3-methyl-isoxazol-5-yl)-4-phenyl-1H-quinolin-2-one;
6-Chloro-4-(3-hydroxyphenyl)-3-(3-methyl-isoxazol-5-yl)-1H-quinolin-2-one;
6-Chloro-3-(3-methyl-isoxazol-5-yl)-4-pyridin-4-yl-1H-quinolin-2-one;
6-(1,2-dihydroxy-ethyl)-3-(3-methyl-isoxazol-5-yl)-4-phenyl-1H-quinolin-2-one;
3-(3-Methylisoxazol-5-yl)-2-oxo-4-phenyl-1,2-dihydro-quinoline-6-carboxylic acid;
6-Hydroxymethyl-3-(3-methylisoxazol-5-yl)-4-phenyl-1H-quinolin-2-one;
3-(3-tert-Butyl-isoxazol-5-yl)-6-chloro-4-phenyl-1H-quinolin-2-one;
6-Chloro-3-(3-isopropyl-isoxazol-5-yl)-4-phenyl-1H-quinolin-2-one;
6-Chloro-3-(4-isobutyl-oxazol-2-yl)-4-phenyl-1H-quinolin-2-one;
3-(1-Benzyl-1H-[1,2,3]triazol-4-yl)-6-chloro-4-phenyl-1H-quinolin-2-one;
3-(3-Methyl-isoxazol-5-yl)-6-nitro-4-phenyl-1H-quinolin-2-one;
6-Amino-3-(3-methyl-isoxazol-5-yl)-4-phenyl-1H-quinolin-2-one;
N-[3-(3-Methyl-isoxazol-5-yl)-2-oxo-4-phenyl-1,2-dihydro-quinolin-6-yl]-acetamide;
N-[3-(3-Methyl-isoxazol-5-yl)-2-oxo-4-phenyl-1,2-dihydro-quinolin-6-yl]-methanesulfonamide;
N-[3-(3-Methyl-isoxazol-5-yl)-2-oxo-4-phenyl-1,2-dihydro-quinolin-6-yl]-acrylamide;
3-(3-Methyl-isoxazol-5-yl)-4-phenyl-6-(pyridin-2-ylamino)-1H-quinolin-2-one;
3-(3H-Imidazol-4-yl)-2-oxo-4-phenyl-1,2-dihydro-quinoline-6-carbonitrile;
3-(1-Methyl-1H-imidazol-4-yl)-2-oxo-4-phenyl-1,2-dihydro-quinoline-6-carbonitrile;
3-(3-Amino-isoxazol-5-yl)-6-chloro-4-phenyl-1H-quinolin-2-one;
N-[5-(6-Chloro-2-oxo-4-phenyl-1,2-dihydro-quinolin-3-yl)-isoxazol-3-yl]-acetamide;
[5-(6-Chloro-2-oxo-4-phenyl-1,2-dihydro-quinolin-3-yl)-isoxazol-3-yl]-carbamic acid 2-methanesulfonyl-ethyl ester;
1-[5-(6-Chloro-2-oxo-4-phenyl-1,2-dihydro-quinolin-3-yl)-isoxazol-3-yl]-3-(2-morpholin-4-yl-ethyl)-urea;
3-(3-Methyl-isoxazol-5-yl)-4,6-diphenyl-1H-quinolin-2-one;
3-(3-Methyl-isoxazol-5-yl)-4-phenyl-6-(3-trifluoromethyl-phenyl)-1H-quinolin-2-one;
6-(3-Methoxy-phenyl)-3-(3-methyl-isoxazol-5-yl)-4-phenyl-1H-quinolin-2-one;
3-(3-Methyl-isoxazol-5-yl)-2-oxo-4-phenyl-1,2-dihydro-quinoline-6-carbonitrile;
3-(3-Methyl-isoxazol-5-yl)-6-methylsulfanyl-4-phenyl-1H-quinolin-2-one;
6-Methanesulfonyl-3-(3-methyl-isoxazol-5-yl)-4-phenyl-1H-quinolin-2-one;
6-Fluoro-3-(3-methyl-isoxazol-5-yl)-4-phenyl-1H-quinolin-2-one;
3-(3-Methyl-isoxazol-5-yl)-4-phenyl-1H-quinolin-2-one;
6-Fluoro-7-methoxy-3-(3-methyl-isoxazol-5-yl)-4-phenyl-1H-quinolin-2-one;
5,6-Dichloro-3-(3-methyl-isoxazol-5-yl)-4-phenyl-1H-quinolin-2-one;
6-Chloro-4-(4-ethyl-phenyl)-3-(3H-imidazol-4-yl)-1H-quinolin-2-one;
6-Bromo-4-(4-ethyl-phenyl)-3-(3H-imidazol-4-yl)-1H-quinolin-2-one;
4-(4-Ethyl-phenyl)-3-(3H-imidazol-4-yl)-2-oxo-1,2-dihydro-quinoline-6-carbonitrile;
6-Chloro-4-(4-ethyl-phenyl)-3-(3-methyl-isoxazlo-5-yl)-1H-quinolin-2-one;
6-Chloro-3-(3-methyl-isoxazol-5-yl)-4-m-tolyl-1H-quinolin-2-one;
6-Chloro-3-(3-methyl-isoxazol-5-yl)-4-p-tolyl-1H-quinolin-2-one;
6-Chloro-3-(3-methyl-isoxazol-5-yl)-4-o-tolyl-1H-quinolin-2-one;
6-Chloro-4-(2-chloro-phenyl)-3-(3-methyl-isoxazol-5-yl)-1H-quinolin-2-one;
6-Chloro-4-(4-chloro-phenyl)-3-(3-methyl-isoxazol-5-yl)-1H-quinolin-2-one;
4-(4-Acetyl-3-hydroxy-phenyl)-6-chloro-3-(3-methyl-isoxazol-5-yl)-1H-quinolin-2-one;
4-(3-Acetyl-4-hydroxy-phenyl)-6-chloro-3-(3-methyl-isoxazol-5-yl)-1H-quinolin-2-one;
6-Chloro-4-(4-hydroxy-phenyl)-3-(3-methyl-isoxazol-5-yl)-1H-quinolin-2-one;

4-(5-Acetyl-2-methoxy-phenyl)-6-chloro-3-(3-methyl-isoxazol-5-yl)-1H-quinolin-2-one;
4-(5-Acetyl-2-hydroxy-phenyl)-6-chloro-3-(3-methyl-isoxazol-5-yl)-1H-quinolin-2-one;
6-Chloro-4-(2-methoxy-phenyl)-3-(3-methyl-isoxazol-5-yl)-1H-quinolin-2-one;
6-Chloro-4-(4-methoxy-phenyl)-3-(3-methyl-isoxazol-5-yl)-1H-quinolin-2-one;
6-Chloro-4-(2-hydroxy-phenyl)-3-(3-methyl-isoxazol-5-yl)-1H-quinolin-2-one;
6-Chloro-4-(3-methoxy-phenyl)-3-(3-methyl-isoxazol-5-yl)-1H-quinolin-2-one;
6-Chloro-4-(4-fluoro-phenyl)-3-(3-methyl-isoxazol-5-yl)-1H-quinolin-2-one;
4-Biphenyl-4-yl-6-chloro-3-(3-methyl-isoxazol-5-yl)-1H-quinolin-2-one;
6-Chloro-3-(3-methyl-isoxazol-5-yl)-4-(4-propyl-phenyl)-1H-quinolin-2-one;
6-Chloro-4-(4-isopropyl-phenyl)-3-(3-methyl-i soxazol-5-yl)-1H-quinolin-2-one;
6-Bromo-4-(4-ethyl-phenyl)-3-(3-methyl-isoxazol-5-yl)-1H-quinolin-2-one;
4-(4-Ethyl-phenyl)-3-(3-methyl-isoxazol-5-yl)-2-oxo-1,2-dibydro-quinoline-6-carbonitrile;
4-(4-tert-Butyl-phenyl)-3-(3-methyl-isoxazol-5-yl)-2-oxo-1,2-dihydro-quinoline-6-carbonitrile;
3-(3-Methyl-isoxazol-5-yl)-2-oxo-4-(4-propyl-phenyl)-1,2-dihydro-quinoline-6-carbonitrile;
4-(4-Isopropyl-phenyl)-3-(3-methyl-isoxazol-5-yl)-2-oxo-1,2-dihydro-quinoline-6-carbonitrile;
3-(3-Methyl-isoxazol-5-yl)-2-oxo-4-(4-trifluoromethyl-phenyl)-1,2-dihydro-quinoline-6-carbonitrile;
4-(4-Acetyl-phenyl)-3-(3-methyl-isoxazol-5-yl)-2-oxo-1,2-dihydro-quinoline-6-carbonitrile;
3-(3-Methyl-isoxazol-5-yl)-4-(4-methylsulfanyl-phenyl)-2-oxo-1,2-dihydro-quinoline-6-carbonitrile;
3-(3-Methyl-isoxazol-5-yl)-2-oxo-4-(4-vinyl-phenyl)-1,2-dihydro-quinoline-6-carbonitrile;
4-(4-Ethyl-phenyl)-3-(2-methyl-thiazol-4-yl)-2-oxo-1,2-dihydro-quinoline-6-carbonitrile
3-(3-Methyl-isoxazol-5-yl)-2-oxo-4-(4-trifluoromethoxy-phenyl)-1,2-dihydro-quinoline-6-carbonitrile;
4-(4-Cyano-phenyl)-3-(3-methyl-isoxazol-5-yl)-2-oxo-1,2-dihydro-quinoline-6-carbonitrile;
4-(4-Methanesulfonyl-phenyl)-3-(3-methyl-isoxazol-5-yl)-2-oxo-1,2-dihydro-quinoline-6-carbonitrile;
6-Bromo-3-(3-methyl-isoxazol-5-yl)-4-phenyl-1H-quinoline-2-thione;
6-Bromo-3-(3H-imidazol-4-yl)-4-phenyl-1H-quinolin-2-one;
6-Bromo-3-(3H-imidazol-4-yl)-1-methyl-4-phenyl-1H-quinolin-2-one; and
6-Chloro-4-phenyl-3-pyridin-2-yl-1H-quinolin-2-one.

6. A pharmaceutical composition, comprising a compound of any one of claim 1 and a pharmaceutically acceptable carrier.

* * * * *